US009289132B2

(12) United States Patent
Ghaffari et al.

(10) Patent No.: US 9,289,132 B2
(45) Date of Patent: Mar. 22, 2016

(54) CATHETER BALLOON HAVING STRETCHABLE INTEGRATED CIRCUITRY AND SENSOR ARRAY

(75) Inventors: Roozbeh Ghaffari, Cambridge, MA (US); Gilman Callsen, Malden, MA (US); William J. Arora, Boston, MA (US); Benjamin Schlatka, Lexington, MA (US)

(73) Assignee: MC10, Inc., Lexington, MA (US)

( * ) Notice: Subject to any disclaimer, the term of this patent is extended or adjusted under 35 U.S.C. 154(b) by 0 days.

(21) Appl. No.: 12/575,008

(22) Filed: Oct. 7, 2009

(65) Prior Publication Data

US 2010/0087782 A1    Apr. 8, 2010

Related U.S. Application Data

(60) Provisional application No. 61/103,361, filed on Oct. 7, 2008, provisional application No. 61/113,007, filed on Nov. 10, 2008.

(51) Int. Cl.
| | |
|---|---|
| *A61B 5/01* | (2006.01) |
| *A61B 1/00* | (2006.01) |
| *A61B 5/02* | (2006.01) |
| *A61B 5/00* | (2006.01) |

(Continued)

(52) U.S. Cl.
CPC ............ *A61B 5/015* (2013.01); *A61B 1/00082* (2013.01); *A61B 1/3137* (2013.01); *A61B 5/01* (2013.01); *A61B 5/02014* (2013.01); *A61B 5/0536* (2013.01); *A61B 5/6853* (2013.01); *A61F 2/958* (2013.01); *A61M 25/10* (2013.01); *A61M 2025/1086* (2013.01)

(58) Field of Classification Search
CPC ............... A61M 2025/1086; A61M 25/10; A61B 5/01; A61B 1/00082; A61B 1/3137; A61B 5/015; A61B 5/02014; A61B 5/0536; A61B 5/6853; H01L 23/52; H01L 23/528; H01L 2924/14; A61F 2/958; H05K 1/0283
USPC .............. 604/103.01; 600/381, 361; 623/1.11
See application file for complete search history.

(56) References Cited

U.S. PATENT DOCUMENTS

| | | | |
|---|---|---|---|
| 3,716,861 | A | 2/1973 | Root |
| 3,805,427 | A | 4/1974 | Epstein |

(Continued)

FOREIGN PATENT DOCUMENTS

| | | |
|---|---|---|
| CN | 1222758 | 7/1999 |
| CN | 1454045 | 11/2003 |

(Continued)

OTHER PUBLICATIONS

Abbaschian et al. (2005) "High Pressure-High Temperature Growth of Diamond Crystals Using Split Sphere Apparatus," *Diamond Relat. Mater.* 14(11-12):1916-1919.

(Continued)

*Primary Examiner* — Nathan R Price
*Assistant Examiner* — Weng Lee
(74) *Attorney, Agent, or Firm* — Nixon Peabody LLP

(57) ABSTRACT

A system, device and method are presented for utilizing stretchable active integrated circuits with inflatable bodies. The invention allows for such operative features to come into direct contact with body structures, such as the inner wall of a lumen. Such direct contact increases accuracy of measurement and delivery of therapy.

51 Claims, 4 Drawing Sheets

(51) Int. Cl.
 *A61B 5/053* (2006.01)
 *A61B 1/313* (2006.01)
 *A61M 25/10* (2013.01)
 *A61F 2/958* (2013.01)

(56) References Cited

U.S. PATENT DOCUMENTS

| | | |
|---|---|---|
| 3,949,410 A | 4/1976 | Bassous |
| 4,058,418 A | 11/1977 | Lindmayer et al. |
| 4,392,451 A | 7/1983 | Mickelsen et al. |
| 4,416,288 A | 11/1983 | Freeman |
| 4,471,003 A | 9/1984 | Cann |
| 4,487,162 A | 12/1984 | Cann |
| 4,658,153 A | 4/1987 | Brosh et al. |
| 4,663,828 A | 5/1987 | Hanak |
| 4,761,335 A | 8/1988 | Aurichio et al. |
| 4,763,275 A | 8/1988 | Carlin |
| 4,766,670 A | 8/1988 | Gazdik et al. |
| 4,784,720 A | 11/1988 | Douglas |
| 4,855,017 A | 8/1989 | Douglas |
| 5,041,973 A | 8/1991 | Lebron et al. |
| 5,086,785 A | 2/1992 | Gentile et al. |
| 5,108,819 A | 4/1992 | Heller et al. |
| 5,118,400 A | 6/1992 | Wollam |
| 5,147,519 A | 9/1992 | Legge |
| 5,178,957 A | 1/1993 | Kolpe et al. |
| 5,204,144 A | 4/1993 | Cann et al. |
| 5,306,370 A | 4/1994 | Black et al. |
| 5,313,094 A | 5/1994 | Beyer et al. |
| 5,331,966 A | 7/1994 | Bennett et al. |
| 5,360,987 A | 11/1994 | Shibib |
| 5,403,700 A | 4/1995 | Heller et al. |
| 5,427,096 A | 6/1995 | Bogusiewiz et al. |
| 5,434,751 A | 7/1995 | Cole, Jr. et al. |
| 5,439,575 A | 8/1995 | Thornton et al. |
| 5,455,178 A | 10/1995 | Fattnger |
| 5,455,430 A | 10/1995 | Noguchi et al. |
| 5,469,845 A | 11/1995 | Delonzor et al. |
| 5,477,088 A | 12/1995 | Rockett et al. |
| 5,501,893 A | 3/1996 | Laermer et al. |
| 5,525,815 A | 6/1996 | Einset |
| 5,539,935 A | 7/1996 | Rush, III |
| 5,545,291 A | 8/1996 | Smith et al. |
| 5,549,108 A * | 8/1996 | Edwards et al. ............... 600/381 |
| 5,560,974 A | 10/1996 | Langley |
| 5,567,975 A | 10/1996 | Walsh et al. |
| 5,625,471 A | 4/1997 | Smith |
| 5,648,148 A | 7/1997 | Simpson |
| 5,674,198 A * | 10/1997 | Leone ..................... 604/101.05 |
| 5,687,737 A | 11/1997 | Branham et al. |
| 5,691,245 A | 11/1997 | Bakhit et al. |
| 5,746,207 A | 5/1998 | McLaughlin et al. |
| 5,753,529 A | 5/1998 | Chang et al. |
| 5,757,081 A | 5/1998 | Chang et al. |
| 5,767,578 A | 6/1998 | Chang et al. |
| 5,772,905 A | 6/1998 | Chou |
| 5,779,698 A | 7/1998 | Clayman |
| 5,783,856 A | 7/1998 | Smith et al. |
| 5,790,151 A | 8/1998 | Mills |
| 5,811,790 A | 9/1998 | Endo et al. |
| 5,817,242 A | 10/1998 | Biebuyck et al. |
| 5,824,186 A | 10/1998 | Smith et al. |
| 5,837,546 A | 11/1998 | Allen |
| 5,860,974 A | 1/1999 | Abele |
| 5,871,443 A | 2/1999 | Edwards et al. |
| 5,904,545 A | 5/1999 | Smith et al. |
| 5,907,189 A | 5/1999 | Mertol |
| 5,907,477 A | 5/1999 | Tuttle et al. |
| 5,915,180 A | 6/1999 | Hara et al. |
| 5,917,534 A | 6/1999 | Rajeswaran |
| 5,919,155 A | 7/1999 | Lattin |
| 5,928,001 A | 7/1999 | Gillette et al. |
| 5,955,781 A | 9/1999 | Joshi et al. |
| 5,968,839 A | 10/1999 | Blatt |
| 5,976,683 A | 11/1999 | Liehrr et al. |
| 5,978,972 A | 11/1999 | Stewart |
| 5,979,972 A | 11/1999 | Gehman |
| 5,998,291 A | 12/1999 | Bakhit et al. |
| 6,009,632 A | 1/2000 | Douglas |
| 6,024,702 A | 2/2000 | Iverson |
| 6,057,212 A | 5/2000 | Cha et al. |
| 6,063,046 A | 5/2000 | Allum |
| 6,080,608 A | 6/2000 | Nowak |
| 6,097,984 A | 8/2000 | Douglas |
| 6,121,110 A | 9/2000 | Hong |
| 6,148,127 A | 11/2000 | Adams et al. |
| 6,150,602 A | 11/2000 | Campbell |
| 6,165,391 A | 12/2000 | Vedamuttu |
| 6,165,885 A | 12/2000 | Gaynes et al. |
| 6,171,730 B1 | 1/2001 | Kuroda et al. |
| 6,181,551 B1 | 1/2001 | Herman |
| 6,225,149 B1 | 5/2001 | Gan et al. |
| 6,236,883 B1 | 5/2001 | Ciaccio et al. |
| 6,265,326 B1 | 7/2001 | Ueno |
| 6,267,775 B1 | 7/2001 | Clerc et al. |
| 6,274,508 B1 | 8/2001 | Jacobsen et al. |
| 6,276,775 B1 | 8/2001 | Schulte |
| 6,277,712 B1 | 8/2001 | Kang et al. |
| 6,281,038 B1 | 8/2001 | Jacobsen et al. |
| 6,282,960 B1 | 9/2001 | Samuels et al. |
| 6,284,418 B1 | 9/2001 | Trantolo |
| 6,291,896 B1 | 9/2001 | Smith |
| 6,301,500 B1 | 10/2001 | Van Herk |
| 6,309,351 B1 | 10/2001 | Kurnik |
| 6,316,278 B1 | 11/2001 | Jacobsen et al. |
| 6,316,283 B1 | 11/2001 | Saurer |
| 6,317,175 B1 | 11/2001 | Salerno et al. |
| 6,322,895 B1 | 11/2001 | Canham |
| 6,322,963 B1 | 11/2001 | Bauer |
| 6,334,960 B1 | 1/2002 | Willson et al. |
| 6,344,616 B1 | 2/2002 | Yokokawa |
| 6,360,615 B1 | 3/2002 | Smela |
| 6,380,729 B1 | 4/2002 | Smith |
| 6,403,397 B1 | 6/2002 | Katz |
| 6,403,944 B1 | 6/2002 | MacKenzie |
| 6,413,790 B1 | 7/2002 | Duthaler et al. |
| 6,414,783 B2 | 7/2002 | Zavracky et al. |
| 6,417,025 B1 | 7/2002 | Gengel |
| 6,420,266 B1 | 7/2002 | Smith et al. |
| 6,433,401 B1 | 8/2002 | Clark et al. |
| 6,451,191 B1 | 9/2002 | Bentsen et al. |
| 6,459,418 B1 | 10/2002 | Comiskey et al. |
| 6,468,638 B2 | 10/2002 | Jacobsen et al. |
| 6,473,982 B1 | 11/2002 | Schimes |
| 6,479,395 B1 | 11/2002 | Smith et al. |
| 6,504,105 B1 | 1/2003 | Acocella et al. |
| 6,517,995 B1 | 2/2003 | Jacobson et al. |
| 6,518,168 B1 | 2/2003 | Clem et al. |
| 6,527,964 B1 | 3/2003 | Smith et al. |
| 6,555,408 B1 | 4/2003 | Jacobsen et al. |
| 6,566,744 B2 | 5/2003 | Gengel |
| 6,567,158 B1 | 5/2003 | Falciai et al. |
| 6,580,151 B2 | 6/2003 | Vandeputte et al. |
| 6,586,338 B2 | 7/2003 | Smith et al. |
| 6,590,346 B1 | 7/2003 | Hadley et al. |
| 6,606,079 B1 | 8/2003 | Smith |
| 6,606,247 B2 | 8/2003 | Credelle et al. |
| 6,608,370 B1 | 8/2003 | Chen et al. |
| 6,613,979 B1 | 9/2003 | Miller et al. |
| 6,623,579 B1 | 9/2003 | Smith et al. |
| 6,639,578 B1 | 10/2003 | Comiskey et al. |
| 6,655,286 B2 | 12/2003 | Rogers |
| 6,657,289 B1 | 12/2003 | Craig et al. |
| 6,661,037 B2 | 12/2003 | Pan et al. |
| 6,665,044 B1 | 12/2003 | Jacobsen et al. |
| 6,666,821 B2 | 12/2003 | Keimel |
| 6,667,548 B2 | 12/2003 | O'Connor et al. |
| 6,683,663 B1 | 1/2004 | Hadley et al. |
| 6,693,384 B1 | 2/2004 | Vicentini et al. |
| 6,706,402 B2 | 3/2004 | Rueckes et al. |
| 6,720,469 B1 | 4/2004 | Curtis et al. |
| 6,723,576 B2 | 4/2004 | Nozawa et al. |
| 6,730,990 B2 | 5/2004 | Kondo et al. |
| 6,731,353 B1 | 5/2004 | Credelle et al. |

(56) References Cited

U.S. PATENT DOCUMENTS

| | | |
|---|---|---|
| 6,743,982 B2 | 6/2004 | Biegelsen et al. |
| 6,762,510 B2 | 7/2004 | Fock et al. |
| 6,780,696 B1 | 8/2004 | Schatz |
| 6,784,450 B2 | 8/2004 | Pan et al. |
| 6,784,844 B1 | 8/2004 | Boakes et al. |
| 6,787,052 B1 | 9/2004 | Vaganov |
| 6,805,809 B2 | 10/2004 | Nuzzo et al. |
| 6,814,898 B1 | 11/2004 | Deeman et al. |
| 6,816,380 B2 | 11/2004 | Credelle et al. |
| 6,826,509 B2 | 11/2004 | Crisco et al. |
| 6,836,744 B1 | 12/2004 | Asphahani et al. |
| 6,844,673 B1 | 1/2005 | Bernkopf |
| 6,848,162 B2 | 2/2005 | Arneson et al. |
| 6,850,312 B2 | 2/2005 | Jacobsen et al. |
| 6,856,830 B2 | 2/2005 | He |
| 6,863,219 B1 | 3/2005 | Jacobsen et al. |
| 6,864,435 B2 | 3/2005 | Hermanns et al. |
| 6,864,570 B2 | 3/2005 | Smith |
| 6,872,645 B2 | 3/2005 | Duan et al. |
| 6,878,871 B2 | 4/2005 | Scher et al. |
| 6,881,979 B2 | 4/2005 | Starikov et al. |
| 6,885,030 B2 | 4/2005 | Onozuka et al. |
| 6,887,450 B2 | 5/2005 | Chen et al. |
| 6,900,094 B2 | 5/2005 | Hammond et al. |
| 6,917,061 B2 | 7/2005 | Pan et al. |
| 6,936,181 B2 | 8/2005 | Bulthaup et al. |
| 6,949,199 B1 | 9/2005 | Gauzner et al. |
| 6,949,206 B2 | 9/2005 | Whiteford et al. |
| 6,950,220 B2 | 9/2005 | Abramson et al. |
| 6,967,362 B2 | 11/2005 | Nam et al. |
| 6,984,934 B2 | 1/2006 | Moller et al. |
| 6,989,285 B2 | 1/2006 | Ball |
| 7,029,951 B2 | 4/2006 | Chen et al. |
| 7,033,961 B1 | 4/2006 | Smart et al. |
| 7,054,784 B2 | 5/2006 | Flentov et al. |
| 7,059,835 B2 | 6/2006 | Tiemann |
| 7,067,903 B2 | 6/2006 | Tachibana et al. |
| 7,081,642 B2 | 7/2006 | Onozuka et al. |
| 7,116,318 B2 | 10/2006 | Amundson et al. |
| 7,132,313 B2 | 11/2006 | O'Connor et al. |
| 7,148,512 B2 | 12/2006 | Leu et al. |
| 7,158,277 B2 | 1/2007 | Berggren et al. |
| 7,169,546 B2 | 1/2007 | Suzuki et al. |
| 7,169,669 B2 | 1/2007 | Blakers et al. |
| 7,170,164 B2 | 1/2007 | Chen et al. |
| 7,186,624 B2 | 3/2007 | Welser et al. |
| 7,190,051 B2 | 3/2007 | Mech et al. |
| 7,195,733 B2 | 3/2007 | Rogers et al. |
| 7,223,609 B2 | 5/2007 | Anvar et al. |
| 7,223,632 B2 | 5/2007 | Onozuka et al. |
| 7,252,664 B2 | 8/2007 | Nasab et al. |
| 7,253,442 B2 | 8/2007 | Huang et al. |
| 7,255,919 B2 | 8/2007 | Sakata et al. |
| 7,265,298 B2 | 9/2007 | Maghribi |
| 7,291,146 B2 | 11/2007 | Steinke et al. |
| 7,291,540 B2 | 11/2007 | Mech et al. |
| 7,293,353 B2 | 11/2007 | Matsuda |
| 7,302,751 B2 | 12/2007 | Hamburgen |
| 7,337,012 B2 | 2/2008 | Maghribi |
| 7,374,968 B2 | 5/2008 | Kornilovich et al. |
| 7,425,523 B2 | 9/2008 | Ikemizu et al. |
| 7,487,587 B2 | 2/2009 | Vanfleteren |
| 7,491,892 B2 | 2/2009 | Wagner |
| 7,521,292 B2 | 4/2009 | Rogers et al. |
| 7,525,304 B1 | 4/2009 | Feng et al. |
| 7,526,389 B2 | 4/2009 | Greenwald et al. |
| 7,552,031 B2 | 6/2009 | Vock et al. |
| 7,557,367 B2 | 7/2009 | Rogers et al. |
| 7,593,086 B2 | 9/2009 | Jeong et al. |
| 7,618,260 B2 | 11/2009 | Daniel et al. |
| 7,622,367 B1 | 11/2009 | Nuzzo et al. |
| 7,629,691 B2 | 12/2009 | Roush et al. |
| 7,633,761 B2 | 12/2009 | Kim |
| 7,635,755 B2 | 12/2009 | Kaplan et al. |
| 7,674,882 B2 | 3/2010 | Kaplan et al. |
| 7,700,402 B2 | 4/2010 | Wild et al. |
| 7,704,684 B2 | 4/2010 | Rogers et al. |
| 7,705,280 B2 | 4/2010 | Nuzzo et al. |
| 7,709,961 B2 | 5/2010 | Greenberg et al. |
| 7,727,199 B2 * | 6/2010 | Fernandes et al. ........ 604/164.09 |
| 7,727,575 B2 | 6/2010 | Kaplan et al. |
| 7,732,012 B2 | 6/2010 | Hongu et al. |
| 7,742,795 B2 | 6/2010 | Stone et al. |
| 7,759,167 B2 | 7/2010 | Vanfleteren et al. |
| 7,769,472 B2 | 8/2010 | Gerber |
| 7,799,699 B2 | 9/2010 | Nuzzo et al. |
| 7,838,964 B2 | 11/2010 | Carobolante et al. |
| 7,842,780 B2 | 11/2010 | Kaplan et al. |
| 7,857,781 B2 | 12/2010 | Noda et al. |
| 7,871,661 B2 | 1/2011 | Maghribi et al. |
| 7,884,540 B2 | 2/2011 | Sung et al. |
| 7,909,971 B2 | 3/2011 | Nuzzo et al. |
| 7,932,123 B2 | 4/2011 | Rogers et al. |
| 7,935,056 B2 | 5/2011 | Zbdelick |
| 7,943,491 B2 | 5/2011 | Nuzzo et al. |
| 7,960,246 B2 | 6/2011 | Flamand |
| 7,972,875 B2 | 7/2011 | Rogers et al. |
| 7,982,296 B2 | 7/2011 | Nuzzo |
| 8,008,575 B2 | 8/2011 | De Ceuster et al. |
| 8,039,847 B2 | 10/2011 | Nuzzo et al. |
| 8,107,248 B2 | 1/2012 | Shin et al. |
| 8,198,621 B2 | 6/2012 | Rogers |
| 8,207,473 B2 | 6/2012 | Axisa |
| 8,217,381 B2 | 7/2012 | Rogers |
| 8,252,191 B2 | 8/2012 | Heejoon et al. |
| 8,367,035 B2 | 2/2013 | Rogers et al. |
| 8,394,706 B2 | 3/2013 | Nuzzo et al. |
| 8,431,828 B2 | 4/2013 | Vanfleteren |
| 8,440,546 B2 | 5/2013 | Nuzzo et al. |
| 8,552,299 B2 | 10/2013 | Rogers |
| 8,664,699 B2 | 3/2014 | Nuzzo |
| 8,679,888 B2 | 3/2014 | Rogers |
| 8,729,524 B2 | 5/2014 | Rogers |
| 8,754,396 B2 | 6/2014 | Rogers |
| 8,865,489 B2 | 10/2014 | Rogers |
| 8,905,772 B2 | 12/2014 | Rogers |
| 2001/0003043 A1 | 6/2001 | Metspalu et al. |
| 2001/0012918 A1 | 8/2001 | Swanson |
| 2001/0021867 A1 | 9/2001 | Kordis |
| 2002/0021445 A1 | 2/2002 | Boxhevolnyi et al. |
| 2002/0026127 A1 | 2/2002 | Balbierz et al. |
| 2002/0082515 A1 | 6/2002 | Campbell et al. |
| 2002/0087146 A1 * | 7/2002 | Schu et al. ................ 604/891.1 |
| 2002/0094701 A1 * | 7/2002 | Biegelsen et al. ............. 439/32 |
| 2002/0095087 A1 | 7/2002 | Mourad et al. |
| 2002/0110766 A1 | 8/2002 | Tsai et al. |
| 2002/0113739 A1 | 8/2002 | Howard |
| 2002/0128700 A1 | 9/2002 | Cross, Jr. |
| 2002/0151934 A1 | 10/2002 | Levine |
| 2003/0006527 A1 | 1/2003 | Rabolt et al. |
| 2003/0017848 A1 | 1/2003 | Engstrom et al. |
| 2003/0032892 A1 | 2/2003 | Erlach et al. |
| 2003/0082889 A1 | 5/2003 | Maruyama et al. |
| 2003/0087476 A1 | 5/2003 | Oohata et al. |
| 2003/0097165 A1 | 5/2003 | Krulevitch et al. |
| 2003/0120271 A1 | 6/2003 | Burnside et al. |
| 2003/0138704 A1 | 7/2003 | Mei et al. |
| 2003/0149456 A1 | 8/2003 | Rottenberg et al. |
| 2003/0171691 A1 | 9/2003 | Casscells et al. |
| 2003/0178316 A1 | 9/2003 | Jacobs et al. |
| 2003/0214408 A1 | 11/2003 | Grajales |
| 2003/0222282 A1 | 12/2003 | Fjelstad et al. |
| 2003/0227116 A1 | 12/2003 | Halik et al. |
| 2004/0005723 A1 | 1/2004 | Empedocles et al. |
| 2004/0006264 A1 | 1/2004 | Mojarradi et al. |
| 2004/0026684 A1 | 2/2004 | Empedocles |
| 2004/0061543 A1 | 4/2004 | Nam et al. |
| 2004/0079464 A1 | 4/2004 | Kumakura |
| 2004/0081384 A1 | 4/2004 | Datesman et al. |
| 2004/0085469 A1 | 5/2004 | Johnson |
| 2004/0092806 A1 | 5/2004 | Sagon |
| 2004/0095658 A1 | 5/2004 | Buretea et al. |
| 2004/0106334 A1 | 6/2004 | Suzuki et al. |
| 2004/0112964 A1 | 6/2004 | Empedocles et al. |

(56) References Cited

U.S. PATENT DOCUMENTS

| | | |
|---|---|---|
| 2004/0135094 A1 | 7/2004 | Niigaki et al. |
| 2004/0136866 A1 | 7/2004 | Pontis et al. |
| 2004/0138558 A1 | 7/2004 | Dunki-Jacobs et al. |
| 2004/0146560 A1 | 7/2004 | Whiteford et al. |
| 2004/0149921 A1 | 8/2004 | Smyk |
| 2004/0155290 A1 | 8/2004 | Mech et al. |
| 2004/0171969 A1 | 9/2004 | Socci |
| 2004/0178390 A1 | 9/2004 | Whiteford et al. |
| 2004/0178466 A1 | 9/2004 | Merrill et al. |
| 2004/0192082 A1* | 9/2004 | Wagner et al. ................ 439/67 |
| 2004/0200734 A1 | 10/2004 | Co |
| 2004/0206448 A1 | 10/2004 | Dubrow |
| 2004/0211458 A1 | 10/2004 | Gui et al. |
| 2004/0211459 A1 | 10/2004 | Suenaga et al. |
| 2004/0229830 A1 | 11/2004 | Tachibana et al. |
| 2004/0239650 A1 | 12/2004 | Mackey |
| 2004/0243204 A1 | 12/2004 | Maghribi |
| 2004/0250950 A1 | 12/2004 | Dubrow |
| 2004/0252559 A1 | 12/2004 | Gupta |
| 2005/0020094 A1 | 1/2005 | Forbes et al. |
| 2005/0021103 A1 | 1/2005 | DiLorenzo |
| 2005/0037511 A1 | 2/2005 | Sharrock |
| 2005/0038498 A1 | 2/2005 | Dubrow et al. |
| 2005/0054939 A1 | 3/2005 | Ben-Ari et al. |
| 2005/0082526 A1 | 4/2005 | Bedell et al. |
| 2005/0107716 A1 | 5/2005 | Eaton et al. |
| 2005/0113744 A1 | 5/2005 | Donoghue |
| 2005/0115308 A1 | 6/2005 | Koram et al. |
| 2005/0124712 A1 | 6/2005 | Anderson et al. |
| 2005/0133954 A1 | 6/2005 | Homola |
| 2005/0136501 A1 | 6/2005 | Kuriger |
| 2005/0171524 A1 | 8/2005 | Stern et al. |
| 2005/0177335 A1 | 8/2005 | Crisco |
| 2005/0203366 A1 | 9/2005 | Donoghue |
| 2005/0214962 A1 | 9/2005 | Daniels et al. |
| 2005/0227389 A1 | 10/2005 | Bhattacharya et al. |
| 2005/0233546 A1 | 10/2005 | Oohata et al. |
| 2005/0238967 A1 | 10/2005 | Rogers et al. |
| 2005/0255686 A1 | 11/2005 | Yamano et al. |
| 2005/0260706 A1 | 11/2005 | Kaplan et al. |
| 2005/0261561 A1 | 11/2005 | Jones et al. |
| 2006/0038182 A1* | 2/2006 | Rogers et al. ................ 257/77 |
| 2006/0049485 A1 | 3/2006 | Pan et al. |
| 2006/0056161 A1 | 3/2006 | Shin et al. |
| 2006/0068576 A1 | 3/2006 | Burdick, Jr. et al. |
| 2006/0076561 A1 | 4/2006 | Hicki et al. |
| 2006/0084012 A1 | 4/2006 | Nuzzo et al. |
| 2006/0084394 A1 | 4/2006 | Engstrom et al. |
| 2006/0085976 A1 | 4/2006 | Eldridge et al. |
| 2006/0102525 A1 | 5/2006 | Volkel et al. |
| 2006/0106321 A1 | 5/2006 | Lewinsky et al. |
| 2006/0119853 A1 | 6/2006 | Baumberg et al. |
| 2006/0127817 A1 | 6/2006 | Ramanujan et al. |
| 2006/0129056 A1 | 6/2006 | Leuthardt et al. |
| 2006/0132025 A1 | 6/2006 | Gao et al. |
| 2006/0134893 A1 | 6/2006 | Savage et al. |
| 2006/0154398 A1 | 7/2006 | Qing et al. |
| 2006/0159837 A1 | 7/2006 | Kaplan et al. |
| 2006/0169989 A1 | 8/2006 | Bhattacharya et al. |
| 2006/0173364 A1 | 8/2006 | Clancy et al. |
| 2006/0177479 A1 | 8/2006 | Giachelli et al. |
| 2006/0178655 A1 | 8/2006 | Santini et al. |
| 2006/0244105 A1 | 11/2006 | Forbes et al. |
| 2006/0255341 A1 | 11/2006 | Pinnington et al. |
| 2006/0273279 A1 | 12/2006 | Kaplan et al. |
| 2006/0279191 A1 | 12/2006 | Gehegan et al. |
| 2006/0286488 A1 | 12/2006 | Rogers et al. |
| 2006/0286785 A1 | 12/2006 | Rogers |
| 2007/0009968 A1 | 1/2007 | Cunningham et al. |
| 2007/0016279 A1* | 1/2007 | Konstantino et al. ......... 623/1.11 |
| 2007/0027514 A1* | 2/2007 | Gerber .................... 607/116 |
| 2007/0031607 A1 | 2/2007 | Dubson et al. |
| 2007/0032089 A1 | 2/2007 | Nuzzo et al. |
| 2007/0043416 A1 | 2/2007 | Callas et al. |
| 2007/0058254 A1 | 3/2007 | Kim |
| 2007/0073130 A1 | 3/2007 | Finch et al. |
| 2007/0104944 A1 | 5/2007 | Laude et al. |
| 2007/0108389 A1 | 5/2007 | Makela et al. |
| 2007/0122819 A1 | 5/2007 | Wu |
| 2007/0187862 A1 | 8/2007 | Kaplan et al. |
| 2007/0212730 A1 | 9/2007 | Vepari et al. |
| 2007/0213616 A1 | 9/2007 | Anderson et al. |
| 2007/0227586 A1 | 10/2007 | Zapalac |
| 2007/0233208 A1 | 10/2007 | Kurtz et al. |
| 2007/0254468 A1 | 11/2007 | Burdick, Jr. et al. |
| 2008/0000871 A1 | 1/2008 | Suh et al. |
| 2008/0008626 A1 | 1/2008 | Lin et al. |
| 2008/0038236 A1 | 2/2008 | Gimble et al. |
| 2008/0041617 A1 | 2/2008 | Chen et al. |
| 2008/0046080 A1 | 2/2008 | Vanden Bulcke et al. |
| 2008/0054875 A1 | 3/2008 | Saito |
| 2008/0055581 A1 | 3/2008 | Rogers et al. |
| 2008/0077225 A1 | 3/2008 | Carlin et al. |
| 2008/0085272 A1 | 4/2008 | Kaplan et al. |
| 2008/0090322 A1 | 4/2008 | Mech et al. |
| 2008/0102096 A1 | 5/2008 | Molin et al. |
| 2008/0108171 A1 | 5/2008 | Rogers et al. |
| 2008/0108942 A1 | 5/2008 | Brister et al. |
| 2008/0140152 A1 | 6/2008 | Imran et al. |
| 2008/0152281 A1 | 6/2008 | Lundquist et al. |
| 2008/0157234 A1 | 7/2008 | Hong |
| 2008/0157235 A1 | 7/2008 | Rogers et al. |
| 2008/0183076 A1 | 7/2008 | Witte et al. |
| 2008/0188912 A1 | 8/2008 | Stone et al. |
| 2008/0193749 A1 | 8/2008 | Thompson et al. |
| 2008/0203431 A1 | 8/2008 | Garcia et al. |
| 2008/0204021 A1 | 8/2008 | Leussler et al. |
| 2008/0208268 A1 | 8/2008 | Bartic et al. |
| 2008/0212102 A1 | 9/2008 | Nuzzo et al. |
| 2008/0239755 A1 | 10/2008 | Parker et al. |
| 2008/0257586 A1 | 10/2008 | Chen et al. |
| 2008/0259576 A1 | 10/2008 | Johnson et al. |
| 2008/0280360 A1 | 11/2008 | Kaplan et al. |
| 2008/0287167 A1 | 11/2008 | Caine |
| 2008/0288037 A1 | 11/2008 | Neysmith et al. |
| 2008/0293919 A1 | 11/2008 | Kaplan et al. |
| 2008/0313552 A1 | 12/2008 | Buehler et al. |
| 2009/0000377 A1 | 1/2009 | Shipps et al. |
| 2009/0001550 A1 | 1/2009 | Li et al. |
| 2009/0004737 A1 | 1/2009 | Borenstein et al. |
| 2009/0015560 A1 | 1/2009 | Robinson et al. |
| 2009/0028910 A1 | 1/2009 | Desimone et al. |
| 2009/0054742 A1 | 2/2009 | Kaminska et al. |
| 2009/0088750 A1 | 4/2009 | Hushka et al. |
| 2009/0105605 A1 | 4/2009 | Abreu |
| 2009/0107704 A1 | 4/2009 | Vanfleteren |
| 2009/0149930 A1 | 6/2009 | Schenck |
| 2009/0183986 A1 | 7/2009 | Johnson et al. |
| 2009/0184254 A1 | 7/2009 | Miura |
| 2009/0198293 A1 | 8/2009 | Cauller et al. |
| 2009/0199960 A1 | 8/2009 | Nuzzo et al. |
| 2009/0202614 A1 | 8/2009 | Kaplan et al. |
| 2009/0204168 A1 | 8/2009 | Kallmyer et al. |
| 2009/0208555 A1 | 8/2009 | Kuttler et al. |
| 2009/0215385 A1 | 8/2009 | Waters et al. |
| 2009/0221896 A1 | 9/2009 | Rickert et al. |
| 2009/0232963 A1 | 9/2009 | Kaplan et al. |
| 2009/0234026 A1 | 9/2009 | Kaplan et al. |
| 2009/0247909 A1 | 10/2009 | Mukumoto |
| 2009/0261828 A1 | 10/2009 | Nordmeyer-Massner |
| 2009/0273909 A1 | 11/2009 | Shin et al. |
| 2009/0289246 A1 | 11/2009 | Schneider et al. |
| 2009/0294803 A1 | 12/2009 | Nuzzo et al. |
| 2009/0308455 A1 | 12/2009 | Kirscht et al. |
| 2009/0317639 A1 | 12/2009 | Axisa et al. |
| 2009/0322480 A1 | 12/2009 | Benedict et al. |
| 2010/0002402 A1 | 1/2010 | Rogers et al. |
| 2010/0028451 A1 | 2/2010 | Kaplan et al. |
| 2010/0046902 A1 | 2/2010 | Kaplan et al. |
| 2010/0052112 A1 | 3/2010 | Rogers et al. |
| 2010/0055438 A1 | 3/2010 | Kaplan et al. |
| 2010/0059863 A1 | 3/2010 | Rogers et al. |
| 2010/0063404 A1 | 3/2010 | Kaplan et al. |
| 2010/0065784 A1 | 3/2010 | Kaplan et al. |

(56) References Cited

U.S. PATENT DOCUMENTS

| | | |
|---|---|---|
| 2010/0068740 A1 | 3/2010 | Kaplan et al. |
| 2010/0070068 A1 | 3/2010 | Kaplan et al. |
| 2010/0072577 A1 | 3/2010 | Nuzzo et al. |
| 2010/0073669 A1 | 3/2010 | Colvin, Jr. et al. |
| 2010/0087782 A1 | 4/2010 | Ghaffari |
| 2010/0090824 A1 | 4/2010 | Rowell et al. |
| 2010/0096763 A1 | 4/2010 | Kaplan et al. |
| 2010/0116526 A1 | 5/2010 | Arora |
| 2010/0117660 A1 | 5/2010 | Douglas et al. |
| 2010/0120116 A1 | 5/2010 | Kaplan et al. |
| 2010/0121420 A1 | 5/2010 | Fiset et al. |
| 2010/0152619 A1 | 6/2010 | Kalpaxis et al. |
| 2010/0176705 A1 | 7/2010 | Van Herpen et al. |
| 2010/0178304 A1 | 7/2010 | Wang et al. |
| 2010/0178722 A1 | 7/2010 | de Graff |
| 2010/0188799 A1 | 7/2010 | Galvagni et al. |
| 2010/0191328 A1 | 7/2010 | Kaplan et al. |
| 2010/0196447 A1 | 8/2010 | Kaplan et al. |
| 2010/0200752 A1 | 8/2010 | Lee et al. |
| 2010/0203226 A1 | 8/2010 | Kaplan et al. |
| 2010/0245011 A1 | 9/2010 | Chatzopoulos et al. |
| 2010/0252840 A1 | 10/2010 | Ibbetson et al. |
| 2010/0271191 A1 | 10/2010 | de Graff |
| 2010/0279112 A1 | 11/2010 | Kaplan et al. |
| 2010/0283069 A1 | 11/2010 | Rogers et al. |
| 2010/0289124 A1 | 11/2010 | Nuzzo et al. |
| 2010/0298895 A1 | 11/2010 | Ghaffari et al. |
| 2010/0317132 A1 | 12/2010 | Rogers et al. |
| 2010/0321161 A1 | 12/2010 | Isabell |
| 2010/0324455 A1 | 12/2010 | Rangel et al. |
| 2010/0327387 A1 | 12/2010 | Kasai et al. |
| 2011/0011179 A1 | 1/2011 | Gustafsoon et al. |
| 2011/0018838 A1 | 1/2011 | Lee et al. |
| 2011/0034912 A1 | 2/2011 | De Graff et al. |
| 2011/0054583 A1 | 3/2011 | Litt et al. |
| 2011/0068672 A1 | 3/2011 | Hasnain |
| 2011/0121822 A1 | 5/2011 | Parsche |
| 2011/0140897 A1 | 6/2011 | Purks et al. |
| 2011/0147715 A1 | 6/2011 | Rogers et al. |
| 2011/0170225 A1 | 7/2011 | Rogers et al. |
| 2011/0171813 A1 | 7/2011 | Rogers et al. |
| 2011/0184320 A1 | 7/2011 | Shipps |
| 2011/0187798 A1 | 8/2011 | Rogers et al. |
| 2011/0215931 A1 | 9/2011 | Callsen |
| 2011/0218756 A1 | 9/2011 | Callsen |
| 2011/0218757 A1 | 9/2011 | Callsen |
| 2011/0220890 A1 | 9/2011 | Nuzzo |
| 2011/0230747 A1 | 9/2011 | Rogers et al. |
| 2011/0266561 A1 | 11/2011 | Rogers et al. |
| 2011/0277813 A1 | 11/2011 | Rogers |
| 2011/0316120 A1 | 12/2011 | Rogers et al. |
| 2012/0016258 A1 | 1/2012 | Webster et al. |
| 2012/0051005 A1 | 3/2012 | Vanfleteren |
| 2012/0052268 A1 | 3/2012 | Axisa |
| 2012/0065937 A1 | 3/2012 | de Graff |
| 2012/0083099 A1 | 4/2012 | Nuzzo et al. |
| 2012/0087216 A1 | 4/2012 | Keung et al. |
| 2012/0092178 A1 | 4/2012 | Callsen |
| 2012/0092222 A1 | 4/2012 | Kato et al. |
| 2012/0105528 A1 | 5/2012 | Alleyne |
| 2012/0157804 A1 | 6/2012 | Rogers |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0158101 A1 | 6/2012 | Stone et al. |
| 2012/0165759 A1 | 6/2012 | Rogers et al. |
| 2012/0172697 A1 | 7/2012 | Urman |
| 2012/0256308 A1 | 10/2012 | Helin |
| 2012/0261551 A1 | 10/2012 | Rogers |
| 2012/0316455 A1 | 12/2012 | Rahman et al. |
| 2012/0320581 A1 | 12/2012 | Rogers et al. |
| 2012/0327608 A1 | 12/2012 | Rogers |
| 2013/0036928 A1 | 2/2013 | Rogers et al. |
| 2013/0041235 A1 | 2/2013 | Rogers |
| 2013/0100618 A1 | 4/2013 | Rogers |
| 2013/0320503 A1 | 12/2013 | Nuzzo |
| 2014/0140020 A1 | 5/2014 | Rogers |
| 2014/0191236 A1 | 7/2014 | Nuzzo |
| 2014/0216524 A1 | 8/2014 | Rogers |
| 2014/0374872 A1 | 12/2014 | Rogers |
| 2015/0001462 A1 | 1/2015 | Rogers |

FOREIGN PATENT DOCUMENTS

| | | |
|---|---|---|
| CN | 1864095 | 11/2006 |
| CN | 101772348 A | 7/2010 |
| DE | 42 41 045 C1 | 5/1994 |
| DE | 19748173 | 5/1999 |
| EP | 0 929 097 | 7/1999 |
| EP | 1 357 773 | 10/2003 |
| EP | 1 467 224 | 10/2004 |
| EP | 1 477 230 | 11/2004 |
| EP | 1 498 456 | 1/2005 |
| EP | 1 511 096 | 3/2005 |
| EP | 1 558 444 | 8/2005 |
| EP | 1 613 796 | 1/2006 |
| EP | 1 746 869 | 1/2007 |
| EP | 1 773 240 | 4/2007 |
| EP | 1 915 436 | 4/2008 |
| EP | 1 726 329 | 8/2009 |
| EP | 2 086 749 | 8/2009 |
| EP | 2 101 975 | 9/2009 |
| EP | 2 107 964 | 10/2009 |
| EP | 2 109 634 | 10/2009 |
| EP | 2 129 772 | 12/2009 |
| EP | 2 206 017 | 7/2010 |
| EP | 2 211 876 | 8/2010 |
| EP | 2 249 886 | 11/2010 |
| JP | 01-223064 | 9/1989 |
| JP | 2006118441 | 4/1994 |
| JP | 2006-163365 | 6/1994 |
| JP | 09-289332 | 11/1997 |
| JP | 10-500333 | 1/1998 |
| JP | 2011-026344 | 1/1999 |
| JP | 2001332383 | 11/2001 |
| JP | 2002-092984 | 3/2002 |
| JP | 2003-182475 | 7/2003 |
| JP | 2003289136 | 10/2003 |
| JP | 2003297974 | 10/2003 |
| JP | 2004-506470 | 3/2004 |
| JP | 2005-059800 | 3/2005 |
| JP | 2006-044383 | 2/2006 |
| JP | 2006-504450 | 2/2006 |
| JP | 2006-186294 | 7/2006 |
| JP | 2007-515391 | 6/2007 |
| JP | 2008-502739 | 1/2008 |
| JP | 2008-531137 | 8/2008 |
| JP | 2010-508852 | 3/2010 |
| JP | 2010-509593 | 3/2010 |
| JP | 2010-509644 | 3/2010 |
| JP | 2010-509645 | 3/2010 |
| JP | 2010-522583 | 7/2010 |
| JP | 2010-529230 | 8/2010 |
| JP | 2012-505041 | 3/2012 |
| KR | 102007100617 | 10/2007 |
| KR | 10-2008-0069553 | 7/2008 |
| MY | P-020607 | 8/2012 |
| TW | 367570 | 8/1999 |
| TW | 494257 | 7/2002 |
| TW | 200836353 | 9/2008 |
| WO | WO 96/21245 | 7/1996 |
| WO | WO 98/49936 | 11/1998 |
| WO | WO 99/45860 | 9/1999 |
| WO | WO-00/46854 | 8/2000 |
| WO | WO-00/49421 | 8/2000 |
| WO | WO-00/49658 | 8/2000 |
| WO | WO-00/55915 | 9/2000 |
| WO | WO-00/55916 | 9/2000 |
| WO | WO-01/31082 | 5/2001 |
| WO | WO-01/33621 | 5/2001 |
| WO | WO 01/66833 | 9/2001 |
| WO | WO 01/98838 | 12/2001 |
| WO | WO-02/27701 | 4/2002 |

(56) References Cited

FOREIGN PATENT DOCUMENTS

| | | |
|---|---|---|
| WO | WO-02/43032 | 5/2002 |
| WO | WO 02/45160 | 6/2002 |
| WO | WO 02/071137 | 9/2002 |
| WO | WO 02/073699 | 9/2002 |
| WO | WO 02/092778 | 11/2002 |
| WO | WO-02/097708 | 12/2002 |
| WO | WO-02/097724 | 12/2002 |
| WO | WO 03/021679 | 3/2003 |
| WO | WO 03/030194 | 4/2003 |
| WO | WO-03/032240 | 4/2003 |
| WO | WO-03/049201 | 6/2003 |
| WO | WO-03/063211 | 7/2003 |
| WO | WO-03/085700 | 10/2003 |
| WO | WO-03/085701 | 10/2003 |
| WO | WO-03/092073 | 11/2003 |
| WO | WO 04/000915 | 12/2003 |
| WO | WO 04/001103 | 12/2003 |
| WO | WO-2004/003535 | 1/2004 |
| WO | WO-2004/016485 | 2/2004 |
| WO | WO-2004/022637 | 3/2004 |
| WO | WO-2004/022714 | 3/2004 |
| WO | WO-2004/023527 | 3/2004 |
| WO | WO-2004/024407 | 3/2004 |
| WO | WO-2004/027822 | 4/2004 |
| WO | WO-2004/032190 | 4/2004 |
| WO | WO-2004/032191 | 4/2004 |
| WO | WO-2004/032193 | 4/2004 |
| WO | WO-2004/034025 | 4/2004 |
| WO | WO 2004/062697 | 7/2004 |
| WO | WO-2004/086289 | 10/2004 |
| WO | WO-2004/094303 | 11/2004 |
| WO | WO-2004/095536 | 11/2004 |
| WO | WO-2004/099536 | 11/2004 |
| WO | WO-2004/100252 | 11/2004 |
| WO | WO-2004/099068 | 12/2004 |
| WO | WO-2004/105456 | 12/2004 |
| WO | WO 2004/107973 | 12/2004 |
| WO | WO 2005/000483 | 1/2005 |
| WO | WO-2005/005679 | 1/2005 |
| WO | WO 2005/012606 | 2/2005 |
| WO | WO-2005/015480 | 2/2005 |
| WO | WO-2005/017962 | 2/2005 |
| WO | WO-2005/022120 | 3/2005 |
| WO | WO 2005/029578 | 3/2005 |
| WO | WO2005/029578 | 3/2005 |
| WO | WO 2005/033786 | 4/2005 |
| WO | WO 2005/033787 | 4/2005 |
| WO | WO 2005/033789 | 4/2005 |
| WO | WO-2005/054119 | 6/2005 |
| WO | WO 2005/099310 | 10/2005 |
| WO | WO-2005/104756 | 11/2005 |
| WO | WO 2005/106934 | 11/2005 |
| WO | WO 2005/122285 | 12/2005 |
| WO | WO-2005/122285 | 12/2005 |
| WO | WO 2005/123114 | 12/2005 |
| WO | WO 2006/028996 | 3/2006 |
| WO | WO 2006/042287 | 4/2006 |
| WO | WO-2006/069323 | 6/2006 |
| WO | WO 2006/076711 | 7/2006 |
| WO | WO 2006/104069 | 10/2006 |
| WO | WO 2006/130558 | 12/2006 |
| WO | WO-2006/130721 | 12/2006 |
| WO | WO2007/000037 | 1/2007 |
| WO | WO 2007/000037 | 1/2007 |
| WO | WO 2007/016524 | 2/2007 |
| WO | WO 2007/028003 | 3/2007 |
| WO | WO 2007/056183 | 5/2007 |
| WO | WO 2007/116344 | 10/2007 |
| WO | WO-2007/126412 | 11/2007 |
| WO | WO-2008/030666 | 3/2008 |
| WO | WO-2008/030960 | 3/2008 |
| WO | WO-2008/036837 | 3/2008 |
| WO | WO-2008/055054 | 5/2008 |
| WO | WO 2008/085904 | 7/2008 |
| WO | WO 2008/103464 | 8/2008 |
| WO | WO 2008/106485 | 9/2008 |
| WO | WO 2008/108838 | 9/2008 |
| WO | WO 2008/118133 | 10/2008 |
| WO | WO 2008/118211 | 10/2008 |
| WO | WO 2008/127401 | 10/2008 |
| WO | WO 2008/127402 | 10/2008 |
| WO | WO 2008/127403 | 10/2008 |
| WO | WO 2008/127404 | 10/2008 |
| WO | WO 2008/127405 | 10/2008 |
| WO | WO 2008/140562 | 11/2008 |
| WO | WO-2008/143635 | 11/2008 |
| WO | WO 2008/150861 | 12/2008 |
| WO | WO-2009/011709 | 1/2009 |
| WO | WO 2009/023615 | 2/2009 |
| WO | WO 2009/061823 | 5/2009 |
| WO | WO 2009/075625 | 6/2009 |
| WO | WO 2009/076088 | 6/2009 |
| WO | WO 2009/090398 | 7/2009 |
| WO | WO 2009/100280 | 8/2009 |
| WO | WO-2009/111641 | 9/2009 |
| WO | WO 2009/114115 | 9/2009 |
| WO | WO-2009/114689 | 9/2009 |
| WO | WO 2009/118678 | 10/2009 |
| WO | WO 2009/126689 | 10/2009 |
| WO | WO 2009/140588 | 11/2009 |
| WO | WO 2009/155397 | 12/2009 |
| WO | WO-2010/005707 | 1/2010 |
| WO | WO-2010/036807 | 4/2010 |
| WO | WO 2010/036992 | 4/2010 |
| WO | WO 2010/040528 | 4/2010 |
| WO | WO 2010/042798 | 4/2010 |
| WO | WO 2010/046883 | 4/2010 |
| WO | WO 2010/049881 | 5/2010 |
| WO | WO 2010/057142 | 5/2010 |
| WO | WO 2010/065957 | 6/2010 |
| WO | WO 2010/126640 | 11/2010 |
| WO | WO 2010/132552 | 11/2010 |
| WO | WO 2010/132552 A1 | 11/2010 |
| WO | WO 2010/141133 | 12/2010 |
| WO | WO 2011/002931 | 1/2011 |
| WO | WO 2011/003181 A1 | 1/2011 |
| WO | WO 2011/005381 | 1/2011 |
| WO | WO 2011/006133 | 1/2011 |
| WO | WO 2011/008842 | 1/2011 |
| WO | WO 2011/011347 | 1/2011 |
| WO | WO 2011/026101 | 3/2011 |
| WO | WO 2011/038401 | 3/2011 |
| WO | WO 2011/041395 | 4/2011 |
| WO | WO 2011/046652 | 4/2011 |
| WO | WO2011041507 | 4/2011 |
| WO | WO 2011/084450 | 7/2011 |
| WO | WO 2011/084450 A1 | 7/2011 |
| WO | WO 2011/112931 | 9/2011 |
| WO | WO 2011/115643 | 9/2011 |
| WO | WO 2012/097163 | 7/2012 |
| WO | WO 2012/158709 | 11/2012 |
| WO | WO 2012/167096 | 12/2012 |
| WO | WO 2013/010113 | 1/2013 |

OTHER PUBLICATIONS

Adachi et al (1982) "Chemical Etching of InGaAsP/inP DH Wafer," *J. Electrochem. Soc.* 129:1053-1062.

Adachi et al. (1983) "Chemical Etching Characteristics of (001)GaAs," *J. Electrochem. Soc.* 130:2427-2435.

Ahmed et al. (Web Release Oct. 11, 2005) "Extending the 3w-Method to the MHz Range for Thermal Conductivity Measurements of Diamond Thin Films," *Diamond Relat. Mater.* 15(2-3):389-393.

Ahn et al. (2007) "Bendable Integrated Circuits on Plastic Substrates by Use of Printed Ribbons of Single-Crystalline Silicon," *Appl. Phys. Lett.* 90:213501.

Ahn et al. (Dec. 15, 2006) "Heterogeneous Three-Dimensional Electronics by Use of Printed Semiconductor Nanomaterials," *Science* 314:1754-1757.

Ahn et al. (Jun. 2006) "High-Speed Mechanically Flexible Single-Crystal Silicon Thin-Film Transistors on Plastic Substrates," *IEEE Electron Dev. Lett.* 27(6):460-462.

(56) References Cited

OTHER PUBLICATIONS

Alivisatos et al. (1996) "Semiconductor Clusters, Nanocrystals, and Quantum Dots," *Science* 271 :933-937.

Alivisatos et al. (1998) "From Molecules to Materials: Current Trends and Future Directions," *Adv. Mater,* 10:1297-1336.

Allen et al. (Feb. 20, 2006) "Nanomaterial Transfer Using Hot Embossing for Flexible Electronic Devices," *Appl. Phys. Lett.* 88:083112.

Al-Sarawi et al. (Feb. 1998) "A Review of 3-D Packaging Technology," *IEEE Trans. Compo Packag. Manufac. Technol.* B 21(1):2-14.

Amano et al. (Feb. 3, 1986) "Metalorganic Vapor Phase Epitaxial Growth of a High Quality GaN Film Using an Ain Buffer Layer," *Appl. Phys. Lett.* 48(5):353-355.

Ambrosy et al. (1996) "Silicon Motherboards for Multichannel Optical Modules," *IEEE Trans. Compon. Pack. A* 19:34-40.

Andersson et al. (Oct. 16, 2002) "Active Matrix Displays Based on All-Organic Electrochemical Smart Pixels Printed on Paper," *Adv. Mater.* 14:1460-1464.

Ando et al. (2004) "Self-Aligned Self-Assembly Process for Fabricating Organic Thin-Film Transistors," *Appl. Phys. Lett.* 85:1849-1851.

Angadi et al. (Web Release Jun. 1, 2006) "Thermal Transport and Grain Boundary Conductance in Ultrananocrystalline Diamond Thin Films," *J. Appl. Phys.* 99:114301.

Aoki et al. (2003) "Microassembly of Semiconductor Three Dimensional Photonic Crystals," *Nat. Mater.* 2:117-121.

Arnold et al. (Web Release Dec. 28, 2002) "Field-Effect Transistors Based on Single Semiconducting Oxide Nanobelts," *J. Phys. Chem.* B 107(3):659-663.

Ayon et al. (Jan. 1999) "Characterization of a Time Multiplexed Inductively Coupled Plasma Etcher," *J. Electrochem. Soc.* 146(1):339-349.

Baca et al. (2008) "Semiconductor Wires and Ribbons for High-Performance Flexible Electronics," *Angew. Chem. Int. Ed.* 47:5524-5542.

Bachtold et al. (Nov. 9, 2001) "Logic Circuits with Carbon Nanotube Transistors," *Science* 294:1317-1320.

Bae et al. (Jul. 1, 2002) "Single-Crystalline Gallium Nitride Nanobelts," *Appl. Phys. Lett.* 81: 126-128.

Balmer et al. (2005) "Diffusion of Alkanethiols in Pdms and Its Implications on Microcontact Printing (IJCP)," *Langmuir* 21(2):622-632.

Banerjee et al. (May 2001) "3-D ICs: A Novel Chip Design for Improving Deep-Submicrometer Interconnect Performance and Systems-on-Chip Integration," *Proc. IEEE* 89(5):602-633.

Bao et al. (1997) "High-Performance Plastic Transistors Fabricated by Printing Techniques," *Chem. Mater.* 9:1299-1301.

Bao et al. (1999) "Printable Organic and Polymeric Semiconducting Materials and Devices," *J. Mater. Chem.* 9:1895-1904.

Barquins, M. (1992) "Adherence, Friction and Wear of Rubber-Like Materials," *Wear* 158:87-117.

Bates, F.S. (1991) "Polymer-Polymer Phase Behavior," *Science* 251:898-905.

Battaglia et al. (2003) "Colloidal Two-Dimensional Systems: CdSe Quantum Shells and Wells," *Angew. Chem. Int. Ed.* 42:5035-5039.

Bauer et al. (2004) "Biological Applications of High Aspect Ratio Nanoparticles," *J. Mater. Chem.* 14:517-526.

Berg et al. (2003) "Tailored Micropatterns Through Weak Polyelectrolyte Stamping," *Langmuir* 19:2231-2237.

Bernard et al. (1998) "Printing Patterns of Proteins," *Langmuir* 14(9):2225-2229.

Bhunia et al. (2004) "Free-Standing and Vertically Aligned InP Nanowires Grown by Metalorganic Vapor Phase Epitaxy," *Physica E* 21 :583-587.

Bhushan et al. (2004) "Multiwalled Carbon Nanotube AFM Probes for Surface Characterization of Micro/Nanostructures," *Microsyst. Technol.* 10:633-639.

Bietsch et al. (2000) "Conformal Contact and Pattern Stability of Stamps Used for Soft Lithography," *J. Appl. Phys.* 88:4310-4318.

Bishay et al. (2000) "Temperature Coefficient of the Surface Resistivity of Two-Dimensional Island Gold Films," *J. Phys. D. Appl. Phys.* 33(18):2218-2222.

Blanchet et al. (2003) "Large Area, High Resolution, Dry Printing of Conducting Polymers for Organic Electronics," *Appl. Phys. Lett.* 82:463-465.

Blanchet et al. (2003) "Printing Techniques for Plastic Electronics," *J. Imag. Sci. Tech.* 47(4):296-303.

Blazdell et al. (Nov. 1999) "Preparation of Ceramic Inks for Solid Freeforming Using a Continuous Jet Printer," *J. Mat. Syn. Process.* 7(6):349-356.

Boltau et al. (1998) "Surface-Induced Structure Formation of Polymer Blends on Patterned Substrates," *Nature* 391:877-879.

Boncheva et al. (Mar. 15, 2005) "Magnetic Self-Assembly of Three-Dimensional Surfaces from Planar Sheets," *Proc. Natl. Acad. Sci. USA* 102(11):3924-3929.

Boncheva et al. (Mar. 8, 2005) "Templated Self-Assembly: Formation of Folded Structures by Relaxation of Pre-Stressed, Planar Tapes," *Ad. Mater.* 17(5): 553-557.

Bowden et al. (1997) "Self Assembly of Mesoscale Objects into Ordered Two- Dimensional Arrays," *Science* 276:233-235.

Bowden et al. (1998) "Spontaneous Formation of Ordered Structures in Thin Films of Metals Supported on an Elastomeric Polymer," *Nature* 393:146-149.

Bowden et al. (2001) "Molecule-Mimetic Chemistry and Mesoscale Self-Assembly," *Ace. Chem. Res.* 34:231-238.

Bracher et al. (2009) "Shaped Films of Ionotropic Hydrogels Fabricated Using Templates of Patterned Paper," *Adv. Mater.* 21 :445-450.

Braun et al. (1999) "Electrochemically Grown Photonic Crystals," *Nature* 402:603-604.

Britton et al. (Web Release Oct. 25, 2005) "Microstructural Defect Characterization of a Si:H Deposited by Low Temperature HW-CVD on Paper Substrates," *Thin Solid Films* 501(1-2):79-83.

Brown et al. (Dec. 19, 2001) "Heterogeneous Materials Integration: Compliant Substrates to Active Device and Materials Packaging," *Mater. Sci. Eng.* B 87(3):317-322.

Brown, H.R. (1991) "The Adhesion Between Polymers," *Ann. Rev. Mater. Sci.* 21:463-489.

Bruschi et al. (2001) "Micromachined Silicon Suspended Wires With Submicrometric Dimensions," *Microelectron. Eng.* 57-58:959-965.

Buma et al. (2001) "High-Frequency Ultrasound Array Element Using Thermoelastic Expansion in an Elastomeric Film," *Appl. Phys. Lett.* 79:548-550.

Burdinski et al. (2005) "Single Etch Patterning of Stacked Silver and Molybdenum Alloy Layers on Glass Using Microcontact Wave Printing," *J. Am. Chem. Soc.* 127(31):10786-1 0787.

Burdinski, D. (non-dated) "Soft Lithography and Microcontact Wave Printing," http://www.research.philips.com/technologies/light_dev_microsys/softlitho/index.html, Downloaded May 23, 2007.

Burgin et al. (2000) "Large Area Submicrometer Contact Printing Using a Contact Aligner," Langmuir 16:5371-5375.

Burns et al. (2003) "Printing of Polymer Thin-Film Transistors for Active-Matrix-Display Applications," *J. Soc. Int. Display* 11 :599-604.

Campbell et al. (2000) "Fabrication of Photonic Crystals for the Visible Spectrum by Holographic Lithography," *Nature* 404:53-56.

Cao et al. (2006) "Highly Bendable, Transparent Thin-Film Transistors That Use Carbon-Nanotube-Based Conductors and Semiconductors with Elastomeric Dielectrics," *Adv. Mater.* 18(3):304-309.

Cao et al. (Jul. 24, 2008) "Medium-Scale Carbon Nanotube Thin-Film Integrated Circuits on Flexible Plastic Substrates," *Nature* 454:495-500.

Carr et al. (1998) "Measurement of Nanomechanical Resonant Structures in Single-Crystal Silicon," J. Vac. Sci. Technol. B 16:3821-3824.

Chadhury et al. (1991) "Direct Measurement of Interfacial Interactions Between Semispherical Lenses and Flat Sheets of Poly(dimethylsiloxane) and their Chemical Derivatives," Langmuir 7: 1013-1025.

Chang et al. (1994) "Process Techniques, Lithography and Device-Related Physics and Principles," In; GaAs High-Speed Devices: Physics, Technology and Circuit Application, John Wiley and Sons, New York, pp. 115-278.

(56) References Cited

OTHER PUBLICATIONS

Chen et al. (2003) "Characterization of Pd—GaAs Schottky Diodes Prepared by the Electroless Plating Technique," Semiconductor. Sci. Technol. 18:620-626.
Chen et al. (2003) "Electronic Paper: Flexible Active-Matrix Electronic Ink Display," Nature 423: 136.
Chen et al. (2004) "Herringbone Buckling Patterns of Compressed Thin Films on Compliant Substrates," J. Appl. Mech. 71 :597-603.
Chen et al. (2005) "InGaN Nanorings and Nanodots by Selective Area Epitaxy," Appl. Phys. Lett. 87:143111.
Chen et al. (2005) "The Role of Metal-Nanotube Caontact in the Performance of Carbon Nanotube Field-Effect Transistors," Nano Lett. 5(7):1497-1502.
Chen et al. (Feb. 27, 2006) "Complementary Carbon Nanotube-Gated Carbon Nanotube Thin-Fim Transistor," Appl. Phys. Lett. 88:093502.
Chen et al. (Jun. 2002) Effect of Process Parameters on the Surface Morphology and Mechanical Performance of Silicon Structures After Deep Reactive Ion Etching (DRIE) J. Microelectromech. Syst. 11 (3):264-275.
Chen et al. (Mar. 2004) "A Family of Herringbone Patterns in Thin Films," Scr. Mater. 50(6):797-801.
Chen et al. (Mar. 24, 2006) "An Integrated Logic Circuit Assembled on a Single Carbon Nanotube," Science 311:1735.
Cheng et al. (2005) "Ink-Jet Printing, Self-Assembled Polyelectrolytes, and Electroless Plating: Low Cost Fabrication of Circuits on a Flexible Substrate at Room Temperature," Macromol. Rapid Commun. 26:247-264.
Childs et al. (2002) "Decal Transfer Microlithography: A New Soft-Lithographic Patterning Method," J. Am. Chem. Soc. 124:13583-13596.
Childs et al. (2005) "Masterless Soft-Lithography: Patterning UV/Ozone-Induced Adhesion on Poly(dimethylsiloxane) Surfaces," Langmuir 21:10096-10105.
Childs et al. (Aug. 14, 2004) "Patterning of Thin-Film Microstructures on Non-Planar Substrate Surfaces Using Decal Transfer lithography," Adv. Mater. 16(15):1323-1327.
Choi et al. (2007) "Biaxially Stretchable 'Wavy' Silicon Nanomembranes," Nano Lett. 7(6): 1655-1663.
Choi et al. (Web Release Jan. 25, 2005) "Simple Detachment Patterning of Organic Layers and Its Application to Organic light-Emitting Diodes," Adv. Mater. 17(2):166-171.
Chou et al. (2004) "An Orientation-Controlled Pentacene Film Aligned by Photoaligned Polyimide for Organic Thin-Film Transistor Applications," Adv. Func. Mater. 14:811-815.
Chou et al. (Jun. 8, 1999) "Micromachining on (111 )-Oriented Silicon," Sens. Actuators A 75(3):271-277.
Chu et al. (2005) "High-Performance Organic Thin-Film Transistors with Metal Oxide/Metal Bilayer Electrode," Appl. Phys. Lett. 87: 193508.
Chung et al. (2000) "Silicon Nanowire Devices," Appl. Phys. Lett. 76(15):2068-2070.
Chung et al. (Jul. 1, 2003) "A Study on Formation of Al and $Al_2O_3$ on the Porous Paper by DC Magnetron Sputtering," Surf. Coat. Technol. 171(1-3):65-70.
Collins et al. (Apr. 27, 2001) "Engineering Carbon Nanotubes and Nanotube Circuits Using Electrical Breakdown," Science 292:706-709.
Creagh et al. (2003) "Design and Performance of Inkjet Print Heads for Non-Graphic-Arts Applications," MRS Bull. 28:807-811.
Crone et al. (Feb. 3, 2000) "Large-Scale Complementary Integrated Circuits Based on Organic Transistors," Nature 403:521-523.
Crowder et al. (1998) "Low-Temperature Single-Crystal Si TFTs Fabricated on Si Films Processed via Sequential Lateral Solidification," IEEE Electron. Dev. Lett. 19:306-308.
Cui et al. (2001) "Nanowire Nanosensors for Highly Sensitive and Selective Detection of Biological and Chemical Species," Science 293:1289-1292.
Dai et al. (2003) "Novel Nanostructures of Functional Oxides Synthesized by Thermal Evaporation," Adv. Funct. Mater. 13:9-24.

Dai et al. (Web Release Jan. 15, 2002) "Gallium Oxide Nanoribbons and Nanosheets," J. Phys. Chem. B 106(5):902-904.
Davidson et al. (2004) "Supercritical Fluid-liquid-Solid Synthesis of Gallium Arsenide Nanowires Seeded by Alkanethiol-Stabilized Gold Nanocrystals," Adv. Mater. 16:646-649.
de Gans (2004) "Inkjet Printing of Polymers: State of the Art and Future Developments," Adv. Mater. 16(3):203-213.
De Sio et al. (Web Release May 18, 2005) "Electro-Optical Response of a Single-Crystal Diamond Ultraviolet Photoconductor in Transverse Configuration," Appl. Phys. Lett. 86:213504.
DeBoer et al. (2004) "Organic Single-Crystal Field-Effect Transistors," Phys. Stat. Sol. 201 :1302-1331.
Deen et al. (2004) "Electrical Characterization of Polymer-Based FETs Fabricated by Spin-Coating Poly(3-alkylthiophene)s," IEEE Trans. Electron Devices 51: 1892-1901.
Delmarche et al. (1997) "Stability of Molded Polydimethylsiloxane Microstructures," Adv. Mat. 9:741-746.
Deruelle et al. (1995) "Adhesion at the Solid-Elastomer Interface: Influence of Interfacial Chains," Macromol. 28:7419-7428.
Derycke et al. (Sep. 2001) "Carbon Nanotube Inter- and Intramolecular Logic Gates," Nano Lett. 1(9):453-456.
Desai et al. (Feb. 1999) "Nanopore Technology for Biomedical Applications," Biomed. Microdevices 2(1 ):11-40.
Dick et al. (2004) "Synthesis of Branched 'Nanotrees' by Controlled Seeding of Multiples Branching Events," Nat. Mater. 3:380-384.
Dimroth et al. (Mar. 2007) "High-Efficiency Multijunction Solar Cells," MRS Bull. 32:230-235.
Ding et al. (Oct. 4, 2004) "Self Catalysis and Phase Transformation in the Formation of CdSe Nanosaws," Adv. Mater. 16(19):1740-1743.
Dinsmore et al. (2002) "Colloidosomes: Selectively Permeable Capsules Composed of Colloidal Particles," Science 298:1006-1009.
Dinyari et al., (2008) "Curving Monolithic Silicon for Nonplanar Focal Plane Array Applications," Appl Phys Lett, 92:091114.
Divliansky et al. (2003) "Fabrication of Three-Dimensional Polymer Photonic Crystal Structures Using Single Diffraction Element Interference Lithography," Appl. Phys. Lett. 82(11):1667-1669.
Dodabalapur A. (Apr. 2006) "Organic and Polymer Transistors for Electronics," Mater Today 9(4):24-30.
Dodabalapur et al. (1995) "Organic Transistors: Two-Dimensional Transport and Improved Electrical Characteristics," Science 268:270-271.
Duan et al. (2000) "General Synthesis of Compound Semiconductor Nanowires," Adv. Mater. 12:298-302.
Duan et al. (2003) "High-performance Thin-Film Transistors Using Semiconductor Nanowires and Nanoribbons," Nature 425:274-278.
Duan X, (2003) "Semiconductor Nanowires: From Nanoelectronics to Macroelectronics," Abstract from a presentation given at the 11$^{th}$ Foresight Conference on Molecular Nanotechnology, Oct. 10-20, Burlingame, CA.
Duboz et al. (1998) "Transistors and Detectors Based on GaN-Related Materials," In; Group III Nitride Semiconductor Compounds, Gill, B. ed., Clarendon, Oxford, pp. 343-387.
Duffy et al. (1998) "Rapid Prototyping of Microfluidic Systems in Poly(dimethylsiloxane)," Anal. Chem. 70(23):4974-4984.
Durkop et al. (2004) "Extraordinary Mobility in Semiconducting Carbon Nanotubes," Nano Lett. 4(1):35-39.
Eder et al. (Apr. 5, 2004) "Organic Electronics on Paper," Appl. Phys. Lett. 84(14):2673-2675.
Edrington et al. (2001)"Polymer-Based Photonic Crystals," Adv. Mater. 13:421-425.
Efimenko et al. (Oct. 15, 2002) "Surface Modification of Sylgard-184 Poly(dimethyl Siloxane) Networks by Ultraviolet and Ultraviolet/Ozone Treatment," J. Colloid Interface Sci. 254:306-315.
Eftekhari, G. (1993) "Variation in the Effective Richardson Constant of Metal—GaAs and Metal—InP Contacts Due to the Effect of Processing Parameters," Phys. Status Solid (A)-Appl. Res. 140:189-194.
Ensell, G. (1995) "Free Standing Single-Crystal Silicon Microstructures," J. Micromech. Microeng. 5: 1-4.
Examination Report, Corresponding to European Application No. EP 05 756 327.2, Dated Jan. 20, 2010.
Examination Report, Corresponding to Malaysian Patent Application No. PI 20062672, Mailed Aug. 28, 2009.

(56) References Cited

OTHER PUBLICATIONS

Examination Report, Corresponding to Malaysian Patent Application No. PI 20092343, Mailed Jun. 15, 2010.
Examination Report, Corresponding to Malaysian Patent Publication No. PI 20052553, Mailed Mar. 13, 2009.
Examination Report, Corresponding to Singapore Patent Application No. 200608359-6, Completed on Aug. 27, 2008.
Faez et al. (1999) "An Elastomeric Conductor Based on Polyaniline Prepared by Mechanical Mixing," *Polymer* 40:5497-5503.
Feigner et al. (1996) "Flexural Rigidity of Microtubules Measured with the Use of Optical Tweezers," *J. Cell Sci.* 109:509-516.
Fink et al. (1999) "Block Copolymers as Photonic Bandgap Materials," *J. Lightwave Tech.* 17:1963-1969.
Flewitt et al. (2005) "Low-Temperature Deposition of Hydrogenated Amorphous Silicon in an Electron Cyclotron Resonance Reactor for Flexible Displays," *Proc. IEEE* 93: 1364-1373.
Folch et al. (1999) "Wafer-Level In-Registry Microstamping," *J. Microelectromech. Syst.* 8:85-89.
Forment et al. (2004) "Influence of Hydrogen Treatment and Annealing Processes Upon the Schottky Barrier Height of Au/n-GaAs and Ti/n-GaAs Diodes," *Semicond. Sci. Technol.* 19:1391-1396.
Forrest et al. (2004) "The Path to Ubiquitous and Low-Cost Organic Electronic Appliances on Plastic," *Nature* 428:911-918.
Fortunato et al. (2005) "Flexible a-Si: H Position-Sensitive Detectors," *Proc. IEEE* 93:1281-1286.
Fortunato et al. (Sep. 2008) "High-Performance Flexible Hybrid Field-Effect Transistors Based on Cellulose Fiber Paper," *IEEE Electron. Dev. Lett.* 29(9):988-990.
Freire et al. (1999) "Thermal Stability of Polyethylene Terephthalate (PET): Oligomer Distribution and Formation of Volatiles," *Packag. Technol. Sci.* 12:29-36.
Freund, L.B. (2000) "The Mechanics of Electronic Materials," *Int. J. Solids Struct.* 37:185-196.
Friedman et al. (2005) "High-Speed Integrated Nanowire Circuits," *Nature* 434: 1085.
Fu et al. (Jan. 10, 2003) "Patterning of Diamond Microstructures on Si Substrate by Bulk and Surface Micromachining," *J. Mater. Process. Technol.* 132(1-3):73-81.
Furneaux et al. (1989) "The Formation of Controlled-Porosity Membranes from Anodically Oxidized Aluminum," *Nature* 337:147-149.
Gan et al. (2002) "Preparation of Thin-Film Transistors with Chemical Bath Deposited CdSe and CdS Thin Films," *IEEE Trans. Electron. Dev.* 49:15-18.
Gao et al. (Sep. 9, 2005) "Conversion of Zinc Oxide Nanobelts into Superlattice-Structured Nanohelices," *Science* 309: 1700-1704.
Garcia et al. (Oct. 2004) "Etchant Anisotropy Controls the Step Bunching Instability in KOH Etching of Silicon," *Phys. Rev. Lett.* 93(16):166102.
Gamier et al. (1994) "All-Polymer Field-Effect Transistor Realized by Printing Techniques," *Science* 265:1684-1686.
Geim et al. (Mar. 2007) "The Rise of Graphene," *Nature Mater.* 6:183-191.
Geissler et al. (2003) "Fabrication of Metal Nanowires Using Microcontact Printing," *Langmuir* 19(15):6301-6311.
Geissler et al. (Jun. 2003) "Selective Wet-Etching of Microcontact-Printed Cu Substrates with Control Over the Etch Profile," *Microelec. Eng.* 67-68:326-332.
Gelinck et al. (2000) "High-Performance All-Polymer Integrated Circuits," *Appl. Phys. Lett.* 77:1487-1489.
Gelinck et al. (2004) "Flexible Active-Matrix Displays and Shift Registers Based on Solution-Processed Organic Transistors," *Nat. Mater.* 3: 106-110.
Georgakilas et al. (2002) "Wafer-Scale Integration of GaAs Optoelectronic Devices with Standard Si Integrated Circuits Using a Low-Temperature Bonding Procedure," *Appl. Phys. Lett.* 81:5099-5101.
Givargizov, E.I. (1991) "Applications," In; *Oriented Crystallization on Amorphous Substrates*, Plenum Press, New York, pp. 341-363.
Goetting et al. (1999) "Microcontact Printing of Alkanephosphonic Acids on Aluminum: Pattern Transfer by Wet Chemical Etching," *Langmuir* 15:1182-1191.
Goldman et al. (1996) "Correlation of Buffer Strain Relaxation Modes with Transport Properties of Two-Dimensional Electron Gases," *J. Apple. Phys.* 80:6849-6854.
Goldmann et al. (2004) "Hole Mobility in Organic Single Crystals Measured by a "Flip Crystal" Field-Effect Technique," *J. Appl. Phys.* 96:2080-2086.
Gray et al. (2004) "High-Conductivity Elastomeric Electronics," *Adv. Mater.* 16:393-397.
Gruen et al. (Mar. 21, 1994) "Fullerenes as Precursors for Diamond Film Growth Without Hydrogen or Oxygen Additions," *Appl. Phys. Lett.* 65(12):1502-1504.
Gudiksen et al. (Web Release Apr. 18, 2001) "Synthetic Control of the Diameter and Length of Single Crystal Semiconductor Nanowires," *J. Phys. Chem.* B 105:4062-4064.
Guo et al. (Aug. 19, 2002) "Metal-Insulator-Semiconductor Electrostatics of Carbon Nanotubes," *Appl. Phys. Lett.* 81(8):1486-1488.
Gur et al. (2005) "Air-Stable All-Inorganic Nanocrystal Solar Cells Processed from Solution," *Science* 310:462-465.
Gurbuz et al. (Jul. 2005) "Diamond Semiconductor Technology for RF Device Applications." *Solid State Electron.* 49(7): 1055-1070.
Haisma et al. (2002) "Contact Bonding, Including Direct-Bonding in a Historical and Recent Context of Materials Science and Technology, Physics and Chemistry-Historical Review in a Broader Scope and Comparative Outlook," *Mater. Sci. Eng.* R 37:1-60.
Halik et al. (2004) "Low-Voltage Organic Transistors with an Amorphous Molecular Gate Dielectric," *Nature* 431 :963-966.
Hamedi et al. (May 2007) "Towards Woven Logic from Organic Electronic Fibres," *Nat. Mater.* 6:357-362.
Hamilton et al. (2004) "Field-Effect Mobility of Organic Polymer Thin-Film Transistors," *Chem. Mater.* 16:4699-4704.
Han et al. (2005) "Template-Free Directional Growth of Single-Walled Carbon Nanotubes on a- and r-Plane Sapphire," *J. Am. Chem. Soc.* 127:5294-5295.
Harada et al. (2001) "Catalytic Amplification of the Soft Lithographic Patterning of Si. Nonelectrochemical Orthogonal Fabrication of Photoluminescent Porous Si Pixel Arrays," *J. Am. Chem. Soc.* 123:8709-8717.
Harkonen et al. (Jun. 8, 2006) "4 W Single-Transverse Mode VECSEL Utilizing Intra-Cavity Diamond Heat Spreader," *Electron Lett.* 42(12):693-694.
He et al. (2005) "Si Nanowire Bridges in Microtrenches: Integration of Growth into Device Fabrication," *Adv. Mater.* 17:2098-2102.
Hillborg et al. (Web Release Dec. 30, 2003) "Nanoscale Hydrophobic Recovery: Chemical Force Microscopy Study of UV/Ozone-Treated Cross-Linker Poly(dimethylsiloxane)," *Langmuir* 20(3):785-794.
Hines et al. (2005) "Nanotransfer Printing of Organic and Carbon Nanotube Thin-Film Transistors on Plastic Substrates," *Appl. Phys. Lett.* 86:163101.
Holmes et al. (Feb. 25, 2000) "Control of Thickness and Orientation of Solution-Grown Silicon Nanowires," *Science* 287:1471-1473.
Horn et al. (1992) "Contact Electrification and Adhesion Between Dissimilar Materials," *Science* 256:362-364.
Hoyer, P. (1996) "Semiconductor Nanotube Formation by a Two-Step Template Process," *Adv. Mater.* 8:857-859.
Hsia et al. (2005) "Collapse of Stamps for Soft Lithography Due to Interfacial Adhesion," *Appl. Phys. Lett.* 86:154106.
Hsu et al. (2002) "Amorphous Si TFTs on Plastically Deformed Spherical Domes," *J. Non-Crystalline Solids* 299-302: 1355-1359.
Hsu et al. (2003) "Nature of Electrical Contacts in a Metal-Molecule-Semiconductor System," *J. Vac. Sci. Technol.* B 21(4):1928-1935.
Hsu et al. (2004) "Effects of Mechanical Strain on TFTs on Spherical Domes," *IEEE Trans. Electron. Dev.* 51 :371-377.
Hsu et al: (Jan. 15, 2004) "Spherical Deformation of Compliant Substrates with Semiconductor Device Islands," *J. Appl. Phys.* 95(2):705-712.
Hu et al. (1997) "Using Soft Lithography to Fabricate GaAs/AlGaAs Heterostructure Field Effect Transistors," *Appl. Phys. Lett.* 71 :2020-2022.

(56) References Cited

OTHER PUBLICATIONS

Hu et al. (1999) Chemistry and Physics in One Dimension: Synthesis and Properties of Nanowires and Nanotubes, *Acc. Chem. Res.* 32:435-445.
Huang et al. (2001) "Directed Assembly of One-Dimensional Nanostructures into Functional Networks," *Science* 291:630-633.
Huang et al. (2005) "Nanomechanical Architecture of Strained Bilayer Thin Films: From Design Principles to Experimental Fabrication," *Adv. Mater.* 17(23):2860-2864.
Huang et al. (2005) "Nanowires for Integrated Multicolor Nanophotonics," *Small* 1(1):142-147.
Huang et al. (2005) "Nonlinear Analyses of Wrinkles in a Film Bonded to a Compliant Substrate," *J. Mech. Phys. Solids* 53:2101-2118.
Huang et al. (2005) "Stamp Collapse in Soft Lithography," *Langmuir* 21:8058-8068.
Huang et al. (Jan. 16, 2001) "Catalytic Growth of Zinc Oxide Nanowires by Vapor Transport," *Adv. Mater.* 13(2):113-116.
Huck et al. (2000) "Ordering of Spontaneously Formed Buckles on Planar Surfaces," *Langmuir* 16:3497-3501.
Huie, J.C. (2003) "Guided Molecular Self-Assembly: A Review of Recent Efforts," *Smart Mater. Struct.* 12:264-271.
Huitema et al. (2001) "Plastic Transistors in Active-Matrix Displays," *Nature* 414:599.
Hur et al. (2005) "Organic Nanodielectrics for Low Voltage Carbon Nanotube Thin Film Transistors and Complementary Logc Gates," *J. Am. Chem. Soc.* 127:13808-13809.
Hur et al. (Dec. 2004) "Nanotransfer Printing by Use of Noncovalent Surface Forces: Applications to Thin-Film Transistors that Use Single-Walled Carbon Nanotube Networks and Semiconducting Polymers," *Appl. Phys. Lett.* 85(23):5730-5732.
Hur et al. (Jun. 13, 2005) "Extreme Bendability of Single Walled Carbon Nanotube Networks Transferred From High-Temperature Growth Substrates to Plastic and Their Use in Thin-Film Transistors," *Appl. Phys. Lett.* 86:243502.
Hutchinson et al. (1992) "Mixed Mode Cracking in Layered Materials," *Adv. Appl. Mech.* 29:63-191.
Imparato et al. (2005) "Excimer Laser Induced Crystallization of Amorphous Silicon on Flexible Polymer Substrates," *Thin Solid Films* 487:58-62.
International Search Report and Written Opinion, Corresponding to International Application No. PCT/US 07/77759, Mailed Apr. 11, 2008.
International Search Report and Written Opinion, Corresponding to International Application No. PCT/2005/014449, Mailed Jul. 3, 2008.
International Search Report and Written Opinion, Corresponding to International Application No. PCT/US07/22959, Mailed Oct. 14, 2008.
International Search Report and Written Opinion, Corresponding to International Application No. PCT/US2009/036192, Mailed Jul. 6, 2009.
International Search Report anf Written Opinion, Corresponding to International PCT Application No. PCT/US05/19354 Mailed Apr. 18, 2007.
Isberg et al. (Sep. 6, 2002) "High Carrier Mobility in Single-Crystal Plasma-Deposited Diamond," *Science* 297:1670-1672.
Islam et al. (Jan. 16, 2003) "High Weight Fraction Surfactant Solubilization of Single-Wall Carbon Nanotubes in Water," *Nano Lett.* 3(2):269-273.
Ismach et al. (2004) "Atomic-Step-Templated Formation or a Single Wall Carbon Nanotube Patterns," *Angew. Chem. Int. Ed.* 43:6140-6143.
Itoh et al. (1991) "Cathodoluminescence Properties of Undoped and Zn-Doped $Al_xGa_{1-x}N$ Grown by Metaloganic Vapor Phase Epitaxy," *Jap. J. Appl. Phys.* 30: 1604-1608.
Jabbour et al. (2001) "Screen Printing for the Fabrication of Organic Light-Emitting Devices," *IEEE J. Select. Top. Quantum. Electron.* 7(5):769-773.

Jackman et al. (Aug. 4, 1995) "Fabrication of Submicrometer Features on Curved Substrates by Microcontact Printing," *Science* 269:664-666.
Jacobs et al. (2002) "Fabrication of a Cylindrical Display by Patterned Assembly," *Science* 296:323-325.
Jain et al. (2000) "III-Nitrides: Growth, Characterization, and Properties," *J. Appl. Phys*.87:965-1006.
Jain et al. (2005) "Flexible Electronics and Displays: High-Resolution, Roll-to-Roll, Projection Lithography and Photoablation Processing Technologies for High-Throughput Production," *Proc. IEEE* 93:1500-1510.
James et al. (1998) "Patterned Protein Layers on Solid Substrates by Thin Stamp Microcontact Printing," *Langmuir* 14:742-744.
Jang et al. (2006) "Low-Voltage and High-Field-Effect Mobility Organic Transistors with a Polymer Insulator," *Appl. Phys. Lett.* 88:072101.
Javey et al. (2002) "High-K Dielectrics for Advanced Carbon-Nanotube Transistors and Logic Gates," *Nature Mater.* 1:241-246.
Javey et al. (Aug. 7, 2003) "Ballistic Carbon Nanotube Field-Effect Transistors," *Nature* 424:654-657.
Jenkins et al. (1994) "Gallium Arsenide Transistors: Realization Through a Molecularly Designed Insulator," *Science* 263:1751-1753.
Jeon et al. (1995) "Patterning of Dielectric Oxide Thin Layers by Microcontact Printing of Self-Assembled Monolayers," *J. Mater. Res.* 10:2996-2999.
Jeon et al. (2004) "Fabricating Complex Three-Dimensional Nanostructures with High Resolution Conformable Phase Masks," *Proc. Natl. Acad. Sci. USA* 101:12428-12433.
Jeon et al. (Aug. 4, 2004) "Three Dimensional Nanofabrication with Rubber Stamps and Conformable Photomasks," *Adv. Mater.* 16(15):1369-1373.
Jiang et a. (Oct. 2, 2007) "Finite Deformation Mechanics in Buckled Thin Films on Compliant Supports," *Proc. Natl. Acad. Sci. USA* 104(40):15607-15612.
Jiang et al. (1999) "Preparation of Macroporous Metal Films from Colloidal Crystals," *J. Am. Chem. Soc.* 121:7957-7958.
Jiang et al. (2002) "Polymer-on-Polymer Stamping: Universal Approaches to Chemically Patterned Surfaces," *Langmuir* 18:2607-2615.
Jin et al. (2004) "Scalable Interconnection and Integration of Nanowire Devices Without Registration," *Nano Lett.* 4(5):915-919.
Jin et al. (2004) "Soft Lithographic Fabrication of an Image Sensor Array on a Curved Substrate," *J. Vac. Sci. Technol.* B 22(5):2548-2551.
Joachim et al. (Nov. 30, 2000) "Electronics Using Hybrid-Molecular and Mono-Molecular Devices," *Nature* 408:541-548.
Johnson et al. (1999) "Ordered Mesoporous Polymers of Tunable Pore Size from Colloidal Silica Templates," *Science* 283:963-965.
Jones et al. (Jul./Aug. 2004) "Stretchable Wavy Metal Interconnects," *J. Vac. Sci. Technol. A* 22(4):1723-1725.
Joo et al. (2006) "Low-Temperature Solution-Phase Synthesis of Quantum Well Structured CdSe Nanoribbons," *J. Am. Chem. Soc.* 128:5632-5633.
Jortner et al. (2002) "Nanostructured Advanced Materials. Perspectives and Directions," *Pure Appl. Chem.* 74(9):1491-1506.
Kagan (1999) "Organic-Inorganic Hybrid Materials as Semiconducting Channels in Thin-Film Field-Effect Transistors," *Science* 286:945-947.
Kagan et al. (2001) "Patterning Organic-Inorganic Thin-Film Transistors Using Microcontact Printed Templates," *Appl. Phvs. Lett.* 79(21):3536-3538.
Kagan et al. (2003) "Thin Film Transistors—A Historical Perspective," In; *Thin Film Transistors,* Dekker, New York, pp. 1-34.
Kane et al. (2000) "Analog and Digital Circuits Using Organic Thin-Film Transistors on Polyester Substrates," *IEEE Electron. Dev. Lett.* 21(11):534-536.
Kang et al. (2007) "High-Performance Electronics Using Dense, Perfectly Aligned Arrays of Single-Walled Carbon Nanotubes," *Nat. Nanotechnol.* 2:230-236.
Kar et al. (Web Release Feb. 18, 2006) "Shape Selective Growth of CdS One-Dimensional Nanostructures by a Thermal Evaporation Process," *J. Phys. Chem.* B. 110(10):4542-4547.

(56) References Cited

OTHER PUBLICATIONS

Kar et al. (Web Release Feb. 8, 2005) "Controlled Synthesis and Photoluminescence Properties of ZnS Nanowires and Nanoribbons," *J. Phys. Chem.* B 109(8):3298-3302.
Kar et al. (Web Release Sep. 28, 2005) "Synthesis and Optical Properties of CdS Nanoribbons," *J. Phys. Chem* B. 109(41):19134-19138.
Karnik et al. (2003) "Lateral Polysilicon p$^+$-p-n$^+$ and p$^+$-n-n$^+$ Diodes," *Solid-State Electronics* 47:653-659.
Karnik et al. (2003) "Multiple Lateral Polysilicon Diodes as Temperature Sensors for Chemical Microreaction Systems," *Jpn. J. Appl. Phys.* 42:1200-1205.
Kato et al. (2004) The Characteristic Improvement of Si(111) Metal-Oxide-Semiconductor Field-Effect Transistor by Long-Time Hydrogen Annealing, *Jpn. J. Appl. Phys.* 43(10):6848-6853.
Katz et al. (2001) "Synthetic Chemistry for Ultrapure, Processable, and High-Mobility Organic Transistor Semiconductors," *Acc. Chem. Res.* 34:359-369.
Katz, H.E. (2004) "Recent Advances in Semiconductor Performance and Printing Processes for Organic Transistor-Based Electronics," *Chem. Mater.* 16:4748-4756.
Kawata et al. (2001) "Finer Features for Functional Microdevices," *Nature* 412:697-698.
Kendall, D.L. (1979) "Vertical Etching of Silicon at Very High Aspect Ratios," *Ann. Rev. Mater. Sci.* 9:373-403.
Khan et al. (1993) "High Electron Mobility Transistor Based on a GaN-Al$_x$Ga$_{1-x}$N Heterojunction," *Appl. Phys. Lett.* 63:1214-1215.
Khang et al. (2006) "A Stretchable Form of Single-Crystal Silicon for High-Performance Electronics on Rubber Substraights," *Science* 311 :208-212.
Kilby, J.S. (1976) "Invention of the Integrated Circuit," *IEEE Trans. Electron. Dev.* 23(7):648-654.
Kim et al. (2000) "Field Emission from Carbon Nanotubes for Displays," *Diamond and Related Mater.* 9(3-6): 1184-1189.
Kim et al. (2002) "Nanolithography Based on Patterned Metal Transfer and its Application to Organic Electronic Devices," *Appl. Phys. Lett.* 80:4051-4053.
Kim et al. (2003) "Epitaxial self-assembly of block copolymers on lithographically defined nanopatterned substrates," *Nature* 424:411-414.
Kim et al. (2008) "Stretchable and Foldable Silicon Integrated Circuits," *Science* 320:507-511.
Kim et al., (2008) "Complimentary Metal Oxide Silicon Integrated Circuits Incorporating Monolithically Integrated Stretchable Wavy Interconnects," Appl Phys Lett, 93:044102.
Kim et al. (2008) "Materials and Noncoplanar Mesh Designs for Integrated Circuits with Linear Elastic Responses to Extreme Mechanical Deformations," *Proc. Natl. Acad. Sci. USA* 105(48):18675-18680.
Kim et al. (Jan. 2008) "Complementary Logic Gates and Ring Oscillators Plastic on Substrates by Use of Printed Ribbons Single-Crystalline Silicon," *IEEE Electron. Dev. Lett.* 29(1):73-76.
Kim et al. (Nov. 15, 1999) "Direct Observation of Electron Emission Site on Boron-Doped Polycrystalline Diamond Thin Films Using an Ultra-High-Vacuum Scanning Tunneling Microscope," *Appl. Phys. Lett.* 75(20):3219-3221.
Kim et al. (Oct. 2004) "Organic TFT Array on a Paper Substrate," *IEEE Electron. Dev. Lett.* 25(10):702-704.
Kim et al. (Web Release Feb. 29, 2008) "Highly Emissive Self-Assembled Organic Nanoparticles Having Dual Color Capacity for Targeted Immunofluorescence Labeling," *Adv. Mater.* 20(6):1117-1121.
Kim et al. (Web Release Jul. 6, 2009) "Ultrathin Silicon Circuits with Strain-Isolation Layers and Mesh Layouts for High-Performance Electronics on Fabric, Vinyl, Leather and Paper," *Adv. Mater.* 21 (36):3703-3707.
Kim, Y.S. (Web Release Aug. 9, 2005) "Microheater-Integrated Single Gas Sensor Array Chip Fabricated on Flexible Polyimide Substrate," *Sens. Actuators B* 114(1):410-417.
Klauk et al. (2002) "High-Mobility Polymer Gate Dielectric Pentacene Thin Film Transistors," *J. Appl. Phys.* 92:5259-5263.

Klein-Wiele et al. (2003) "Fabrication of Periodic Nanostructures by Phase-Controlled Multiple-Beam Interference," *Appl. Phys. Lett.* 83(23):4707-4709.
Knipp et al. (2003) "Pentacene Thin Film Transistors on Inorganic Dielectrics: Morphology, Structural Properties, and Electronic Transport," *J Appl. Phys.* 93:347-355.
Ko et al. (2006) "Bulk Quantities of Single-Crystal Silicon Micro-/Nanoribbons Generated from Bulk Wafers," *Nano Lett.* 6(10):2318-2324.
Ko et al. (2008) "A Hemispherical Electronic Eye Camera Based on Compressible Silicon Optoelectronics," *Nature* 454:748-753.
Ko et al. (Web Release Oct. 28, 2009) "Curvilinear Electronics Formed Using Silicon Membrane Circuits and Elastomeric Transfer Elements," *Small* 5(23):2703-2709.
Kocabas et al. (2005) "Guided Growth of Large-Scale, Horizontally Aligned Arrays of Single-Walled Carbon Nanotubes and Their Use in Thin-Film Transstors," *Small* 1(11 ): 1110-1116.
Kocabas et al. (2006) "Spatially Selective Guided Growth of High-Coverage Arrays and Random Networks of Single-Walled Carbon Nanotbes and Their Integration into Electronic Devices," *J. Am. Chem. Soc.* 128:4540-4541.
Kocabas et al. (Feb. 5, 2008) "Radio Frequency Analog Electronics Based on Carbon Nanotube Transistors," *Proc. Natl. Acad. Sci. USA* 105(5):1405-1409.
Kodambaka et al. (2006) "Control of Si Nanowire Growth by Oxygen," *Nano Lett.* 6(6):1292-1296.
Koide et al. (2000) "Patterned Luminescence of Organic Light-Emitting Diodes by Hot Microcontact Printing (HμCP) of Self-Assembled Monolayers," *J. Am. Chem. Soc.* 122:11266-11267.
Konagai et al. (1978) "High Efficiency GaAs Thin Film Solar Cells by Peeled Film Technology," *J. Cryst. Growth* 45:277-280.
Kong et al. (2004) "Single-Crystal Nanorings Formed by Epitaxial Self-Coiling of Polar Nanobelts," *Science* 303: 1348-1351.
Kong et al. (Jan. 28, 2000) "Nanotube Molecular Wires as Chemical Sensors," *Science* 287:622-625.
Kong et al. (Oct. 2003) "Structures of Indium Oxide Nanobelts," *Solid State Commun.* 128(1): 1-4.
Kong et al. (Oct. 29, 1998) "Synthesis of Individual Single-Walled Carbon Nanotubes on Patterned Silicon Wafers," *Nature* 395:878-881.
Kudo et al. (Web Release Jun. 13, 2006) "A Flexible and Wearable Glucose Sensor Based on Functional Polymers with Soft-MEMS Techniques," *Biosens. Bioelectron.* 22:558-562.
Kulkarni et al. (2002) "Mesoscale Organization of Metal Nanocrystals," *Pure Appl. Chem* 74(9):1581-1591.
Kumar et al. (1993) "Features of Gold Having Micrometer to Centimeter Dimensions can be Formed Through a Combination of Stamping with an Elastomeric Stamp and an Alkanethiol "Ink" Followed by Chemical Etching," *Appl. Phys. Lett.* 63(14):2002-2004.
Kumar et al. (1994) "Patterning Self-Assembled Monolayers: Applications in Materials Science," *Langmuir* 10:1498-1511.
Kumar et al. (2002) "Thermally-Stable Low-Resistance Ti/Al/Mo/Au Multilayer Ohmic Contacts on $n$-GaN," *J. Appl. Phys.* 92:1712-1714.
Kuo et al. (1985) "Effect of Mismatch Strain on Band Gap in III-V Semiconductors," *J. Appl. Phys.* 57:5428-5432.
Kuykendall et al. (Aug. 2004) "Crystallographic Alignment of High Density Gallium Nitride Nanowire Arrays," *Nat. Mater.* 3:524-528.
Lacour et al. (2003) "Stretchable Gold Conductors on Elastomeric Substrates," *Appl. Phys. Lett.* 82(15):2404-2406.
Lacour et al. (2005) "Stretchable Interconnects for Elastic Electronic Surfaces," *Proc. IEEE* 93(8):1459-1467.
Lacour et al. (Apr. 2004) "Design and Performance of Thin Metal Film Interconnects for Skin-Like Electronic Circuits," *IEEE Electron. Dev. Lett.* 25(4):179-181.
Lacour et al. (Dec. 2004) "An Elastically Stretchable TFT Circuit," *IEEE Electron Dev. Lett.* 25(12):792-794.
Lacour et al. (Web Release Jul. 14, 2006) "Stiff Subcircuit Islands of Diamondlike Carbon for Stretchable Electronics," *J. Appl. Phys.* 100:014913.
Lacour et al. (Web Release May 16, 2006) "Mechanisms of Reversible Stretchability of Thin Metal Films on Elastomeric Substrates," *Appl. Phys. Lett.* 88:204103.

(56) References Cited

OTHER PUBLICATIONS

Laimer et al. (Mar. 1997) "Diamond Growth in a Direct-Current Low-Pressure Supersonic Plasmajet," *Diamond Relat. Mater.* 6:406-410.
Lambacher et al. (2004) "Electrical Imaging of Neuronal Activity by Multi-Transistor-Array (MTA) Recording at 7.8 μm Resolution," *Appl. Phys. A* 79:1607-1611.
Landes et al. (2002) "Some Properties of Spherical and Rod-Shaped Semiconductor and Metal Nanocrystals," *Pure Appl. Chem.* 74(9):1675-1692.
Law et al. (2004) "Semiconductor Nanowires and Nanotubes," *Ann. Rev. Mater. Res.* 34:83-122.
Law et al. (Aug. 27, 2004) "Nanoribbon Waveguides for Subwavelength Photonics Integration," *Science* 305:1269-1273.
Leclercq et al. (1998) "III-V Micromachined Devices for Microsystems," *Microelectronics J.* 29:613-619.
Lecomte et al. (Apr. 2006) "Degradation Mechanism of Diethylene Glycol Units in a Terephthalate Polymer," *Polym. Degrade. Stab.* 91(4):681-689.
Lee et al. (2000) "Thin Film Transistors for Displays on Plastic Substrates," *Solid State Electron.* 44:1431-1434.
Lee et al. (2003) "High-Performance Poly-Si TFTs on Plastic Substrates Using a Nano-Structured Separation Layer Approach," *IEEE Elec. Dev. Lett.* 24: 19-21.
Lee et al. (2004)"Organic Light-Emitting Diodes Formed by Soft Contact Lamination," *Proc. Natl. Acad. Sci. USA* 101(2):429-433.
Lee et al. (2005) "Large-Area, Selective Transfer of Microstructured Silicon: A Printing-Based Approach to High-Performance Thin0Film Transistors Supported on Flexible Substraights," *Adv. Mater.* 17:2332-2336.
Lee et al. (2006) "Micron and Submicron Patterning of Polydimethylsiloxane Resists on Electronic Materials by Decal Transfer Lithography and Reactive Ion-Beam Etching: Application to the Fabrication of High-Mobility, Thin-Film Transistors," *J. Appl. Phys.* 100:084907/1-7.
Lee et al. (Apr. 2005) "Fabrication of Stable Metallic Patterns Embedded in Poly(dimethylsiloxane) and Model Applications in Non-Planar Electronic and Lab-on-a-Chip Device Patterning," *Adv. Funct. Mater.* 15(4):557-566.
Lee et al. (Dec. 1999) "The Surface/Bulk Micromachining (SBM) Process: A New Method for Fabricating Released MEMS in Single Crystal Silicon," *J. Microelectromech. Syst.* 8(4):409-416.
Lee et al. (Feb. 2001) "Application of Carbon Nanotubes to Field Emission Displays," *Diamond and Related Mater.* 10(2):265-270.
Lee et al. (Feb. 2005) "Weave Patterned Organic Transistors on Fiber for E-Textiles," *IEEE Trans. Electron. Dev.* 52(2):269-275.
Li et al. (2002) "High-Resolution Contact Printing with Dendrimers," *Nano Lett.* 2(4):347-349.
Li et al. (2003) "Ultrathin Single-Crystalline-Silicon Cantilever Resonators: Fabrication Technology and Significant Specimen Size Effect on Young's Modulus," *Appl. Phys. Lett.* 83:3081-3083.
Li et al. (2004) "Electrospinning of Nanofibers: Reinventing the Wheel?," *Adv. Mater.* 16(14):1151-1170.
Li et al. (Dec. 2005) "Compliant Thin Film Patterns of Stiff Materials as Platforms for Stretchable Electronics," *J. Mater. Res.* 20(12):3274-3277.
Li et al. (Jul. 1, 2002) "ZnO Nanobelts Grown on Si Substrate," *Appl. Phys. Lett.* 81 (1): 144-146.
Li et al. (Web Release Mar. 16, 2006) "Catalyst-Assisted Formation of Nanocantilever Arrays on ZnS Nanoribbons by Post-Annealing Treatment," *J. Phys. Chem. B* 110(13):6759-6762.
Lieber, C. (2001) "The Incredible Shrinking Circuit," *Sci. Am.* 285(3):58-64.
Lieber, C.M. (2003) "Nanoscale Science and Technology: Building a Big Future from Small Things," *MRS. Bull.* 28:486-491.
Lim et al. (2005) "Flexible Membrane Pressure Sensor," *Sens. Act. A* 119:332-335.
Lima et al. (2007) "Creating Micro- and Nanostructures on Tubular and Spherical Surfaces," *J. Vac. Sci. Technol. B* 25(6):2412-2418.

Lin et al. (2005) "High-Performance Carbon Nanotube Field-Effect Transistor with Tunable Polarities," *IEEE Trans. Nano* 4(5):481-489.
Linder et al. (1994) "Fabrication Technology for Wafer Through-Hole Interconnections and Three-Dimensional Stacks of Chips and Wafers," *Proc. IEEE Micro. Electro Mech. Syst.* 349-354.
Ling et al. (2004) "Thin Film Deposition, Patterning, and Printing in Organic Thin Film Transistors," *Chem. Mater.* 16:4824-4840.
Long et al. (1990) "Heterostructure FETs and Bipolar Transistors," In; *Gallium Arsenide Digital Integrated Circuit Design*, McGraw-Hill, New York, pp. 58-69.
Loo et al. (2002) "Additive, Nanoscale Patterning of Metal Films with a Stamp and a Surface Chemistry Mediated Transfer Process: Applications in Plastic Electronics," *Appl. Physics Lett.* 81 :562-564.
Loo et al. (2002) "High-Resolution Transfer Printing on GaAs Surfaces Using Alkane Dithiol Monolavers," *J. Vac. Sci. Technol. B* 20(6):2853-2856.
Loo et al. (2002) "Interfacial Chemistries for Nanoscale Transfer Printing," *J. Am. Chem. Soc.* 124:7654-7655.
Loo et al. (2002) "Soft, Conformable Electrical Contacts for Organic Semiconductors: High-Resolution Plastic Circuits by Lamination," *Proc. Natl. Acad. Sci. USA* 99(16): 10252-10256.
Loo et al. (2003) "Electrical Contacts to Molecular Layers by Nanotransfer Printing," *Nano Lett.* 3(7):913-917.
Lopes et al. (Sep. 2004) "Thermal Conductivity of PET/(LDPE/Al) Composites Determined by MDSC," *Polym. Test.*23(6):637-643.
Lu et al. (Dec. 2006) "Electronic Materials-Buckling Down for Flexible Electronics," *Nat. Nanotechnol.* 1: 163-164.
Lu et al. (Jul. 19, 2005) "One Dimensional Hole Gas in Germanium/Silicon Nanowire Heterostructures," *Proc. Nat. Acad. Sci. USA* 102(29):10046-10051.
Lu et al. (Nov. 2008) "Nanowire Transistor Performance Limits and Applications," *IEEE Trans Electron Dev.* 55(11 ):2859-2876.
Luan et al. (1992) "An Experimental Study of the Source/Drain Parasitic Resistance Effects in Amorphous Silicon Thin Film Transistors," *J. Appl. Phys.* 72:766-772.
Ma et al. (2004) "Single-Crystal CdSe Nanosaws," *J. Am. Chem. Soc.* 126(3):708-709.
Mack et al. (2006) "Mechanically Flexible Thin-Film Transistors that Use Ultrathin Ribbons of Silicon Derived from Bulk Wafers," *Appl. Phys. Lett.* 88:213101.
Madou, M. (1997) "Etch-Stop Techniques," In; *Fundamentals of Microfabrication*, CRC Press, New York, pp. 193-199.
Maikap et al. (2004) "Mechanically Strained Si NMOSFETs," *IEEE Electron. Dev. Lett.* 25:40-42.
Maldovan et al. (2004) "Diamond-Structured Photonic Crystals," *Nature Materials* 3:593-600.
Mandlik et al. (Aug. 2006) "Fully Elastic Interconnects on Nanopatterned Elastomeric Substrates," *IEEE Electron Dev. Lett.* 27(8):650-652.
Manna et al. (Web Release May 25, 2003) "Controlled Growth of Tetrapod-Branched Inorganic Nanocrystals," *Nat. Mater.* 2:382-385.
Markovich et al. (1999) "Architectonic Quantum Dot Solids," *Ace. Chem. Res.* 32:415-423.
Marquette et al. (2004) "Conducting Elastomer Surface Texturing: A Path to Electrode Spotting Application to the Biochip Production," *Biosens. Bioelectron.* 20:197-203.
Martensson et al. (2004) "Nanowire Arrays Defined by Nanoimprint Lithography," *Nano Lett.* 4:699-702.
Martin, C.R. (1995) "Template Synthesis of Electronically Conductive Polymer Nanostructures," *Ace. Chem. Res.* 28:61-68.
Mas-Torrent et al. (2006) "Large Photoresponsivity in High-Mobility Single-Crystal Organic Field-Effect Phototransistors," *ChemPhysChem* 7:86-88.
Masuda et al. (2000) "Fabrication of Ordered Diamond/Metal Nanocomposite Structures," *Chem. Lett.* 10:1112-1113.
Matsunaga et al. (2003) "An Improved GaAs Device Model for the Simulation of Analog Integrated Circuit," *IEEE Trans. Elect. Dev.* 50:1194-1199.
McAlpine et al. (2003) "High-Performance Nanowire Electronics and Photonics on Glass and Plastic Substrates," *Nano Lett.* 3:1531-1535.

(56) References Cited

OTHER PUBLICATIONS

McAlpine et al. (2005) "High-Performance Nanowire Electronics and Photonics and Nanoscale Patterning on Flexible Plastic Substrates," *Proc. IEEE* 93:1357-1363.

McCaldin et al. (1971) "Diffusivity and Solubility of Si in the Al Metallization of Integrated Circuits," *Appl. Phys. Lett.* 19:524-527.

Meisel et al. (2004) "Three-Dimensional Photonic Crystals by Holographic Lithography Using the Umbrella Configuration: Symmetries and Complete Photonic Band Gaps," *Phys. Rev. B.* 70:165104:1-10.

Meitl et al. (2004) "Solution Casting and Transfer Printing Single-Walled Carbon Nanotube Films," *Nano Lett.* 4(9):1643-1947.

Meitl et al. (2006) "Transfer Printing by Kinetic Control of Adhesion to an Elastomeric Stamp," *Nat. Mater.* 5:33-38.

Meitl et al. (Web Release Feb. 22, 2007) "Stress Focusing for Controlled Fracture in Microelectromechanical Systems," *Appl. Phys. Lett.* 90:083110.

Melosh et al. (2003) "Ultrahigh-Density Nanowire Lattices and Circuits," *Science* 300:112-115.

Menard et al. (2004) "A Printable Form of Silicon for High Performance Thin Film Transistors on Plastic Substrates," *Appl. Phys. Lett.* 84:5398-5400.

Menard et al. (2004) "High-Performance n- and p-Type Single-Crystal Organic Transistors with Free-Space Gate Dielectrics," *Adv. Mat.* 16:2097-2101.

Menard et al. (2004) "Improved Surface Chemistries, Thin Film Deposition Techniques, and Stamp Designs for Nanotransfer Printing," *Langmuir* 20:6871-6878.

Menard et al. (2005) Bendable Single Crystal Silicon Thin Film Transistors Formed by Printing on Plastic Substrates *Appl. Phys. Lett.* 86:093507.

Miao et al. (2003) "Micromachining of Three-Dimensional GaAs Membrane Structures Using High-Energy Nitrogen Implantation," *J. Micromech. Microenq.* 13:35-39.

Michel et al. (2001) Printing Meets Lithography: Soft Approaches to High-Resolution Patterning, *IBM J. Res. Dev.* 45(5):697-719.

Miller et al. (2002) "Direct Printing of Polymer Microstructures on Flat and Spherical Surfaces Using a Letterpress Technique," *J. Vac. Sci. Technol.* B 20(6):2320-2327.

Milliron et al. (2004) "Colloidal Nanocrystal Heterostructures with Linear and Branched Topology," *Nature* 430:190-195.

Min, G. (Apr. 4, 2003) "Plastic Electronics and Their Packaging Technologies," *Syn. Metals.* 135-136:141-143.

Mirkin et al. (Jul. 2001) "Emerging Methods for Micro- and Nanofabrication," *MRS Bull.* 26(7):506-507.

Misewich et al. (May 2, 2003) "Electronically Induced Optical Emission from a Carbon Nanotube FET," *Science* 300:783-786.

Mishra et al. (2002) "AlGaN/GaN HEMTs—an Overview of Device Operation and Applications," *Proc. IEEE* 90:1022-1031.

Mitzi et al. (2004) "High-Mobility Ulltrathin Semiconducting Films Prepared by Spin Coating," *Nature* 428:299-303.

Moon et al. (2002) "Ink-Jet Printing of Binders for Ceramic Components," *J. Am. Ceram. Soc.* 85(4):755-762.

Moore et al. (Sep. 9, 2003) "Individually Suspended Single-Walled Carbon Nanotubes in Various Surfactants," *Nano Lett.* 3(10):1379-1382.

Morales et al. (Jan. 9, 1998) "A Laser Ablation Method for the Synthesis of Crystalline Semiconductor Nanowires," *Science* 279:208-211.

Morent et al. (2007) "Adhesion Enhancement by a Dielectric Barrier Discharge of PDMS used for Flexible and Stretchable Electronics," *J. Phys. D. Appl. Phys.* 40:7392-7401.

Mori et al. (1978) "A New Etching Solution System, $H_3PO_4$-$H_2O_2$-$H_2O$, for GaAs and Its Kinetics," *J. Electrochem. Soc.* 125:1510-1514.

Morkoc et al. (1995) "High-Luminosity Blue and Blue-Green Gallium Nitride Light-Emitting Diodes," *Science* 267:51-55.

Morkved et al. (1994) "Mesoscopic Self-Assembly of Gold Islands on Diblock-Copolymer Films," *Appl. Phys. Lett.* 64:422-424.

Morra et al. (1990) "On the Aging of Oxygen Plasma-Treated Polydimethylsiloxane Surfaces," *J. Colloid Interface Sci.* 137:11-24.

Namazu et al. (2000) "Evaluation of Size Effect on Mechanical Properties of Single Crystal Silicon by Nanoscale Bending Test Using AFM," *J. MEMS* 9:450-459.

Nath et al. (2002) "Nanotubes of the Disulfides of Groups 4 and 5 Metals," *Pure Appl. Chem.* 74(9):1545-1552.

Nathan et al. (2000) "Amorphous Silicon Detector and Thin Film Transistor Technology for Large-Area Imaging of X-Rays," *Microelectron J.* 31 :883-891.

Nathan et al. (2002) "Amorphous Silicon Technology for Large Area Digital X-Ray and Optical Imaging," *Microelectronics Reliability* 42:735-746.

Newman et al. (2004) "Introduction to Organic Thin Film Transistors and Design of n-Channel Organic Semiconductors," *Chem. Mater.* 16:4436-4451.

Nirmal et al. (1999) "Luminescence Photophysics in Semiconductor Nanocrystals," *Acc. Chem. Res.* 32:407-414.

Noda et al. (1996) "New Realization Method for Three-Dimensional Photonic Crystal in Optical Wavelength Region," *Jpn. J. Appl. Phys.* 35:L909-L912.

Nomura et al. (2004) "Room-Temperature Fabrication of Transparent Flexible Thin-Film Transistors Using Amorphous Oxide Semiconductors," *Nature* 432:488-492.

Novoselov et al. (Oct. 22, 2004) "Electric Field Effect in Atomically Thin Carbon Films," *Science* 306:666-669.

O'Connell et al. (Jul. 26, 2002) "Band Gap Fluorescence from Individual Single-Walled Carbon Nanotubes," *Science* 297:593-596.

Odom et al. (2002) "Improved Pattern Transfer in Soft Lithography Using Composite Stamps," *Langmuir* 18:5314-5320.

Office Action Corresponding to Chinese Patent Application No. 200780049982.1, Issued May 12, 2010.

Office Action, Corresponding to Chinese Patent Application No. 200580013574.1, Issued May 11, 2010.

Office Action, Corresponding to Taiwan Patent Application No. 095121212, Issued May 7, 2010.

Office Action, Corresponding to U.S. Appl. No. 11/423,287, Mailed Feb. 13, 2008.

Office Action, Corresponding to U.S. Appl. No. 11/851,182, Mailed Apr. 1, 2010.

Office Action, Corresponding to U.S. Appl. No. 11/981,380, Mailed Sep. 23, 2010.

Office Actions, Corresponding to Chinese Patent Application No. 200580018159.5, Issued Jan. 23, 2009 and Feb. 12, 2010.

Office Actions, Corresponding to U.S. Appl. No. 11/145,542, Mailed between Apr. 5, 2007 and Dec. 23, 2008.

Office Action, Corresponding to U.S. Appl. No. 11/421,654, Mailed Sep. 29, 2009.

Ohzono et al. (2004) "Ordering of Microwrinkle Patterns by Compressive Strain," *Phys. Rev.* B 69(13):132202.

Ohzono et al. (Web Release Jul. 7, 2005) "Geometry-Dependent Stripe Rearrangement Processes Induced by Strain on Preordered Microwrinkle Patterns," *Langmuir* 21(16):7230-7237.

Ong et al. (2004) "High-Performance Semiconducting Poolythiophenes for Organic Thin-Film Transistors," *J. Am. Chem. Soc.* 126:3378-3379.

Ong et al. (2005) "Design of High-Performance Regioreular Polythiophenes for Organic Thin-Film Transistors," *Proc. IEEE* 93:1412-1419.

Origin Energy (May 2004) "Fact Sheet—Sliver Cells," www.oriqinenergY.com.au/sliver.

Ouyang et al. (2008) "High Frequency Properties of Electro-Textiles for Wearable Antenna Applications," *IEEE Trans. Antennas Propaq.* 56(2):381-389.

Ouyang et al. (Web Release Mar. 20, 2000) "Conversion of Some Siloxane Polymers to Silicon Oxide by UV/Ozone Photochemical Processes," *Chem. Mater.* 12(6): 1591-1596.

Pan et al. (2001) "Nanobelts of Semiconducting Oxides," *Science* 291: 1947-1949.

Panev et al. (2003) "Sharp Exciton Emission from Single InAs Quantum Dots in GaAs Nanowires," *Appl. Phys. Lett.* 83:2238-2240.

Pardo et al. (2000) "Application of Screen Printing in the Fabrication of Organic Ligh-Emitting Devices," *Adv. Mater.* 12(17):1249-1252.

Park et al. (1997) "Block Copolymer Lithography: Periodic Arrays of~10 Holes in 1 Square Centimeter," *Science* 276:1401-1404.

(56) References Cited

OTHER PUBLICATIONS

Park et al. (1998) "Fabrication of Three-Dimensional Macroporous Membranes with Assemblies of Microspheres as Templates," *Chem. Mater.* 10:1745-1747.
Patton et al. (Mar. 1998) "Effect of Diamondlike Carbon Coating and Surface Topography on the Performance of Metal Evaporated Magnetic Tapes," *IEEE Trans Magn.* 34(2):575-587.
Paul et al. (Apr. 2003) "Patterning Spherical Surfaces at the Two Hundred Nanometer Scale Using Soft Lithography," *Adv. Func. Mater.* 13(4):259-263.
Pearton et al. (1999) "GaN: Processing, Defects, and Devices," *J. Appl. Phys.* 86:1-78.
Peng et al. (Mar. 2, 2000) "Shape Control of CdSe Nanocrystals," *Nature* 404:59-61.
Piazza et al. (2005) "Protective Diamond-Like Carbon Coatings for Future Optical Storage Disks," *Diamond Relat. Mater.* 14:994-999.
Podzorov et al. (2005) "Hall Effect in the Accumulation Layers on the Surface of Orgaic Semiconductors," *Phys. Rev. lett.* 95:226601.
Pushpa et al. (2002) "Stars and Stripes. Nanoscale Misfit Dislocation Patterns on Surfaces," *Pure Appl. Chem.* 74(9):1663-1671.
Quake et al (2000) "From Micro- to Nanofabrication with Soft Materials," *Science* 290: 1536-1540.
Radtke et al. (Feb. 5, 2007) "Laser-Lithography on Non-Planar Surfaces," *Opt. Exp.* 15(3):1167-1174.
Raman et al. (1989) "Study of Mesa Undercuts Produced in GaAs with $H_3PO_4$-Based Etchants," *J. Electrochem. Soc.* 136:2405-2410.
Razeghi et al. (1994) "High-Power Laser Diodes Based on InGaAsP Alloys," *Nature* 369:631-633.
Razouk et al. (Sep. 1979) "Dependence of Interface State Density on Silicon Thermal Oxidation Process Variables," *J. Electrochem. Soc.* 126(9):1573-1581.
Reuss et al. (2005) "Macroelectronics: Perspectives on Technology and Applications," *Proc. IEEE* 93:1239-1256.
Reuss et al. (Jun. 2006) "Macroelectronics," *MRS Bull.* 31 :447-454.
Ribas et al. (1998) "Bulk Micromachining Characterization of 0.2 μm HEMT MMIC Technology for GaAs MEMS Design," *Mater. Sci. Eng. B* 51 :267-273.
Ridley et al. (1999) "All-Inorganic Field Effect Transistors Fabricated by Printing," *Science* 286:746-749.
Roberts et al. (1979) "Looking at Rubber Adhesion," *Rubber Chem. Technol.* 52:23-42.
Roberts et al. (May 2006) "Elastically Relaxed Free-Standing Strained-Silicon Nanomembranes," *Nat. Mater.* 5:388-393.
Robinson et al. (1983) "GaAs Readied for High-Speed Microcircuits," *Science* 219:275-277.
Roelkens et al. (Dec. 2005) "Integration of InP/InGaAsP Photodetectors onto Silicon-on-Insulator Waveguide Circuits," *Optics Express* 13(25):10102-10108.
Rogers et al. (1997) "Using an Elastomeric Phase Mask for Sub-100 nm Photolithography in the Optical Near Field," *Appl. Phys. Lett.* 70:2658-2660.
Rogers et al. (1998) "Generating~90 Nanometer Features Using Near Field Contact Mode Photolithography with an Elastomeric Phase Mask," *J. Vac. Sci. Technol.* 16(1 ):59-68.
Rogers et al. (1998) "Quantifying Distortions in Soft Lithography," *J. Vac. Sci. Technol. B* 16:88-97.
Rogers et al. (1998) "Using Printing and Molding Techniques to Produce Distributed Feedback and Bragg Reflector Resonators for Plastic Lasers," *Appl. Phys. Lett.* 73: 1766-1768.
Rogers et al. (1999) Printing Process Suitable for Reel-to-Reel Production of High-Performance Organic Transistors and Circuits, *Adv. Mater.* 11 (9):741-745.
Rogers et al. (2000) "Organic Smart Pixels and Complementary Inverter Circuits Formed on Plastic Substrates by Casting and Rubber Stamping," *IEEE Electron Dev. Lett.* 21 (3): 100-103.
Rogers et al. (2001) "Paper-Like Electronic Displays: Large-Area Rubber-Stamped Plastic Sheets of Electronics and Microencapsulated Electrophoretic Inks," *Proc. Nat/. Acad. Sci. USA* 98:4835-4840.
Rogers et al. (2002) "Printed Plastic Electronics and Paperlike Displays," *J. Polym. Sci. Part A. Polym. Chem.* 40:3327-3334.
Rogers, JA (2001) "Rubber Stamping for Plastic Electronics and Fiber Optics," *MRS Bulletin* 26(7):530-534.
Rogers, JA (2001) "Toward Paperlike Displays," *Science* 291: 1502-1503.
Rosenblatt et al. (2002) "High Performance Electrolyte Gated Carbon Nanotube Transistors," *Nano Lett.* 2(8):869-872.
Rotkin et al. (2003) "Universal Description of Channel Conductivity for Nanotube and Nanowire Transistors," *Appl. Phys. Lett.* 83:1623-1625.
Roundy et al. (2003) "Photonic Crystal Structure with Square Symmetry within Each Layer and a Three-Dimensional Band Gap," *Appl. Phys Lett.* 82:3835-3837.
Ruchehoeft et al. (2000) "Optimal Strategy for Controlling Linewidth on Spherical Focal Surface Arrays," *J. Vac. Sci. Technol. B* 18(6):3185-3189.
Samuelson et al. (2004) "Semiconductor Nanowires for Novel One-Dimensional Devices," *Physica E* 21 :560-567.
Sanyal et al. (2002) "Morphology of Nanostructured Materials," *Pure Appl. Chem.* 74(9): 1553-1570.
Sazonov et al. (2005) "Low-Temperature Materials and Thin-Film Transistors for Flexible Electronics," *Proc. IEEE* 93:1420-1428.
Schermer et al. (2005) "Thin-Film GaAs Epitaxial Lift-Off Solar Cells for Space Applications," *Prog. Photovolt. Res. Appl.* 13:587-596.
Schermer et al. (2006) "Photon Confinement in High-Efficiency, Thin Film III-V Solar Cells Obtained by Epitaxial Lift-Off," *Thin Solid Films* 511-512:645-653.
Schmid et al. (2003) "Preparation of Metallic Films on Elastomeric Stamps and Their Application for Contact Processing and Contact Printing," *Adv. Funct. Mater.* 13:145-153.
Schmid et al. (Mar. 25, 2000) "Siloxane Polymers for High-Resolution, High-Accuracy Soft Lithography," *Macromolecules* 33(8):3042-3049.
Schmidt et al. (Mar. 8, 2001) "Thin Solid Films Roll up into Nanotubes," *Nature* 410:168.
Schnable et al. (1969) "Aluminum Metallization—Advantages and Limitations for Integrated Circuit Applications," *IEEE* 57: 1570-1580.
Schneider et al. (2008) "Mechanical Properties of Silicones for MEMS," *J. Micromech. Microeng.* 18:065008.
Schon et al. (1995) "Ambipolar Pentacene Field-Effect Transistors and Inverters," *Science* 287: 1022-1 023.
Schreiber et al. (1998) "The Effectiveness of Silane Adhesion Promotors in the Performance of Polyurethane Adhesives," *J. Adhesion* 68:31-44.
Scorzoni et al. (Oct. 4, 2004) "On the Relationship Between the Temperature Coefficient of Resistance and the Thermal Conductance of Integrated Metal Resistors," *Sens Actuators A* 116( 1): 137-144.
Search and Examination Report, Corresponding to Singapore Patent Application No. 200607372-0, Mailed Oct. 17, 2007.
Search Report, Corresponding to Republic of China (Taiwan) Patent Application No. 094118507, Dated Feb. 24, 2007.
Sekitani et al. (2005) "Bending Experimant on Pentacene Field-Effect Transistors on Plastic Films," *Appl. Phys. Lett.* 86:073511.
Sekitani et al. (Sep. 12, 2008) "A Rubberlike Stretchable Active Matrix Using Elastic Conductors," *Science* 321 :1468-1472.
Sen et al. (2002) "Nonequilibrium Processes for Generating Silicon Nanostructures in Single-Crystalline Silicon," *Pure Appl. Chem.* 74(9):1631-1641.
Serikawa et al. (May 1, 2000) "High-Mobility Poly-Si Thin Film Transistors Fabricated on Stainless-Steel Foils by Low-Temperature Processes Using Sputter-Depositions," *Jpn. J. Appl. Phys.* 39:L393-L395.
Servanti et al. (2005) "Functional Pixel Circuits for Elastic AMOLED displays," *Prac. IEEE* 93:1257-1264.
Service, R.F. (Aug. 15, 2003) "Electronic Textiles Charge Ahead," *Science* 301 :909-911.
Shan et al. (2004) "From Si Source Gas Directly to Positioned, Electrically Contacted Si Nanowires: The Self-Assembling 'Grow-in-Place' Approach," *Nano Lett.* 4(11 ):2085-2089.

(56) References Cited

OTHER PUBLICATIONS

Sharp et al. (2003) "Holographic Photonic Crystals with Diamond Symmetry," *Phys. Rev.* B 68:205102/1-205102/6.
Sheraw et al. (2002) "Organic Thin-Film Transistor-Driven Polymer-Dispersed Liquid Crystal Displays on Felxible Polymeric Substrates," *Appl. Phys. Lett.* 80: 1088-1 090.
Shetty et al. (2005) "Formation and Characterization of Silicon Films on Flexible Polymer Substrates," *Mater. Lett.* 59:872-875.
Shi et al. (Sep. 2000) "Synthesis of Large Areas of Highly Oriented, Very Long Silicon Nanowires," *Adv. Mater.* 12(18):1343-1345.
Shi et al. (Web Release Oct. 11, 2001) "Free-Standing Single Crystal Silicon Nanoribbons," *J. Am. Chem. Soc.* 123(44):11095-11096.
Shtein et al. (Oct. 15, 2004) "Direct Mask-Free Patterning of Molecular Organic Semiconductors Using Organic Vapor Jet Printing," *J. Appl. Phys.* 96(8):4500-4507.
Shull et al. (1998) "Axisymmetric Adhesion Tests of Soft Materials," *Macramol. Chem. Phys.*199:489-511.
Siegel et al. (Web Release Feb. 7, 2007) "Microsolidics: Fabrication of Three-Dimensional Metallic Microstructures in Poly(dimethylsiloxane)," *Adv. Mater.* 19(5):727-733.
Sim et al. (1993) "An Analytical Back-Gate Bias Effect Model for Ultrathin SOI CMOS Devices," *IEEE Trans. Elec. Dev.* 40:755-765.
Sirringhaus et al. (2003) "Inkjet Printing of Functional Materials," *MRS Bull.* 28:802-806.
Sirringhaus et al. (Dec. 15, 2000) "High-Resolution Inkjet Printing of All-Polymer Transistor Circuits," *Science* 290:2123-2126.
Sirringhaus, H. (2005) "Device Physics of Solution-Processed Organic Field-Effect Transistors," *Adv. Mater.* 17:2411-2425.
Smay et al. (2002) "Colloidal Inks for Directed Assembly of 3-D Periodic Structures," *Langmuir* 18:5429-5437.
Smith et al. (2000) "Electric-Field Assisted Assembly and Alignment of Metallic Nanowires," *Appl. Phys. Lett.* 77(9):1399-1401.
Someya et al. (2005) "Conformable, Flexible, Large-Area Networks of Pressure and Thermal Sensors with Organic Transistor Active Matrixes," *Proc. Nat. Acad. Sci. USA* 102:12321-12325.
Someya et al. (2005) "Integration of Organic FETs with Organic Photodiodes for a Large Area, Flexible, and Lightweight Sheet Image Scanners," *IEEE Trans. Electron Devices* 52:2502-2511.
Someya et al. (Jul. 6, 2004) "A Large-Area, Flexible Pressure Sensor Matrix With Organic Field-Effect Transistors for Artificial Skin Applications," *Proc. Nat. Acad. Sci. USA* 101 (27):9966-9970.
Soole et al. (Mar. 1991) "InGaAs Metal-Semiconductor-Metal Photodetectors for Long Wavelength Optical Communications," *IEEE J. Quantum Electron.* 27(3):737-752.
Srinivasan et al. (Web Release Mar. 26, 2007) "Piezoelectric/Ultrananocrystalline Diamond Heterostructures for High-Performance Multifunctional Micro/Nanoelectromechanical Systems," *Appl. Phys. Lett.* 90: 134101-1/134101-3.
Stafford et al. (2004) "A Buckling-Based Metrology for Measuring the Elastic Moduli of Polymeric Thin Films," *Nature Mater.* 3:545-550.
Storm et al. (Web Release Jul. 13, 2003) "Fabrication of Solid-State Nanopores with Single-Nanometre Precision," *Nat. Mater.* 2:537-540.
Strukov et al. (2005) "CMOL FPGA: A Reconfigurable Architecture for Hybrid Digital Circuits with Two-Terminal Nanodevices," *Nanotechnology* 16:888-900.
Sumant et al. (Apr. 2005) "Toward the Ultimate Tribological Interface: Surface Chemistry and Nanotribology of Ultrananocrystalline Diamond," *Adv. Mater.* 17(8):1039-1045.
Sun et al. (2004) "Fabricating Semiconductor Nano/Microwires and Transfer Printing Ordered Arrays of them onto Plastic Substrates," *Nano Lett.* 4: 1953-1959.
Sun et al. (2005) "Advances in Organic Field-Effect Transistors," *J. Mater. Chem.* 15:53-65.
Sun et al. (2005) "Bendable GaAs Metal-Semiconductor Field-Effect Transistors Formed with Printed GaAs Wire Arrays on Plastic Substrates," *Appl. Phys. Lett.* 87:083501.

Sun et al. (2005) "Photolithographic Route to the Fabrication of Micro/Nanowires of III-V Semiconductors," *Adv. Funct. Mater.* 15:30-40.
Sun et al. (Nov. 2006) "Buckled and Wavy Ribbons of GaAs for High-Performance Electronics on Elastomeric Substrates," *Adv. Mater.* 18(21):2857-2862.
Sun et al. (Web Release Dec. 5, 2006) "Controlled Buckling of Semiconductor Nanoribbons for Stretchable Electronics," *Nature Nanotech.* 1:201-207.
Sundar et al. (2004) "Elastomeric Transistor Stamps: Reversible Probing of Charge Transport in Organic Crystals," *Science* 303: 1644-1646.
Suo et al. (Feb. 22, 1999) "Mechanics of Rollable and Foldable Film-on-Foil Electronics," *Appl. Phys. Lett.* 74(8):11771179.
Supplementary European Search Report, Corresponding to European Application No. EP 05 75 6327, Completed Sep. 25, 2009.
Swain et al. (2004) "Curved CCD Detector Devices and Arrays for Multi-Spectral Astrophysical Applications and Terrestrial Stereo Panoramic Cameras," *Proc. SPIE* 5499:281-301.
Sze et al. (1985) *Semiconductor Devices, Physics and Technology*, $2^{nd}$ ed., Wiley, New York, pp. 190-192.
Sze, S. (1985) "Lithography and Etching," In; *Semiconductor Devices: Physics and Technology*, New York: Wiley, pp. 428-467.
Sze, S. (1988) "Ion Implantation," In; *VLSI Technology*, Mcgraw-Hill, 327-374, 568-611.
Sze, S. (1994) "Semiconductor Sensor Technologies," In; *Semiconductor Sensors*, John Wiley and Sons: New York pp. 17-95.
Takamoto et al. (Jan. 20, 1997) "Over 30% Efficient InGaP/GaAs Tandem Solar Cells," *Appl. Phys. Lett.* 70(3):381-383.
Talapin et al. (Oct. 7, 2005) "PbSe Nanocrystal Solids for n- and p-Channel Thin Film Field-Effect Transistors," *Science* 310:86-89.
Tan et al. (Apr. 12, 2004) "Performance Enhancement of InGaN Light Emitting Diodes by Laser-Lift-off and Transfer from Sapphire to Copper Substrate," *Appl. Phys. Lett.* 84(15):2757-2759.
Tanase et al. (2002) "Magnetic Trapping and Self-Assembly of Multicomponent Nanowires," *J. Appl. Phys.* 91 :8549-8551.
Tang et al. (2005) "One-Dimensional Assemblies of Nanoparticles: Preparation, Properties, and Promise," *Adv. Mater.* 17:951-962.
Tao et al. (2003) "Langmuir-Blodgett Silver Nanowire Monolayers for Molecular Sensing Using Surface-Enhanced Raman Spectroscopy," *Nano Lett.* 3:1229-1233.
Tate et al. (2000) "Anodization and Microcontact Printing on Elotroless Silver: Solution-Based Fabrication Procedures for Low-Voltage Electronic Systems with Organic Active Components," *Langmuir* 16:6054-6060.
Teshima et al. (2001) "Room-Temperature Deposition of High-Purity Silicon Oxide Films by RF Plasma-Enhanced CVD," *Surf. Coat. Technol.* 146-147:451-456.
Theiss et al. (1998) "PolySilicon Thin Film Transistors Fabricated at 100° C. on a Flexible Plastic Substrate," *IEDM* 98:257-260.
Toader et al. (2004) "Photonic Band Gap Architectures for Holographic Lithography," *Phy. Rev. Lett* 92(4): 043905/1-043905/4.
Toader et al. (2004) "Photonic Band Gaps Based on Tetragonal Lattices of Slanted Pores," *Phys. Rev. Lett.* 90(23):233901/1-233901/4.
Tong (1999) "Stresses in Bonded Wafers," In; *Semiconductor Wafer Bonding: Science and Technology*, John Wiley; New York, pp. 187-221.
Trau et al. (1997) "Microscopic Patterning of Orientated Mesoscopic Silica Through Guided Growth," *Nature* 390:674-676.
Trentler et al. (1995) "Solution-Liquid-Solid Growth of Crytalline III-V Semiconductors: An Analogy to Vapor-Liquid-Solid Growth," *Science* 270:1791-1794.
Tseng et al. (Web Release Dec. 19, 2003) "Monolithic Integration of Carbon Nanotube Devices with Silicon MOS Technology" *Nano Lett.* 4(1):123-127.
Uchikoga, S. (2002) "Low-Temperature Polycrystalline Silicon Thin-Film Transistor Technologies for System-on-Glass Displays," *MRS Bull.* 27:881-886.
Urruchi et al. (2000) "Etching of DLC Films Using a Low Intensity Oxygen Plasma Jet," *Diamond Relat. Mater.* 9:685-688.

(56) References Cited

OTHER PUBLICATIONS

Vanhollebeke et al. (2000) "Compliant Substrate Technology: Integration of Mismatched Materials for Opto-Electronic Applications," *Prog. Cryst. Growth Charact. Mater.* 41(1-4):1-55.
Velev et al. (1997) "Porous silica via colloidal crystallization," *Nature* 389:447-448.
Vilan et al. (2000) "Molecular Control Over Au/GaAs Diodes," *Nature* 404:166-168.
Vlasov et al. (2001) "On-Chip Natural Assembly of Silicon Photonic Bandgap Crystals," *Nature* 414:289-293.
Voss, D. (2000) "Cheap and Cheerful Circuits," *Nature* 407:442-444.
Wagner et al. (2003) "Silicon for Thin-Film Transistors," *Thin Solid Films* 430: 15-19.
Wagner et al. (2005) "Electronic Skin: Architecture and Components," *Physica E* 25:326-334.
Wagner et al. (Mar. 1, 1964) "Vapor-Liquid-Solid Mechanism of Single Crystal Growth," *Appl. Phys. Lett.* 4(5):89-90.
Wang et al. (2003) "A Solution-Phase, Precursor Route to Polycrystalline $SnO_2$ Nanowores That Can Be Used for Gas Sensing under Ambient Conditions," *J. Am. Chem. Soc.* 125:16176-16177.
Wang et al. (2005) "Oxidation Resistant Germanium Nanowires: Bulk Synthesis, Long Chain Alkanethiol Functionalization, and Langmuir-Blodgett Assembly," *J. Am. Chem. Soc.* 127(33):11871-11875.
Wang et al. (2006) "Direct Synthesis and Characterization of CdS Nanobelts," *Appl. Phys. Lett.* 89:033102.
Weber et al. (Jan. 2004) "A Novel Low-Cost, High Efficiency Micromachined Silicon Solar Cell," *IEEE Electron Device Lett.* 25(1):37-39.
Wen et al. (Web Release Dec. 4, 2004) "Controlled Growth of Large-Area, Uniform, Vertically Aligned Arrays of $\alpha$-$Fe_2O_3$ Nanobelts and Nanowires," *J. Phys. Chem.* B 109(1):215-220.
Whang et al. (2003) "Large-Scale Hierarchical Organization of Nanowire Arrays for Integrated Nanosystems," *Nano Lett.* 3(9):1255-1259.
Williams et al. (Oct. 2006) "Growth and Properties of Nanocrystalline Diamond Films," *Phys. Stat. Sol. A* 203(13):3375-3386.
Williams et al. (Web Release Jan. 23, 2006) "Comparison of the Growth and Properties of Ultranocrystalline Diamond and Nanocrystalline Diamond," *Diamond Relat. Mater.* 15:654-658.
Willner et al. (2002) "Functional Nanoparticle Architectures for Sensoric, Optoelectronic, and Bioelectronic Applications," *Pure Appl. Chem.* 74(9): 1773-1783.
Wind et al. (May 20, 2002) "Vertical Scaling of Carbon Nanotube-Field-Effect Transitors Using Top Gate Electrodes," *Appl. Phys. Lett.* 80(20):3871-3819.
Won et al. (2004) "Effect of Mechanical and Electrical Stresses on the Performance of an a-Si:H TFT on Plastic Substrate," *J. Electrochem. Soc.* 151:G167-G170.
Wu et al. (2001) "Amorphous Silicon Crystallization and Polysilicon Thin Film Transistors on $SiO_2$ Passivated Steel Foil Substrates," *Apple. Surf. Sci* 175-176:753-758.
Wu et al. (2001) "Thermal Oxide of Polycrystalline Silicon on Steel Foil as a Thin-Film Transitor Gate Dielectric," *Appl. Phys. Lett.* 78:3729-3731.
Wu et al. (2002) "Growth of Au-Catalyzed Ordered GaAs Nanowire Arrays by Molecular-Beam Epitaxy," *Appl. Phys. Lett.* 81 :5177-5179.
Wu et al. (2002) "Inorganic Semiconductor Nanowires: Rational Growth, Assembly, and Novel Properties," *Chem. Eur. J.* 8(6):1261-1268.
Wu et al. (2003) "Growth, Branching, and Kinking of Molecular-Beam Epitaxial (110) GaAs Nanowires," *Appl. Phys. Lett.* 83:3368-3370.
Wu et al. (Jul. 1, 2004) "Single-Crystal Metallic Nanowires and Metal/Semiconductor Nanowire Heterostructures," *Nature* 430:61-65.
Wu et al. (Nov. 2002) "Complementary Metal-Oxide-Semiconductor Thin-Film Transistor Circuits from a High-Temperature Polycrystalline Silicon Process on Steel Foil Substrates," *IEEE Trans. Electr. Dev.* 49(11): 1993-2000.
Wu et al. (Web Release Jan. 19, 2002) "Block-by-Block Growth of Single-Crystalline Si/SiGe Superlattice Nanowires," *Nano Lett.* 2(2):83-86.
Wu et al. (Web Release Mar. 13, 2001) "Direct Observation of Vapor-Liquid-Solid Nanowire Growth," *J. Am. Chem. Soc.* 123(13):3165-3166.
Xia et al. (1996) "Shadowed Sputtering of Gold on V-Shaped Microtrenches Etched in Silicon and Applications in Microfabrication," *Adv. Mater.* 8(9):765-768.
Xia (1998) "Soft Lithography" *Angew. Chem. Int. Ed.* 37:551-575.
Xia et al. (1998) "Soft Lithography," *Annu. Rev. Mater. Sci.* 28:153-184.
Xia et al. (1999) "Unconventional Methods for Fabricating and Patterning Nanostructures," *Chem. Rev.* 99: 1823-1848.
Xia et al. (2003) "One-Dimensional Nanostructures: Synthesis, Characterization and Applications," *Adv. Mater.* 15:353-389.
Xia et al. (Jul. 19, 1996) "Complex Optical Surfaces Formed by Replica Molding Against Elastomeric Masters," *Science* 273:347-349.
Xiang et al. (Mar. 25, 2006) "Ge/Si Nanowire Heterostructures as High-Performance Field-Effect Transistors," *Nature* 441 :489-493.
Xie et al. (May 2003) "Polymer-Controlled Growth of $Sb_2Se_3$ Nanoribbons Via a Hydrothermal Process," *J. Cryst. Growth* 252(4):570-574.
Xin et al. (Jun. 2005) "Evaluation of Polydimethylsiloxane Scaffolds with Physiologically-Relevant Elastic Moduli: Interplay of Substrate Mechanics and Surface Chemistry Effects on Vascular Smooth Muscle Cell Response," *Biomaterials* 26(16):3123-3129.
Yang et al. (1997) "Mesoporous Silica with Micrometer-Scale Desgns," *Adv. Mater.* 9:811-814.
Yang et al. (2000) "Stability of Low-Temperature Amorphous Silicon Thin Film Transistors Formed on Glass and Transparent Plastic Substrates," *J. Vac. Sci. Technol.* B 18:683-689.
Yang et al. (2002) "Creating Periodic Three-Dimensional Structures by Multibeam Interface of Visible Laser," *Chem. Mater.* 14:2831-2833.
Yang et al. (Dec. 2007) "RFID Tag and RF Structures on a Paper Substrate Using Inkjet-Printing Technology," *IEEE Trans. Microw. Theory Tech.* 55(12):2894-2901.
Yang, P. (2005) "The Chemistry and Physics of Semiconductor Nanowires," *MRS Bull.* 30:85-91.
Yao et al. (Mar. 2000) "High-Field Effect Electrical Transport in Single-Wall Carbon Nanotubes," *Phys. Rev. Lett.* 84(13):2941-2944.
Yeh et al. (1994) "Fluidic Self-Assembly for the Integration of GaAs Light-Emitting Diodes on Si Substrates," *IEEE Photon. Technol. Lett.* 6:706-708.
Yin et al. (2000) "A Soft lithography Approach to the Fabrication of Nanostructures of Single Crystalline Silicon with Well-Defined Dimensions and Shapes," *Adv. Mater.* 12:1426-1430.
Yin et al. (2005) "Colloidal Nanocrystal Synthesis and the Organic-Inorganic Interface," *Nature* 437:664-670.
Yoon et al. (2005) "Low-Voltage Organic Field-Effect Transistors and Inverters Enabled by Ultrathin Cross-Linked Polymers as Gate Dielectrics," *J. Am. Chem. Soc.* 127: 10388-10395.
Yu et al. (2000) "Silicon Nanowires: Preparation, Device Fabrication, and Transport Properties," *J. Phys. Chem.* B 104(50):11864-11870.
Yu et al. (2003) "Solution-liquid-Solid Growth of Soluble GaAs Nanowires," *Adv. Mater.* 15:416-419.
Yu et al. (2003) "Two- Versus Three-Dimensional Quantum Confinement in Indium Phosphide Wires and Dots," *Nat. Mater.* 2:517-520.
Yuan et al. (2006) "High-Speed Strained-Single-Crystal-Silicon Thin-Film Transistors on Flexible Polymers," *J. Appl. Phys.* 100:013708.
Yurekli et al. (Jul. 24, 2004) "Small-Angle Neutron Scattering from Surfactant-Assisted Aqueous Dispersions of Carbon Nanotubes," *J. Am. Chem. Soc.* 126(32):9902-9903.
Zakhidov et al. (1998) "Carbon Structure with Three-Dimensional Periodicity at Optical Wavelengths," *Science* 282:897-901.

(56) References Cited

OTHER PUBLICATIONS

Zaumseil et al. (2003) "Nanoscale Organic Transistors that use Source/Drain Electrodes Supported by High Resolution Rubber Stamps," *Appl. Phys. Lett.* 82(5):793-795.

Zaumseil et al. (2003) "Three-Dimensional and Multilayer Nanostructures Formed by Nanotransfer Printing," *Nano Lett.* 3(9):1223-1227.

Zhang et al. (2005) "Low-Temperature Growth and Photoluminescence Property of ZnS Nanoribbons," *J. Phys. Chem. B* 109(39):18352-18355.

Zhang et al. (Apr. 2003) "Oxide-Assisted Growth of Semiconducting Nanowires," *Adv. Mater.* 15(7-8):635-640.

Zhang et al. (Apr. 5, 2004) "Structure and Photoluminescence of ZnSe Nanoribbons Grown by Metal Organic Chemical Vapor Deposition," *Appl. Phys. Lett.* 84(14):2641-2643.

Zhang et al. (Feb. 9, 2006) "Electronic Transport in Nanometre-Scale Silicon-on-Insulator Membranes," *Nature* 439:703-706.

Zhang et al. (Jun. 6, 2006) "Anomalous Coiling of SiGe/Si and SiGe/Si/Cr Helical Nanobelts," *Nano Lett.* 6(7):1311-1317.

Zhao et al. (Mar. 2007) "Improved Field Emission Properties from Metal-Coated Diamond Films," *Diamond Relat Mater.* 16(3):650-653.

Zheng et al. (2004) "Shape-and Solder-Directed Self-Assembly to Package Semiconductor Device Segments," *Appl. Phys. Lett.* 85:3635-3637.

Zheng et al. (Aug. 31, 2004) "Sequential Shape-and-Solder-Directed Self Assembly of Functional Microsystems," *Proc. Natl. Acad. Sci. USA* 101(35):12814-12817.

Zhou et al. (2002) "An Efficient Two-Photon-Generated Photoacid Applied to Positive-Tone 3D Microfabrication," *Science* 296:1106-1109.

Zhou et al. (2004) "p-Channel, n-Channel Thin Film Transistors and p-n Diodes Based on Single Wall Carbon Nanotube Networks," *Nano Lett.* 4:2031-2035.

Zhou et al. (2005) "Band Structure, Phonon Scattering, and the Performance Limit of Single-Walled Carbon Nanotube Transistors," *Phys. Rev. Lett.* 95:146805.

Zhou et al. (2005) "Mechanism for Stamp Collapse in Soft Lithography," *Appl. Phys. Lett.* 87:251925.

Zhu et al. (2005) "Spin on Dopants for High-Performance Single-Crystal Silicon Transistors on Flexible Plastic Substrates," *Appl. Phys. Lett.* 86: 133507.

International Search Report and Written Opinion, Corresponding to International Application No. PCT/US2010/027209, Mailed Nov. 11, 2010.

Stella Newsletter IV, Stretchable Electronics for Large Area Applications [online: Apr. 29, 2011] http://www.stella-project.de/Portals/0/Stella_Newsletter_6.pdf.

Notification Concerning Transmittal of International Preliminary Report on Patentability, Corresponding to International Application No. PCT/US2009/059892, mailed Jan. 7, 2011.

International Searching Authority, International Search Report, Corresponding to International Application No. PCT/US2010/051196, mailed Dec. 1, 2010.

International Searching Authority, International Search Report, Corresponding to International Application No. PCT/US2009/067670, mailed Aug. 4, 2010.

International Searching Authority, International Search Report, Corresponding to International Application No. PCT/US2010/020742, mailed Sep. 14, 2010.

International Searching Authority, International Search Report, Corresponding to International Application No. PCT/US2009/065806, mailed Jun. 1, 2010.

International Searching Authority, International Search Report, Corresponding to International Application No. PCT/US2009/059892, mailed Jan. 7, 2010.

International Searching Authority, International Search Report, Corresponding to International Application No. PCT/US2009/064199, mailed May 20, 2010.

Notification Concerning Transmittal of International Preliminary Report on Patentability, Corresponding to International Application No. PCT/US2009/064199, mailed May 17, 2011.

U.S. Appl. No. 12/616,922, filed Nov. 12, 2009.
U.S. Appl. No. 12/636,071, filed Dec. 11, 2009.
U.S. Appl. No. 12/625,444, filed Nov. 24, 2009.
U.S. Appl. No. 12/972,073, filed Dec. 17, 2010.
U.S. Appl. No. 12/976,607, filed Dec. 22, 2010.
U.S. Appl. No. 12/976,814, filed Dec. 22, 2010.
U.S. Appl. No. 12/976,833, filed Dec. 22, 2010.
U.S. Appl. No. 12/686,076, filed Jan. 12, 2010.
U.S. Appl. No. 12/723,475, filed Mar. 12, 2010.
U.S. Appl. No. 13/082,388, filed Apr. 7, 2011.

Notice of Allowance, Corresponding to U.S. Appl. No. 11/423,287, Mailed Jan. 12, 2009.

Office Action, Corresponding to U.S. Appl. No. 11/851,182, Mailed Jun. 7, 2011.

U.S. Appl. No. 11/423,287, filed Jun. 9, 2006.
U.S. Appl. No. 11/851,182, filed Sep. 6, 2007.
U.S. Appl. No. 12/398,811, filed Mar. 5, 2009.
U.S. Appl. No. 11/675,659, filed Feb. 16, 2007 (Abandoned).

International Searching Authority, International Preliminart Report on Patentability, Corresponding to International Application No. PCT/US2009/067670, mailed Jun. 14, 2011.

Rogers, J. (Jul. 9, 2010) "Farewell to Flatland," Science 329:138139.

Search Report and Examination Report Corresponding to Singapore Patent Application No. 200901178-4, completed Mar. 13, 2010.

Search Report Corresponding to Taiwanese Application No. 095121212, completed Oct. 8, 2010.

Someya, T. (Aug. 7, 2008) "Electronic Eyeballs," Nature 454:703-704.

Supplemental European Search Report for European Application 07 84 1968, completed Mar. 31, 2011.

Office Action Corresponding to Chinese Patent Application No. 200780041127.6, issued Apr. 8, 2011.

Office Action Corresponding to European Patent Application No. 05755193.9, issued Jul. 12, 2011.

Notice of Allowance Corresponding to U.S. Appl. No. 12/723,475, Mailed Jul. 8, 2011.

Ahn, H. et al., "Additive Soft Lithographic Patterning of Submicron and Nanometer-Scale Large Area Resists on Electronic Materials," *Nano Letters,* 5, 2533-2537 (2005).

Baca, A.J. et al., "Compact monocrystalline silicon solar modules with high voltage outputs and mechanically flexible designs," *Energy Environ. Sci.,* 2010, 3, 208-211.

Baca, A.J. et al., "Printable single-crystal silicon micro/nanoscale ribbons, platelets and bars generated from bulk wafers," *Adv. Func. Mater.* 17, 3051-3062 (2007).

Bagnall, D.M. et al. "Photovoltaic Technologies," *Energy Policy,* 2008, 36, 4390.

Bergmann, R.B. "Crystalline Si thin-film solar cells: a review," *Appl. Phys. A* 69, 187-194 (1999).

Biancardo, M. et al., "Characterization of microspherical semi-transparent solar cells and modules," *Sol. Energy* 81, 711-716 (2007).

Bossert, R.H. et al., "Thin Film Solar Cells: Technology Evaluation and Perspectives," *ECN,* May 2000.

Brendel, R. "Review of layer transfer processes for crystalline thin-film silicon solar cells," *Jpn. J. Appl. Phys.* 40, 4431-4439 (2001).

Brendel, R. et al., "Ultrathin crystalline silicon solar cells on glass substrates," *Appl. Phys. Lett.* 70, 390-392 (1997).

Burgelman, M. et al. "Modeling Thin-Film PV Devices," *Progress in Photovoltaics* 12, 143-153 (2004).

Cahill, D.G. et al., "Thermal conductivity of epitaxial layers of dilute SiGe alloys," *Phys. Rev. B,* 71:23, 235202-1-4 (2005).

Campbell, P. et al., "Light Trapping Properties of Pyramidally Textured Surfaces," *J. Appl. Phys.* 62, 243-249 (1987).

Clugston, D.A. et al., "Modelling Free-Carrier Absorption in Solar Cells, " *Progress in Phoovoltaics* 5, 229-236 (1997).

Clugston, D.A. et al., "PC1D version 5: 32-bit solar cell modeling on personal computers," *Photovoltaic Specialist Conference,* 1997, Conference Record of the Twenty-Sixth IEEE, 207-210.

(56) References Cited

OTHER PUBLICATIONS

Ebong, A. et al., "Rapid Thermal Processing of High Efficiency N-Type Silicon Solar Cells With Al back Junction," 14th World Conference on Photovoltaic Energy Conversion, Hawaii, USA; May 7-12, 2006.
Feng, N.-N. et al., "Design of Highly Efficient Light-Trapping Structures for Thin-Film Crystalline Silocon Solar Cells," *IEEE Trans. Elect. Dev.* 54, 1926-1933 (2007).
First Office Action dated Mar. 5, 2013 from Chinese Patent Application No. 200980116128.1—includes English translation.
Green, M.A. "Crystalline and thin-film silicon solar cells: state of the art and future potential," *Sol. Energy* 74, 181-192 (2003).
Heine, C. et al., "Submicrometer Gratings for Solar-Energy Applications," *Appl. Opt.* 34, 2476-2482 (1995).
International Search Report and Written Opinion, Corresponding to International Application No. PCT/US12/59131, mailed Apr. 8, 2013.
J. Wang et al., "Binding and Diffusion of a Si Adatom Around the Type-A Step on Si(01) c4x2," *Appl. Phys. Lett.,* 66:15, 1954 (1995).
J. Yoon et al., "Arrays of Monocrystalline Silicon Solar Micro-cells for Modules with Ultra-thin, Mechanically Flexible, Semi-transparent and Micro-optic Concentrator Designs," Materials Research Society (MRS) Symposium P: Photovoltaic Materials and Manufacturing Issues, Fall Meeting, Dec. 3, 2008—Abstract provided.
J. Yoon et al., "Ultrathin silicon solar microcells for semitransparent, mechanically flexible and microconcentrator module designs," *Nat. Mater.,* 2008, 7, 907.
Jeon, S. et al., "Fabricating three dimensional nanostructures using two photon lithography in a single exposure step," *Optics Express,* 14:6, 2300-23208 (2006).
Jeon, S. et al., "Optically fabricated three dimensional nanofluidic mixers for microfluidic systems," *Nano Letters,* 5:7, 1351-1356 (2005).
K. J. Weber et al., "A Novel Silicon Texturization Method Based on Etching Through a Silicon Nitride Mask," *Progress in Photovoltaics: Research and Applications* 13, 691-695 (2005).
Kazmerski, L.L. et al., "Solar photovoltaics R&D at the tipping point: A 2005 technology overview." *J. Elect. Spec. Rel. Phenom.* 150, 105-135 (2006).
Kerschaver, E. V. et al., "Back-contact Solar Cells: A Review," *Prog. Photovolt.* 14, 107-123 (2006).
Kunnavakkam, M.V. et al., "Low-cost, low-loss microlens arrays fabricated by soft-lithography replication process," *Appl. Phys. Lett.* 82, 1152-1154 (2003).
Lee, H.H. et al., "Fabrication of Large Area Stamps, Moulds, and Conformable Photomasks for Soft Lithography," *Journal of Nanoengineering and Nanosystems* 218, 105 (2005).
Lee, K.J. et al., "Bendable GaN High Electron Mobility Transistors on Plastic Substrates," *Journal of Applied Physics* 100, 124507 (2006).
Lei, C. et al., "Grain Boundary Compositions in Cu(InGa)Se$_2$," *J. Appl. Phys.,* 101:2, 24909-1-7 (2007).
Lei, C. et al., "Void formation and surface energies in Cu(InGa)Se$_2$," *J. Appl. Phys.* 100:7, 073518 (2006).
Liao, D. et al., "Cu depletion at the CuInSe$_2$ Surface," *Appl. Phys. Lett.,* 82:17, 2829-2831 (2003).
Liu, Z.X. et al., "A concentrator module of spherical Si solar cell," *Sol. Energy Mater. Sol. Cells* 91, 1805-1810 (2007).
Love, J.C. et al., "Self-Assembled Monolayers of Thiolates on metals as a Form of Nanotechnology," *Chem. Rev.,* 105, 1103-1169 (2005).
M.E. Stewart et al., "Quantitative Multispectral Miosensing and 1-D Imaging Using Quasi-3D Plasmonic Crystals," *Proc. Nat. Acad. Sci.,* 103, 17143-17148 (2006).
Mack, S. et al., "Mechanically flexible thin-film transistors that use ultrathin ribbons of silicon derived from bulk wafers," *Appl. Phys. Lett.,* 88, 213101 (2006).
Malyarchuk, V. et al., "High performance plasmonic crystal sensor formed by soft nanoimprint lithography," *Optics Express,* 13:15, 5669-5675 (2005).

Mercaldo, L.V. et al., Thin film silicon photovoltaics: Architectural perspectives and technological issues, *App. Energy,* 2009, 86, 1836.
Minemoto, T. et al., "Fabrication of spherical silicon crystals by dropping method and their application to solar cells," *Jpn. J. Appl. Phys.* 46, 4016-4020 (2007).
Nelson, B. et al., "Amorphous and Thin-Film Silicon," *NCPV and Solar Program Review,* NREL/CD-520-33586, 583-585, 2003.
Nelson, B. et al., "Project Summary of the NREL Amorphous Silicon Team," *NCPV and Solar Program Review,* NREL/CD-520-33586, 825-828, 2003.
Niggemann, M. et al., Realization of Ultrahigh Photovoltaics with Organic Photovoltaic Nanomodules, *Adv. Mater.* 2008, 20, 4055.
Notice of Allowance corresponding to Korean Patent Application No. 10-20102-7010094, dated Feb. 25, 2013—includes English translation.
Notice of Allowance, U.S. Appl. No. 12/398,811 mailed May 24, 2013.
Notice of Final Rejection for Japanese Patent Application No. 2006-16159, dated Apr. 16, 2013.
Notice of Preliminary Rejection corresponding to Korean Patent Application No. 10-2007-7000216, dated Feb. 21, 2013—includes English translation.
Notice of Preliminary Rejection corresponding to Korean Patent Application No. 10-2012-7030789, dated Feb. 25, 2013—includes English translation.
Office Action, Corresponding to Chinese Patent Application No. 2009801161280.1, mailed Mar. 5, 2013.
Office Action, Corresponding to U.S. Appl. No. 13/441,618, mailed May 23, 2013.
Office Action, Corresponding to U.S. Appl. No. 13/120,486, mailed Apr. 12, 2013.
Orega, P. et al., "High Voltage Photovoltaic Mini-modules," *Progr. Photovolt.: Res. Appl.,* 2008, 16, 369.
Pizzini, S., "Bulk solar grade silicon: how chemistry and physics play to get a benevolent microstructured material," *Appl. Phys. A: Mater. Sci. Process.,* 2009, 96, 171.
R. Rockett et al., "Prediction of dopant ionization energies in silicon: The importance of strain," *Physical Review B,* 6823:23, 3208 (2003).
Rockett, A. "The effect of Na in polycrystalline and single crystal CuIn$_{1-x}$Ga$_x$Se$_2$," *Thin Solid Films,* 480-1, 2-7 (2005).
Rockett, A. et al., "A Monte Carlo simulation of the growth of si(001)2x1: adatom/SA step interactions and growth mechanisms," *Surf. Sci.,* 312, 201 (1994).
Rockett, A. et al., "Near-surface Defect Distributions in Cu(In,Ga)Se$_2$," *Thin Solid Films,* 431-2, 301-306 (2003).
Roedern, B. "Status of Amorphous and Crystalline Thin-Film Silicon Solar Cell Activities," *NCPV and Solar Program Review,* NREL/CD-520-33586, 552-555, 2003.
Ruby, D.S. et al., "Rie-texturing of multicrystalline silicon solar cells," *Solar Energy Materials & Solar Cells* 74, 133-137 (2002).
Sha, A. et al., "Recent progress on microcrystalline solar cells.," *Photovoltaic Specialists Conference, Conference Record of the Twenty-Sixth IEEE,* 569-574 1997).
Sinton, R.A. et al., "27.5-Percent Silicon Concentrator Solar-Cells," *IEEE Elect. Dev. Lett.* 7, 567-569 (1986).
Sobajima et al., "Microstructures of high-growth-rate (up to 8.3 nm/s) microcrystalline silicon photovoltaic layers and their influence on the photovoltaic performance of thin-film solar cells," *J. Non-Cryst. Solids,* 2008, 354, 2407.
Sun, Y. et al., "Gigahertz Operation in Mechanically Flexible Transistors on Plastic Substrates," *Applied Physics Letters* 88, 183509 (2006).
Sun, Y. et al., "Printed Arrays of Aligned GaAs Wires for Flexible Transistors, Diodes and Circuits on Plastic Substrates," *Small* 2(11), 1330-1334 (2006).
Sun, Y. et al., "Top Down Fabrication of Semiconductor Nanowires With Alternating Structures Along Their Transverse and Longitudinal Axes," *Small* 1(11), 1052-1057 (2005).
Taguchi, M. et al., "HIT™ cells—High efficiency crystalline Si cells with novel structure," *Prog. Photovolt.* 8, 503-513 (2000).
Verlinden, P.J. et al., "Silver (R) solar cells: A new thin-crystalline silicon photovoltaic technology," *Sol. Energy Mater. Sol. Cells* 90, 3422-3430 (2006).

(56) References Cited

OTHER PUBLICATIONS

Weber, K.J. et al. "A Novel-Low Cost, High Efficiency Micromachined Silicon Solar Cell," *IEEE Electron Device Letters,* vol. 25, No. 1, 37-39 (2004).
Wenham, S.R. et al., "Buried contact silicon solar cells," *Solar Energy Materials and Solar Cells,*34, 101-110 (1994).
Yamamoto, K. et al., "Thin-film poly-Si solar cells on glass substrate fabricated at low temperature," *Applied Physics A: Materials Science & Processing* 69, 179-185 (1999).
Zhao et al., "24.5% efficiency silicon PERT cells on MCZ substrates and 24.7% efficiency PERL cells on FZ substrates," *Prog. Photovolt.* 7, 471-474 (1999).
Examination Report, Clear Report, Corresponding to Malaysian Patent Application No. PI20062672, issued May 13, 2011.
Examination Report, Corresponding to Malaysian Patent Application No. PI20052553, Issued Feb. 27, 2009.
Examination Report, Corresponding to Malaysian Patent Application No. PI20092343, Issued May 26, 2012.
International Preliminary Report on Patentability for PCT Application PCT/US2010/051196, mailed Apr. 12, 2012.
International Search Report Corresponding to International Application No. PCT/US2011/031648, mailed Dec. 15, 2011.
Notice of Allowance, U.S. Appl. No. 11/851,182, mailed Feb. 16, 2012.
Office Action, Corresponding to U.S. Appl. No. 12/686,076.
Office Action, Corresponding to U.S. Appl. No. 12/636,071, mailed Jun. 6, 2012.
Sweet: Stretchable and Washable Electronics for Embedding Textiles. Available at http://tfcg.elis.ugent.be/projects/sweet. Access Feb. 8, 2012.
Written Opinion of the International Search Authority Corresponding to International patent Application No. PCT/US05/19354 issued Apr. 18, 2007.
International Search Report and Written Opinion Corresponding to International Application No. PCT/US2012/053701 mailed Jan. 15, 2013.
International Search Report and Written Opinion, Corresponding to International Application No. PCT/US2012/039779, mailed Feb. 1, 2013.
International Search Report and Written Opinion corresponding to International Application No. PCT/US2012/058114 mailed Feb. 1, 2013.
Notice of Reasons of Rejection corresponding to Japanese Patent Application No. 2009-527564, mailed Jan. 29, 2013.
Notification of Grant of Patent Right and Notice of Registration corresponding to Chinese Patent App. No. 200780041127.6 issued Dec. 26, 2012.
Office Action for U.S. Appl. No. 13/441,598 mailed Jan. 14, 2013.
Office Action, Corresponding to U.S. Appl. No. 12/778,588 mailed Jan. 8, 2013.
Final Office Action mailed Nov. 21, 2012 corresponding to U.S. Appl. No. 12/921,808.
International Search Report and Written Opinion, Corresponding to International Application No. PCT/US12/46930 mailed Dec. 10, 2012.
Office Action, Corresponding to U.S. Appl. No. 12/398,811 mailed Nov. 26, 2012.
Second Substantive Office Action corresponding to Chinese Patent Application No. 20100519400.5 issued on Oct. 30, 2012.
U.S. Office Action for U.S. Appl. No. 12/405,475 mailed Jun. 8, 2011.
US Office Action for U.S. Appl. No. 11/851,182 mailed Apr. 1, 2010.
US Office Action for U.S. Appl. No. 12/636,071 mailed Jan. 3, 2013.
European Extended Search Report dated Jun. 15, 2012 in Application No. 09716695.3.
Examination and Search Report, Corresponding to Malaysian Patent Application No. PI 20090622, Mailed Sep. 28, 2012.
Notice of Allowance, U.S. Appl. No. 12/686,076, mailed Oct. 5, 2012.
Notice of Allowance, U.S. Appl. No. 12/616,922, mailed Oct. 19, 2012.
Notice of Final Rejection for Japanese Patent Application No. 2007-515549, dated Sep. 19, 2012.
Notice of Reasons for Rejection corresponding to Japanese Patent Application No. P2006-165159, Dispatched Apr. 24, 2012—includes English translation.
Notice of Reasons for Rejection corresponding to Japanese Patent Application No. P2009-546361, Dispatched Jul. 3, 2012—includes English translation.
Examination Report, Corresponding to European Application No. 07 841 968.6.
International Preliminary Report on Patentability for PCT Application No. PCT/US2010/060425, mailed Jun. 28, 2012.
International Search Report and Written Opinion dated Aug. 14, 2012, corresponding to International Patent Application No. PCT/US12/37973.
International Search Report Corresponding to International Application No. PCT/US2012/028590, mailed Jun. 13, 2012.
Notice of Reasons for Rejection corresponding to Japanese Patent Application No. P2008-514820, Dispatched May 8, 2012—includes English translation.
Adrega et al. (2010) "Stretchable Gold Conductors Embedded in PDMS and Patterned by Photolithography: Fabrication and Electromechanical Characterization," J. Micromech. Microeng. 20:055025.
Ago et al. (2005) "Aligned Growth of Isolated Single-Walled Carbon Nanotubes Programmed vby Atomic Arrangement of Substrate Surface," Chem. Phys. Lett. 408:433-438.
Ago et al. (2006) "Synthesis of Horizontally-Aligned Single-Walled Carbon Nanotubes with Controllable Density on Sapphire Surface and Polarized Raman Spectroscopy," Chem. Phys. Lett. 421:399-403.
Al-Halhouli et al. (2008) "Nanoindentation Testing of SU-8 Photoresist Mechanical Properties," Microelectronic Eng. 85:942-944.
Aliot, E. M. et al. (2009) "EHRA/HRS Expert Consensus on Catheter Ablation of Ventricular Arrhythmias: Developed in a partnership with the European Heart Rhythm Association (EHRA), a Registered Branch of the European Society of Cardiology (ESC), and the Heart Rhythm Society (HRS); in collaboration with the American College of Cardiology (ACC) and the American Heart Association (AHA)," Europace 11:771-817.
Altman et al., "Silk-Based Biomaterials," Biomaterials 2003; 24 (3): 24:401-416.
Amir et al. (2000) "The Influence of Helium-Neon Irradiation on the Viability of Skin Flaps in the Rat," Br. J. Plast. Surg. 53:58-62.
Amsden et al. (Nov. 9, 2009) "Spectral Analysis of Induced Color Change on Periodically Nanopatterned Silk Films," Opt. Express 17(23):21271-21279.
Andersen et al. (2004) "Selecting the Signals for a Brain-Machine Interface," Curr. Opin. Neurobiol. 14:720-726.
Ball et al. (2004) "Towards an Implantable Brain-Machine Interface Based on Epicortical Field Potentials," Biomed. Tech. 49:756-759.
Bett et al. (Aug. 1999) "III-V Compounds for Solar Cell Applications," Appl. Phys. A. Mater. Sci. 69(2):119-129.
Bioflex—Biocompatible Flexible Electronic Circuits. Available at http:/tfcg.elis. Ugent.be/projects. Accessed Feb. 8, 2012.
Bourzac, K. (May/Jun. 2010) "TR10: Implantable Electronics," Technology Review, Published by MIT, http://www.technologyreview.com/biomedicine/25086/?a=f.
Bradley et al. (2003) "Flexible Nanotube Electronics," Nano Lett., vol. 3, No. 10, pp. 1353-1355.
Brown et al. (2005) "Evaluation of Polydimethylsiloxane Scaffolds with Physiologically-Relevant Elastic Moduli: Interplay of Substrate Mechanics and Surface Chemistry Effects on Vascular Smooth Muscle Cell Response," Biomaterials 26:3123-3129.
Burge et al. (Jun. 25, 1997) "X-Ray Holography for VLSI Using Synthetic Bilevel Holograms," Proc. Int. Soc. Opt. Eng. 3183:2-13.
Cao et al. (2006) "Bilayer Organic-Inorganic Gate Dielectrics for High-Performance, Low-Voltage, Single-Walled Carbon Nanotube Thin-Film Transistors, Complementary Logic Gates, and p-n Diodes on Plastic Substrates," Adv. Funct. Mater. 16:2355-2362.

(56) References Cited

OTHER PUBLICATIONS

Cao et al. (2006) "Transparent flexible organic thin-film transistors that use printed single-walled carbon nanotube electrodes," Applied Physics Letters 88:113511.
Cao et al. (Jan. 5, 2009) "Ultrathin Films of Single-Walled Carbon Nanotubes for Electronics and Sensors: A Review of Fundamental and Applied Aspects," Adv. Mater. 21(1):29-53.
Chen et al. (Sep. 2004) "Herringbone Buckling Patterns of Compressed Thin Films on Compliant Substrates," J. Appl. Mech. 71:597-603.
Chung et al. (Jul. 1, 2003) "A Study on Formation of Al and Al2O3 on the Porous Paper by DC Magnetron Sputtering," Surf. Coat. Technol. 171(1-3):65-70.
Ciesinski, Michael, "Flexible Electronics: Why the Interest? Where are the Markets? What's Next?" Flextech Alliance Apr. 14, 2010, [retrieved online Apr. 29, 2011] http://www.avsusergroups.org/tfug_pdfs/tfug2010_4ciesinski.pdf.
Clerc, L. (1976) "Directional Differences of Impulse Spread in Trabecular Muscle from Mammalian Heart," J. Physiol. 255:335-346.
Cohen-Karni et al. (2009) "Flexible Electrical Recording from Cells Using Nanowire Transistor Arrays," Proc. Natl. Acad. Sci. USA 106:7309-7313.
Cole et al. (2008) "Patterned Growth and Transfer of ZnO Micro- and Nanocrystals with Size and Location Control," Adv. Mater. 20:1474-1478.
Corazza et al. (2007) "Photobiomodulation on the Angiogenesis of Skin Wounds in Rats Using Different Light Sources," Photomedicine Laser Surg. 25:102-106.
Cox, H. L. (1952) "The Elasticity and Strength of Paper and Other Fibrous Materials," Br. J. Appl. Phys. 3:72-79.
Dai et al. (2002) "Gallium Oxide Nanoribbons and Nanosheets," J. Phys. Chem. B 106(5):902-904.
Duesberg et al. (2000) "Polarized Raman Spectroscopy on Isolated Single-Wall Carbon Nanotubes," Phys. Rev. Lett., vol. 85, No. 25, pp. 5436-5439.
Dupuis et al. (2008) "History, Development, and Applications of High-Brightness Visible Light-Emitting Diodes," IEEE J. Lightwave Tech. 26:1154-1171.
European Extended Search Report dated Feb. 9, 2012 in Application No. 09826745.3.
Final Office Action, Corresponding to U.S. Appl. No. 11/851,182, Mailed Oct. 29, 2010.
Freeman et al. (2000) "Spatial Spectral Analysis of Human Electrocardiograms Including the Alpha and Gamma Bands," J. Neurosci. Methods 95:111-121.
Gardner et al. (1965) "Physical Aspects of the Internal Water Relations of Plant Leaves," Plant Physiol. 40:705-710.
Goldsmith, T.H. (Sep. 1990) "Optimization, Constraint, and History in the Evolution of Eyes," *Quart. Rev. Biol.* 65(3):281-322.
Gratz et al. (1991) "Atomic Force Microscopy of Atomic-Scale Ledges and Etch Pits Formed During Dissolution of Quartz," Science, 251:1343-1346.
Gray et al. (2004) "High-Conductivity Elastomeric Electronics," *Adv. Mater.* 16:393 397.
Gray et al. (Dec. 2001) "Screen Printed Organic Thin Film Transistors (OTFTs) on a Flexible Substrate," *Proc. SPIE* 4466:89-94.
Grayson, T. (2002) "Curved Focal Plane Wide Field of View Telescope Design," *Proc. SPIE* 4849:269-274.
Hayase et al. (2001) "Photoangioplasty with Local Motexafln Lutetium Delivery Reduces Macrophages in a Rabbit Post-Balloon Injury Model," Cardiovascular Res. 49:449-455.
Heffelfinger et al. (1997) "Steps and the structure of the (0001) α-alumina surface," Surf. Sci., 370:L168-L172.
Hollenberg et al. (2006) "A MEMS Fabricated Flexible Electrode Array for Recording Surface Field Potentials," J. Neurosci. Methods 153:147-153.
Horan et al. (Jun. 2005) "In Vitro Degradation of Silk Fibroin," Biomaterials 26(17):3385-3393.
Hsu et al. (Mar. 2004) "Effects of Mechanical Strain on TFT's on Spherical Domes," IEEE Trans. Electron Dev. 51(3):371-377.
Hu et al. (2004) "Percolation in Transparent and Conducting Carbon Nanotube Networks," Nano Lett., vol. 4, No. 12, pp. 2513-2517.
Hu et al. (2009) "Highly Conductive Paper for Energy-Storage Devices," Proc. Natl. Acad. Sci. USA 106:21490-21494.
Hu et al. (2010) "Stretchable, Porous, and Conductive Energy Textiles," Nano Lett. 10:708-714.
Huang et al. (2001) "Room-Temperature Ultraviolet Nanowire Nanolasers," Science 292:1897-1899.
Huang et al. (2003) "Growth of Millimeter-Long and Horizontally Aligned Single-Walled Carbon Nanotubes on Flat Substrates," J. Am. Chem. Soc., 125:5636-5637.
Huang et al. (2004) "Long and Oriented Single-Walled Carbon Nanotubes Grown by Ethanol Chemical Vapor Deposition," J. Phys. Chem. B. 108:16451-16456.
Huang et al. (2004) "Self-Organizing High-Density Single-Walled Carbon Nanotube Arrays from Surfactant Suspensions," Nanotechnol. 15:1450-1454.
Hur et al. (2005) "Printed thin-film transistors and complementary logic gates that use polymer-coated single-walled carbon nanotube networks," J. Appl. Phys., 98, 114302.
International Search Report and Written Opinion, Corresponding to International Application No. PCT/US10/50468, Mailed Jan. 6, 2011.
International Search Report and Written Opinion, Corresponding to International Application No. PCT/US07/74293, Mailed Jul. 24, 2008.
International Search Report and Written Opinion, Corresponding to International Application No. PCT/US07/77217, Mailed Jun. 3, 2008.
International Search Report and Written Opinion, Corresponding to International Application No. PCT/US07/82633, Mailed May 16, 2008.
International Search Report and Written Opinion, Corresponding to International Application No. PCT/US09/47442, Mailed Sep. 21, 2009.
International Search Report and Written Opinion, Corresponding to International Application No. PCT/US2006/032125, Mailed Mar. 21, 2008.
International Search Report and Written Opinion, Corresponding to International Application No. PCT/US2009/058231, Mailed Nov. 17, 2009.
International Search Report and Written Opinion, Corresponding to International Application No. PCT/US2010/034520, Mailed Sep. 24, 2010.
International Search Report and Written Opinion, Corresponding to International Application No. PCT/US2010/042585, Mailed May 25, 2011.
International Search Report and Written Opinion, Corresponding to International Application No. PCT/US2011/028094, Mailed Jul. 14, 2011.
International Search Report and Written Opinion, Corresponding to International PCT Application No. PCT/US2006/021161, Mailed Feb. 28, 2008.
International Search Report and Written Opinion, Corresponding to International PCT Application No. PCT/US2007/077759, Mailed Apr. 11, 2008.
International Search Report and Written Opinion, Corresponding to International PCT Application No. PCT/US2007/079070, Mailed Apr. 23, 2008.
International Search Report and Written Opinion, Corresponding to International PCT US2010/061151.
International Search Report Corresponding to International Application No. PCT/US2009/036956, mailed Jun. 29, 2009.
Jacobs et al. (2001) "Submicrometer Patterning of Charge in Thin-Film Electrets," Science 291:1763-1766.
Jang et al. (2003) "Lateral Growth of Aligned Multiwalled Carbon Nanotubes Under Electric Fiels," Solid State Commun. 126:305-308.
Javey et al. (2005) "High Performance n-Type Carbon Nanotube Field-Effect Transistors with Chemically Doped Contacts," Nano Lett., vol. 5, No. 2, pp. 345-348.

(56) References Cited

OTHER PUBLICATIONS

Jeon et al. (2003) "Structural and Mechanical Properties of Woven Fabrics Employing Peirce's Model," Textile Res. J. 73:929-933.
Jeon et al. (2004) "Three Dimensional Nanofabrication with A rubber Stamps and Conformable Photomasks," Adv. Mater. 16:593-600.
Jiang et al. (2007) "Mechanical Properties of Robust Ultrathin Silk Fibroin Films," Adv. Funct. Mater. 17:2229-2237.
Jin et al. (Aug. 2005) "Water-Stable Silk Films with Reduced α-Sheet Content," Adv. Funct. Mater. 15(8):1241-1247.
Jin et al. (Web Release Jan. 23, 2004) "Biomaterial Films of Bombyx mori Silk Fibroin with Poly(ethylene oxide)," Biomacromolecules 5(3):711-717.
Jiyun, C.H. (2003) "Guided Molecular Self-Assembly: A Review of Recent Efforts," Smart Mater. Struct. 12:264-271.
Joselevich (2002) "Vectorial Growth of Metallic and Semiconducting Single-Wall Carbon Nanotubes," Nano Lett., vol. 2, No. 10, pp. 1137-1141.
Kadish et al. (1988) "Interaction of Fiber Orientation and Direction of Impulse Propagation with Anatomic Barriers in Anisotropic Canine Myocardium," Circulation. 78:1478-1494.
Kang et al. (2007) "Printed Multilayer Superstructures of Aligned Single-Walled Carbon Nanotubes for Electronic Applications," Nano Lett. 7(11):3343-3348.
Kellis et al. (2009) "Human Neocortical Electrical Activity Recorded on Nonpenetrating Microwire Arrays: Applicability for Neuroprostheses," Neurosurg. Focus 27(1):E9.
Khakani et al. (2006) "Lateral Growth of Single Wall Carbon Nanotubes on Various Substrates by Means of an 'All-Laser' Synthesis Approach," Diamond Relat. Mater. 15:1064-1069.
Kim et al. (2008) "Stretchable Electronics: Materials Strategies and Devices," Adv. Mater.20:4887-4892.
Kim et al. (2009) "Integrated Wireless Neural Interface Based on the Utah Electrode array," Biomed. Microdevices 11:453-466.
Kim et al. (2009) "Optimized Structural Designs for Stretchable Silicon Integrated Circuits," Small 5(24):2841-2847.
Kim et al. (Dec. 2, 2008) "Materials and Noncoplanar Mesh Designs for Integrated Circuits with Linear Elastic Responses to Extreme Mechanical Deformations," Proc. Natl. Acad. Sci. USA 105(48):18675-18680
Kim et al. (Oct. 17, 2010) "Waterproof AlInGaP optoelectronics on stretchable substrates with applications in biomedicine and robotics," Nature Materials 9:929-937.
Kim et al. (Web Release Apr. 18, 2010) "Dissolvable Films of Silk Fibroin for Ultrathin Conformal Bio-Integrated Electronics," Nature Materials 9:511-517.
Kim et al. (Web Release Jul. 31, 2008) "Complementary Metal Oxide Silicon Integrated Circuits Incorporating Monolithically Integrated Stretchable Wavy Interconnects," Appl. Phys. Lett. 93(4):044102.
Kim et al. (Web Release Sep. 29, 2009) "Silicon Electronics on Silk as a Path to Bioresorbable, Implantable Devices," Appl. Phys. Lett. 95:133701-133703.
Ko et al. (2010) "Flexible Carbon Nanofiber Connectors with Anisotropic Adhesion Properties," Small 6:22-26.
Kocabas et al. (2004) "Aligned Arrays of Single-Walled Carbon Nanotubes Generated from Random Networks by Orientationally Selective Laser Ablation," Nano Lett., vol. 4, No. 12, pp. 2421-2426.
Kocabas et al. (2006) "Large Area Aligned Arrays of SWNTs for High Performance Thin Film Transistors," American Physical Society, APS March Meeting, Mar. 13-17, Abstract # W31.004.
Kocabas et al. (2007) "Experimental and Theoretical Studies of Transport Through Large Scale, Partially Aligned Arrays of Single-Walled Carbon Nanotubes ni Thin Film Type Transistors," Nano Lett. 7(5)1195-1202.
Kumar et al. (2005) "Percolating in Finite Nanotube Networks," Phys. Rev. Lett., 95, 066802.
Lacour et al. (2010) "Flexible and Stretchable Micro-Electrodes for in Vitro and n Vivo Neural Interfaces," Med. Biol. Eng. Comput. 48:945-954.
Lawrence et al. (2008) "Bioactive Silk Protein Biomaterial Systems for Optical Devices," Biomacromolecules 9:1214-1220.
Lay et al. (2004) "Simple Route to Large-Scale Ordered Arrays of Liquid-Deposited Carbon Nanotubes," Nano Lett., vol. 4, No. 4, pp. 603-606.
Lee et al. (2005) "A Printable Form of Single-Crystalline Gallium Nitride for Flexable Optoelectronic Systems," Small 1:1164-1168.
Leong et al. (2009) "Tetherless Thermobiochemicall Actuated Microgrippers," Proc. Natl. Acad. Sci. USA 106:703-709.
Létant et al. (Jun. 2003) "Functionalized Silicon Membranes for Selective Bio-Organisms Capture," Nat. Mater. 2:391-395.
Li et al. (2006) "Catalyst-Assisted Formation of Nanocantilever Arrays on ZnS Nanoribbons by Post-Annealing Treatment," J. Phys. Chem. B 110(13):6759-6762.
Liu et al. (1999) "Controlled deposition of individual single-walled carbon nanotubes on chemically functionalized templates," Chem. Phys. Lett., 303:125-129.
Lu et al. (Apr. 2010) "Water-Insoluble Silk Films with Silk I Structure," Acta Biomater. 6(4):1380-1387.
Mehring C. et al. (2003) Inference of hand movements from local field potentials in monkey motor cortex. Nature Neurosci. 6, 1253-1254.
Menard et al. (2007) Micro- and Nanopatterning Techniques for Organic Electronic and Optoelectronic Systems, Chem. Rev. 107:1117-1160.
Michalske et al. (1985) "Closure and Repropagation of Healed Cracks in Silicate Glass," J. Am. Ceram. Soc. 68:586-590.
Minev et al. (2010) "Impedance Spectroscopy on Stretchable Microelectrode Arrays," Appl. Phys. Lett. 97:043707.
Murakami et al. (2005) "Polarization Dependence of the Optical Absorption of Single-Walled Carbon Nanotubes," Phys. Rev. Lett., 94, 087402.
Murphy et al;(2008) "Modification of Silk Fibroin Using Diazonium Coupling Chemistry and the Effects on hMSC Proliferation and Differentiation," Biomaterials 29:2829-2838.
Notice of Allowance, Corresponding to U.S. Appl. No. 12/723,475, mailed on Oct. 14, 2011.
Notice of Allowance, U.S. Appl. No. 12/405,475, mailed Mar. 1, 2012.
O'Riordan et al. (2004) "Field Configured Assembly: Programmed Manipulation and Self-Assembly at the Mesoscale," Nano Lett. 4:761-765.
Office Action and Response, Corresponding to U.S. Appl. No. 11/423,287, Mailed Feb. 13, 2008.
Office Action and Response, Corresponding to U.S. Appl. No. 11/421,654, Mailed Sep. 29, 2009.
Office Action and Response, Corresponding to U.S. Appl. No. 11/858,788, Mailed Beginning Jan. 28, 2011.
Office Action, Corresponding to U.S. Appl. No. 12/616,922, Issued Apr. 9, 2012.
Omenetto et al. (2008) "A New Route for Silk," Nature Photon. 2:641-643.
Ouyang et al. (2002) "High-Performance, Flexible Polymer Light-Emitting Diodes Fabricated by a Continuous Polymer Coating Process," Adv. Mat. 14:915-918.
Overholt et al. (2005) "Photodynamic Therapy for Esophageal Cancer using a 180° Windowed Esophageal Balloon," Lasers in Surg. Med. 14:27-33.
Park et al. (Aug. 2009) "Printed Assemblies of Inorganic Light-Emitting Diodes for Deformable and Semitransparent Displays," Science 325:977-981.
Park et al. (Web Release Feb. 22, 2009) "Biodegradable Luminescent Porous Silicon Nanoparticles for in Vivo Applications," Nature Mater. 8:331-336.
Parker et al. (2009) "Biocompatible Silk Printed Optical Waveguides," Adv. Mater. 21:2411-2415.
Patolsky et al. (2006) "Detection, Stimulation, and Inhibition of Neuronal Signals with High-Density Nanowire Transistor Arrays," Science 313:1100-1104.
Perry et al. (2008) "Nano- and Micropatterning of Optically Transparent, Mechanically Robust, Biocompatible Silk Fibroin Films," Adv. Mater. 20:3070-3072.
Pimparkar et al. (Feb. 2007) "Current-Voltage Characteristics of Long-Channel Nanobundle Thin-Film Transistors: A 'Bottom-Up' Perspective," IEEE Electron Dev. Lett. 28(2):157-160.

(56) References Cited

OTHER PUBLICATIONS

Qian et al. (2006) "Scaling Effects of Wet Adhesion in Biological Attachment Systems," Acta Biomaterialia 2:51-58.
Randall et al. (2005) "Permeation-driven flow in poly(dimethylsiloxane) microfluidic devices," Proc. Nat. Acad. Sci. USA 102(31):10813-10818.
Rao et al. (2003) "Large-scale assembly of carbon nanotubes," Nature, 425:36-37.
Razavi et al. (2009) "Three Dimensional Nanopillar Array Photovoltaics on Low Cost and Flexible Substrates," Nature Materials 8:648-653.
Rubehn et al. (2009) "A MEMS based Flexible Multichannel ECoG-Electrode Array," J. Neural Eng. 6:036003.
Ryu et al. (2009) "Human Cortical Prostheses: Lost in Translation?" Neurosurg Focus 27(1):E5.
Sangwal et al. (1997) "Nature of multilayer steps on the {100} cleavage planes of MgO single crystals," Surf. Sci., 383:78-87.
Santin et al. (1999) "In vitro Evaluation of the Inflammatory Potential of the Silk Fibroin," J. Biomed. Mater. Res. 46:382-389.
Scherlag et al. (1969) "Catheter Technique for Recording His Bundle Activity in Man," Circulation 39:13-18.
Schindl et al. (2003) "Direct Stimulatory Effect of Low-Intensity 670-nm Laser Irradiation on Human Endothelial Cell Proliferation," Br. J. Dermatol. 148:334-336.
Schlegel et al. (2002) "Structures of quartz (1010)- and (1011)-water interfaces determined by X-ray reflectivity and atomic force microscopy of natural growth surfaces," Geochim. Cosmochim. Acta, vol. 66, No. 17, pp. 3037-3054.
Schmid et al. (May 11, 1998) "Light-Coupling Masks for Lensless, Sub-wavelength Optical Lithography," Appl. Phys. Lett. 72(19):2379-2381.
Search Report Corresponding to Singapore Patent Application No. SG 200607372-0, Mailer Oct. 17, 2007.
Seidel et al. (2004) "High-Current Nanotube Transistors," Nano Lett., vol. 4, No. 5, pp. 831-834.
Sekitani et al. (2009) "Stretchable Active-Matrix Organic Light-Emitting Diode Display Using Printable Elastic Conductors," Nature Mater. 8:494-499.
Shi et al. (2001) "Free-Standing Single Crystal Silicon Nanoribbons," J. Am. Chem. Soc. 123(44):11095-11096.
Shin et al. (2003) "PDMS-Based Micro PCR Chip with Parylene Coating," J. Micromech. Microeng. 13:768-774.
Siegel et al. (2009) "Thin, lightweight, Foldable Thermochromic Displays on Paper," Lab Chip 9:2775-2781.
Siegel et al. (2010) "Foldable Printed Circuit Boards on Paper Substrates," Adv. Funct. Mater. 20:28-35.
Snow et al. (2003) "Random networks of carbon nanotubes as an electronic material," Appl. Phys. Lett., vol. 82, No. 13, pp. 2145-2147.
Snow et al. (2005) "High-mobility carbon-nanotube transistors on a polymeric substrate," Appl. Phys. Lett., 86, 033105.
So et al. (2008) Organic Light-Emitting Devices for Solid-State Lighting, MRS Bull. 33:663-669.
Sofia et al. (2001) "Functionalized Silk-Based Biomaterials for Bone Formation," J. Biomed. Mater. Res. 54:139-148.
Soong et al. (1984) "Adverse Reactions to Virgin Silk Sutures in Cataract Surgery," Ophthalmology 91:479-483.
Star et al. (2004) "Nanotube Optoelectric Memory Devices," Nano Lett., vol. 4, No. 9, pp. 1587-1591.
Streetman et al. (2000) "Intrinsic Material," In; Solid State Electronic Devices, 5th Ed., Prentice Hall; Upper Saddle River, NJ; pp. 74-75.
Su et al. (2000) "Lattice-Oriented Growth of Single-Walled Carbon Nanotubes," J. Phys. Chem. B 104(28):6505-6508.
Sum et al. (2009) "Near-Infrared Spectroscopy for the Detection of Lipid Core Coronary Plaques," Curr. Cardiovasc. Imag. Rep. 2:307-315.
Sun et al. (2007) "Controlled Buckling of Semiconductor Nanoribbons for Stretchable Electronics," Nat. Nanotechnol. 1:201-207.
Sun et al. (2007) "Inorganic Semiconductors for Flexible Electronics," Adv. Mater. 19:1897-1916.
Sun et al. (2007) "Structural Forms of Single Crystal Semiconductor Nanoribbons for High-Performance Stretchable Electronics," J. Mater Chem. 17:832-840.
Supplementary European Search Report, Corresponding to European Application No. 04 81 2651, Completed Oct. 19, 2010.
Sze, S. (1985) Semiconductor Devices: Physics and Technology, New York: Wiley, pp. 428-467.
Sze, S. (1988) VLSI Technology, Chapter 8, Ion Implantation, Mcgraw-Hill, 327-374, 566-611.
Thornwood et al. (Oct. 1, 1990) "Utilizing Olptical Lithography in the Sub-Micron Dimensional Regime," IBM Tech. Disc. Bull. 33(5):187-188.
Timko et al. (2009) "Electrical Recording from Hearts with Flexible Nanowire Device Arrays," Nano Lett. 9:914-918.
Tong (1999) Semiconductor Wafer Bonding: Science and Technology, John Wiley; New York, pp. 187-201.
Vepari et al. (Aug. Sep. 2007) "Silk as a Biomaterial," Prog. Polym. Sci. 32(8-9):991-1007.
Vinck et al. (2003) "Increased Fibroblast Proliferation Induced by Light Emitting Diode and Low Power Laser Irradiation," Lasers Med. Sci. 18:95-99.
Viventi et al. (Mar. 2010) "A Conformal, Bio-Interfaced Class of Silicon Electronics for Mapping Cardiac Electrophysiology," Sci. Trans. Med. 2(24):24ra22.
Waksman et al.(2008) "Photopoint Photodynamic Therapy Promotes Stabilization of Atherosclerotic Plaques and Inhibits Plaque Progression," J. Am. Coll. Cardiol. 52:1024-1032.
Wang et al. (2005) "Electronically Selective Chemical Functionalization of Carbon Nanotubes: Correlation between Raman Spectral and Electrical Responses," J. Am. Chem. Soc., 127:11460-11468.
Wang et al. (Aug-Sep. 2008) "In Vivo Degradation of Three-Dimensional Silk Fibroin Scaffolds," Biomaterials 29(24-25):3415-3428.
Waxman et al. (2009) "In vivo Validation of a Catheter-Based Near-Infrared Spectroscopy System for Detection of Lipid Core Coronary Plaques: Initial Results of the Spectacl Study," J. Am. Coll. Cardiol. Img. 2:858-868.
Waxman, S. (2008) "Near-Infrared Spectroscopy for Plaque Characterization," J. Interv. Cardiol. 21:452-458.
Wilson et al. (2006) "ECoG Factors Underlying Multimodal Control of a Brain-Computer Interface," IEEE Trans. Neural Syst. Rehabil. Eng. 14:246-250.
Wise et al. (Jul. 2008) "Microelectrodes, Microelectronics, and Implantable Neural Microsystems," Proc. IEEE 96(7):1184-1202.
Wong-Riley et al. (2005) "Photobiomodulation Directly Benefits Primary Neurons Functionally Inactivated by Toxins," J. Biol. Chem. 280:4761-4771.
Woodburn et al. (1996) "Phototherapy of Cancer and Atheromatous Plaque with Texaphyrins," J. Clin. Laser Med. Surg. 14:343-348.
Wu et al. (2001) "Direct Observation of Vapor-Liquid-Solid Nanowire Growth," J. Am. Chem. Soc. 123(13):3165-3166.
Wu et al. (2002) "Block-by-Block Growth of Single-Crystalline Si/SiGe Superlattice Nanowires," Nano Lett. 2(2):83-86.
Wu et al. (2002) "Growth of Au-Catalyzed Ordered GaAs Nanowire Arrays by Molecular-Beam Epitaxy," Appl. Phys. Lett. 81:5177-5179.
Xiao et al. (2003) "High-mobility thin-film transistors based on aligned carbon nanotubes," Appl. Phys. Lett., vol. 83, No. 1, pp. 150-152.
Yanina et al. (2002) "Terraces and ledges on (001) spinel surfaces," Surf. Sci., 513:L402-L412.
Yao et al. (2008) "Seeing Molecules by Eye: Surface Plasmon Resonance Imaging at Visible Wavelengths with High Spatial Resolution and Submonolayer Sensitivity," Angew. Chem. 47:5013-5017.
Yao et al. (2010) "Functional Nanostructured Plasmonic Materials," Adv. Mater. 22:1102-1110.
Yeager et al. (Aug. 30, 2008) "Characterization of Flexible ECoG Electrode Arrays for Chronic Recording in Awake Rats," J. Neurosci. Methods 173(2):279-285.
Yu et al. (2004) "The Yield Strength of Thin Copper Films on Kapton," J. Appl. Phys. 95:2991-2997.

(56) References Cited

OTHER PUBLICATIONS

Zhang et al. (2001) "Electric-field-directed growth of aligned single-walled carbon nanotubes," Appl. Phys. Lett., vol. 79, No. 19. pp. 3155-3157.

Zhang et al. (2006) "Anomalous Coiling of SiGe/Si and SiGe/Si/Cr Helical Nanobelts," Nano Lett. 6(7):1311-1317.

Zheng et al. (1998) "Sudden Cardiac Death in the United States, 1989 to 1998," Circulation 104, 2158-2163.

Zhu et al. (2005) "Spin on Dopants for High-Performance Single Crystal Silicon Transistors on Flexible Plastic Substrates," Applied Physics Letters 86, 133507 (2005).

Zipes et al. (2006) "ACC/AHA/ESC 2006 Guidelines for Management of Patients With Ventricular Arrhythmias and the Prevention of Sudden Cardiac Death: A Report of the American College of Cardiology/American Heart Association Task Force and the European Society of Cardiology Committee for Practice Guidelines (Writing Committee to Develop Guidelines for Management of Patients With Ventricular Arrhythmias and the Prevention of Sudden Cardiac Death," Circulation 114:385-484.

European Search Report; PCT/US/2009059892; Feb. 18, 2014; 6 pages.

Demura et al., "Immobilization of Glucose Oxidase with *Bombyx Mori* Silk Fibroin by Only Stretching Treatment and its Application to Glucose Sensor," Biotechnology and Bioengineering, vol. 33, 598-603 (6 pages) (1989).

Halsted, "Ligature and Suture Material," Journal of the American Medical Association, vol. LX, No. 15, 1119-1126, (8 pages) (Apr. 12, 1913).

Omenetto et al., "New Opportunities for an Ancient Material," Science, vol. 329, 528-531 (5 pages) (Jul. 30, 2010).

Tsukada et al., "Structural Changes of Silk Fibroin Membranes Induced by Immersion in Methanol Aqueous Solutions," Journal of Polymer Science, vol. 32, 961-968 (8 pages) (1994).

Wang et al., "Controlled Release From Multilayer Silk Biomaterial Coatings to Modulate Vascular Cell Responses" Biomaterials, 29, 894-903 (10 pages) (Nov. 28, 2008).

European Office Action for European Application No. 09 819 838.5, dated Oct. 5, 2015, 4 pages.

Japanese Office Action for Japanese Application No. 2014-225406, dated Nov. 4, 2015, with English translation, 9 pages.

\* cited by examiner

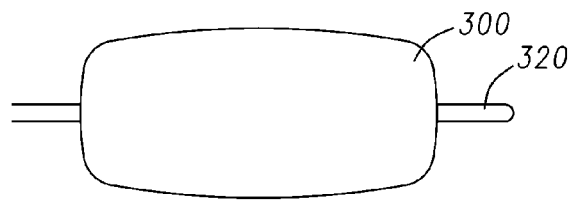
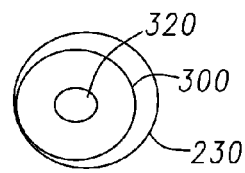
*Fig. 3A*  *Fig. 3B*
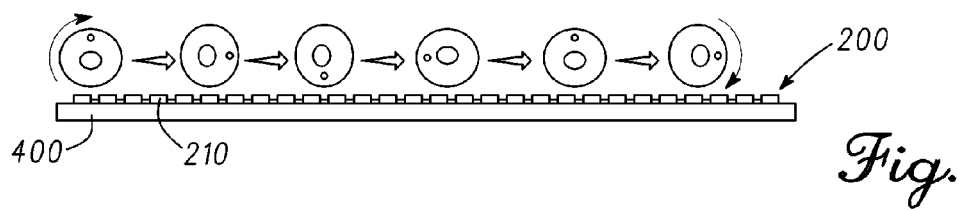
*Fig. 3C*
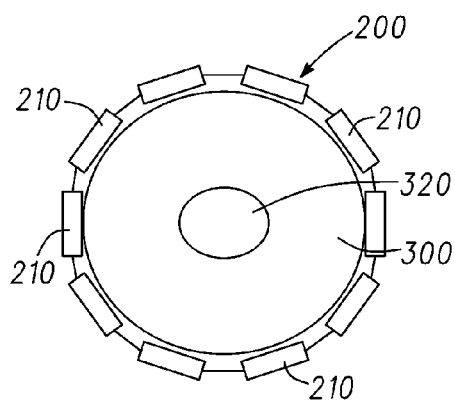
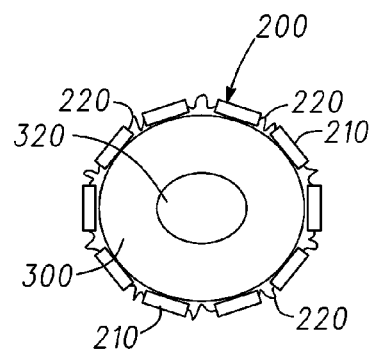
*Fig. 3D*  *Fig. 3E*

CATHETER BALLOON HAVING STRETCHABLE INTEGRATED CIRCUITRY AND SENSOR ARRAY

CROSS REFERENCE TO RELATED APPLICATIONS

This application claims the benefit of U.S. Provisional Application No. 61/103,361 entitled "Catheter Balloon Sensor and Imaging Arrays" filed on Oct. 7, 2008 (the "361 provisional"), the entirety of which is incorporated herein by reference. This application also claims the benefit of U.S. Provisional Application No. 61/113,007 entitled "Catheter Balloon with Sensor and Imaging Array" filed Nov. 10, 2008 (the "'007 provisional), the entirety of which is incorporated herein by reference.

FIELD OF THE INVENTION

The present invention relates to systems, apparatuses, and methods utilizing expandable or stretchable integrated circuitry and sensor arrays on expandable or stretchable materials, and in a particular, on balloon catheters.

BACKGROUND OF THE INVENTION

Intraluminal devices have become important in the diagnoses and treatment of a variety of medical conditions ranging from conditions associated with the digestive system to conditions related to the cardiocirculatory system. Current intraluminal sensing and therapeutic devices suffer from various disadvantages due to a lack of sophistication related to the sensing, imaging, and therapeutic functions. In some cases, such lack of sophistication resides in the fact that many such devices are configured with passive circuitry. Active integrated circuits utilizing multifunctional operative devices offer a variety sophisticated sensing, imaging, and therapeutic functions, including (but not limited to) pressure sensing, light imaging, and drug delivery. In the case where intraluminal devices have such active integrated circuits, such devices suffer from other disadvantages not the least of which is that such devices are unable to achieve direct contact with the part of the body being measured. The inability to achieve direct contact of such devices is attributable to the rigid nature of the operative devices and accompanying circuitry. This rigidity prevents devices from coming into full contact with soft, pliable, curved, and/or irregularly shaped tissue, which compromises accuracy of measurements.

By way of a non-limiting example, one such area where a need exists to obtain better contact and thus accuracy is in the area of analyzing arterial plaque deposits. Plaque deposits in the arterial lumen are widely recognized as a common cause of myocardial infarction, unstable angina, and even death. Plaques found inside the arterial lumen are classified as 'vulnerable' or 'stable.' These two types of plaque have significantly different compositions that give rise to variations in electrical, thermal, chemical, and material properties. Vulnerable plaque consists of a lipid core containing large amounts of cholesterol deposits, inflamed cells (macrophages), low levels of collagen and other matrix proteins. The collagen and associated fibrous proteins are found as a thin surface layer, encapsulating all of the other structural components. Based on size and the effects of shear stress exerted by the flow of blood, the enclosure formed by the thin fibrous caps is susceptible to mechanical rupture. The rupture and subsequent release of the deposits internal to the plaque is a key mechanism underlying thrombosis and myocardial infarctions.

In contrast, stable plaque is much less susceptible to rupture and thus is far less dangerous. Stable plaques have a significantly more robust outer shell, consisting of a thick fibrous cap. Although stable plaques can cause significant stenosis that may require intervention, the effect of arterial occlusion is much less harmful than the rupture of vulnerable plaque. It is important to note that the vulnerable plaque typically form a narrowing of less than 50%, suggesting that the deleterious effects of a vulnerable plaque cannot be predicted based on the extent of occlusion alone. Moreover, it is difficult to distinguish between vulnerable and stable plaque based purely on extracorporeal imaging techniques.

One direct way to detect the presence of vulnerable plaque is through temperature and pressure sensing near the plaque site, since plaque has non-uniform surface contours and because there is a significant difference in the temperature of vulnerable plaque compared to that of the normal lumen and stable angina. But current temperature sensors are fabricated on rigid supports and embedded within the catheter body. One such sensor is located at the center of the lumen in the catheter. This design requires compensation for the distance separating the temperature sensor from the plaque wall. Adjustments in temperature recordings are made based on a displacement sensor that senses the distance between the plaque wall and the catheter within the lumen. Although this type of device can theoretically estimate the temperature at the plaque, complications and errors can arise.

SUMMARY OF THE INVENTION

In embodiments, the present invention may be a device that includes an inflatable body having a surface, and a stretchable electronic circuit comprising at least one discrete operative device being in electronic communication with at least one other discrete operative device, where the stretchable electronic circuit may be affixed to the inflatable body.

The stretchable electronic circuit may comprise a single crystalline semiconductor structure, and may be a printable electronic circuit. The stretchable electronic circuit is operable when the inflatable body is inflated even when the inflatable body is inflated, up to 150 and in some cases, up to 300 percent of its original size.

The electronic communication between the operative devices may be wireless. The operative devices may further comprise a transceiver receiving data from the discrete operative device. Alternatively, electronic communication may be through a physical electrical connection. This physical electrical connection may be stretchable. In some embodiments the physical electrical connection is configured to buckle when the inflatable body is deflated. In some embodiments the physical electrical connection is configured to be non-coplanar with the inflatable body when the inflatable body is relaxed, and be coplanar with the inflatable body when the inflatable body is inflated. The inflatable body may be made of a polymer. The inflatable body may be a balloon, which in some embodiments, may be fitted with a stent.

In embodiments, the discrete operative device may include an amplifier, a semiconductor structure, a transducer, a sensor, and the like. Such sensors may detect temperature, capacitance, pressure, reflectivity, chemicals, enzymatic activity, and mechanical properties. In some embodiments the device is in communication with a processor programmed to generate data for an image related to a body lumen, such as spatial, temperature, tactile image, visual map, and the like.

The operative device may include a sensor, where the operative device may continuously generate data, and where the continuously generated data may be recorded.

Further, the device of the present invention may comprise a drug delivery polymer comprising a drug, where the stretchable electronic circuit may activate the drug delivery polymer.

In embodiments, the present invention provides a method, the method being executed by a processor programmed to perform the steps of the method. In embodiments the method is to detect parameters inside a lumen, including inserting a device of the present invention into a lumen, inflating the inflatable body, contacting the lumen, measuring a parameter of the lumen. Further, the present invention may deliver a therapy based on the measurement, and generate a graphical output based on said measured parameter.

BRIEF DESCRIPTION OF THE DRAWINGS

FIGS. 3A-E show fabrication steps related to embodiments of the present invention.

DETAILED DESCRIPTION OF THE INVENTION

As described herein, the present invention comprises devices, systems, and methods utilizing stretchable electronic circuits on expandable or inflatable surfaces. With reference to the present invention, the term "stretchable", and roots and derivations thereof, when used to modify circuitry or components thereof is meant to encompass circuitry that comprises components having soft or elastic properties capable of being made longer or wider without tearing or breaking, and it is also meant to encompass circuitry having components (whether or not the components themselves are individually stretchable as stated above) that are configured in such a way so as to accommodate and remain functional when applied to a stretchable, inflatable, or otherwise expandable surface. The term "expandable", and roots and derivations thereof, when used to modify circuitry or components thereof is also meant to have the meaning ascribed above. Thus, "stretch" and "expand", and all derivations thereof, may be used interchangeably when referring to the present invention.

Figure 1:
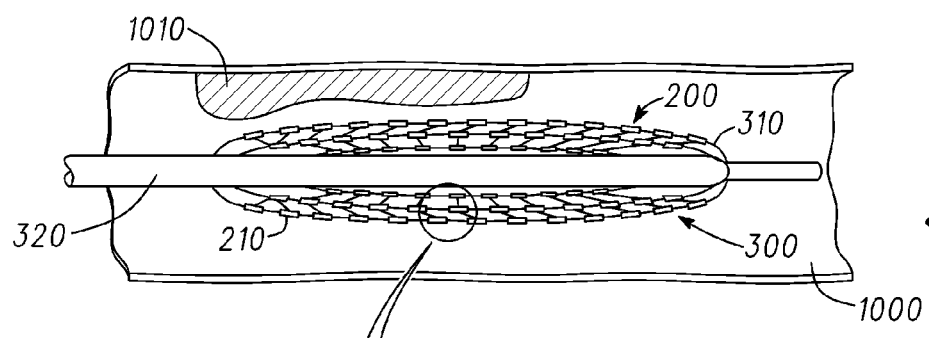
FIG. 1 shows an embodiment of the invention in a deflated state and inside a body lumen.
Figure 1A:
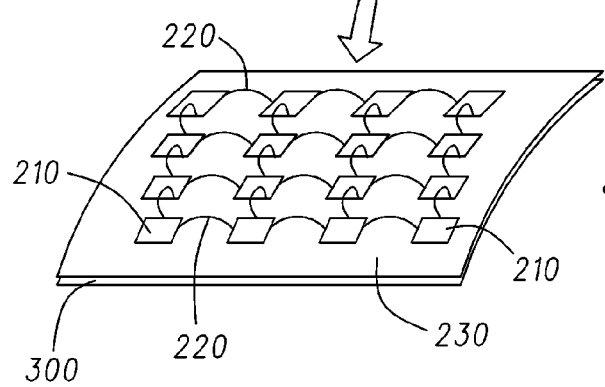
FIG. 1A is an expanded view of a portion of FIG. 1.

FIG. 1 shows an embodiment of the invention wherein a stretchable electronic circuit 200 is on an expandable body 300. In embodiments such as the one shown in FIG. 1, the expandable body 300 is inflatable and in some embodiments (such as the one shown in FIG. 1) the inflatable body is a balloon on a catheter. The skilled artisan will appreciate that the balloon and catheter together are referred to as a "balloon catheter", which is a type of catheter with an inflatable balloon at its tip and which is used during a catheterization procedure for various medical procedures such as to enlarge a narrow opening or passage within the body. The deflated balloon catheter is positioned, then inflated to perform the necessary procedure, and deflated again in order to be removed.

FIG. 1 shows the balloon catheter in a relaxed or deflated state, which is inserted into a lumen 1000 which, in this embodiment is an artery. FIG. 1 shows arterial plaque 1010 formed on the inner wall of the artery. The stretchable electronic circuitry 200 is on the surface of the inflatable body 300 and will be discussed in more detail below.

In embodiments, the circuitry 200 utilizes complementary metal-oxide semiconductor (CMOS) technology. CMOS devices offer a variety sophisticated sensing, imaging, and therapeutic functions, including (but not limited to) pressure sensing, light imaging, and drug delivery. The device arrays are designed to withstand stretching and bending and can be embedded in or affixed onto a stretchable surface, such as that made of a polymer material.

Figure 2:
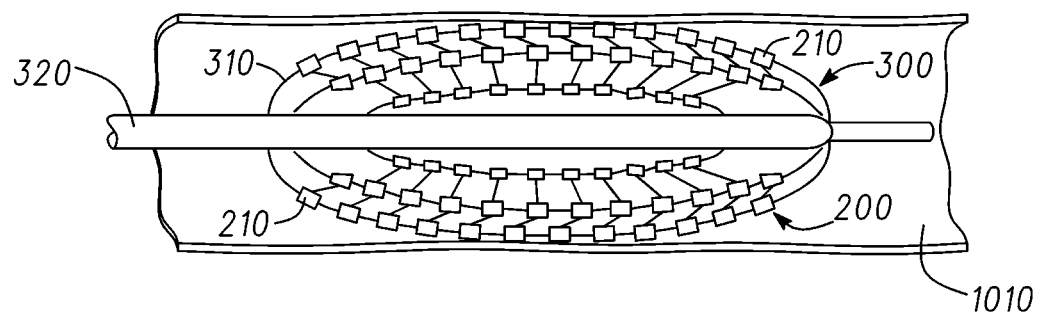
FIG. 2 shows an embodiment of the invention in an inflated state and inside a body lumen.

FIG. 2A shows a detailed view the circuitry 200 of the claimed invention while the device is in a deflated or unexpanded state. The circuitry 200 of the invention comprises at least one operative device 210 which is, in embodiments, in electronic communication with at least one other operative device 210. In embodiments, the operative devices are discrete (in embodiments, arranged in a "device island" arrangement as described below) and are themselves capable of performing the functionality described herein, or portions thereof. In embodiments, such functionality of the operative devices 210 can include integrated circuits, physical sensors (e.g. temperature, pH, light, radiation etc), biological and/or chemical sensors, amplifiers, A/D and D/A converters, optical collectors, electro-mechanical transducers, piezo-electric actuators, light emitting electronics which include LEDs, and combinations thereof. The purpose and advantage of using standard ICs (in embodiments, CMOS, on single crystal silicon) is to have and use high quality, high performance, and high functioning circuit components that are also already commonly mass-produced with well known processes, and which provide a range of functionality and generation of data far superior to that produced by a passive means. For purposes of the invention, passive systems are defined by their absence of local amplification, and/or a lack of the ability to perform (on-board) any the functionality described above and herein. In order to accommodate the discrete operative devices 210, which may be rigid, to the demands of an expandable and stretchable substrate 300 such as a catheter balloon, the operative devices 200 are fabricated such that they are located in discrete and isolated "device islands" and are electrically interconnected by stretchable interconnects, or interconnects configured to accommodate an expandable or stretchable surface. The interconnects are referred to as 220. In the embodiment shown in FIG. 2A, it can be seen that the interconnects 220 are flexible and thus able to accommodate the stretching caused by the inflation of the balloon 300 (shown in FIG. 2B). Thus, the entirety of the circuitry 200 is expandable or stretchable. In the embodiment shown in FIG. 2A, the interconnects 220 are buckled or non-coplanar when the balloon 300 is in a deflated state. When the balloon 300 is inflated (as shown in FIG. 2B), the interconnects 220 become either coplanar or non-buckled so as to accommodate the increased distance between the discrete operative devices 210 upon inflation. Additionally, serpentine interconnects may be used.

In embodiments, the electronic communication between the discrete operative devices and/or between said devices and separate devices could be wireless. Therefore, said devices may comprise a transducer, transmitter, or receiver capable of such wireless transmission.

The specific fabrication method for such circuitry may depend on the specific circuit classes desired to incorporate into the device, and the specific characteristics of the circuitry, including those of the discrete operative devices, the interconnects, etc., include, but are not limited to, those disclosed in the following references each of which is incorporated herein by reference in its entirety: U.S. Pat. No. 7,557,367 to Rogers et al. entitled "Stretchable Semiconductor Elements and Stretchable Electrical Circuits"; Ko et al., "A hemispherical electronic eye camera based on compressible silicon optoelectronics," Nature (2008) (which is attached the '007 provisional Appendix B and is referred to in the '361 provisional); D.-H. Kim, W. M. Choi, J.-H. Ahn, H.-S. Kim, J. Song, Y. Huang, Z. Liu, C. Lu, C. G. Koh and J. A. Rogers, "Complementary Metal Oxide Silicon Integrated Circuits Incorporating Monolithically Integrated Stretchable Wavy Interconnects," Applied Physics Letters 93, 044102 (2008) (which is attached to the '007 provisional as Appendix C); D.-H. Kim, J.-H. Ahn, W.-M. Choi, H.-S. Kim, T.-H. Kim, J. Song, Y. Y. Huang, L. Zhuangjian, L. Chun and J. A. Rogers, "Stretchable and Foldable Silicon Integrated Circuits," Science 320, 507-511 (2008) (which is attached to the '007 provisional as Appendix D); R. Dinyari et al, K. Huang, S. B. Rim, P. B. Catrysse and P. Peumans, "Curved silicon focal plane arrays," Appl. Phys. Lett. (2008) (which is attached to the '007 provisional as Appendix E and is referred to in the '361 provisional). Also to provide fabrication methods for such stretchable circuitry and to describe the specific characteristics of the circuitry, including those of the discrete operative devices, the interconnects, etc., are discussed in the following references, each of which is incorporated herein by reference in its entirety: United States Published Patent Application No. 2006/0286488 entitled "Methods and Devices for Fabricating Three-Dimensional Nanoscale Structures"; U.S. Pat. No. 7,195,733 to Rogers et al. entitled "Composite Patterning Devices for Soft Lithography"; U.S. Pat. No. 7,521,292 to Rogers et al. entitled "Stretchable Form of Single Crystal Silicon for High Performance Electronics on Rubber Substrates"; United States Published Patent Application No. US 2009/0199960 for Rogers et al. entitled "Pattern Transfer Printing by Kinetic Control of Adhesion to an Elastomeric Stamp"; United States Published Patent Application. No. 2007/0032089 for Nuzzo et al. entitled "Printable Semiconductor Structures and Related Methods of Making and Assembling"; United States Published Patent Application No. 2008/0157235 for Rogers et al. entitled "Controlled Buckling Structures in Semiconductor Interconnects and Nanomembranes for Stretchable Electronics"; United States Published Patent Application No. 2008/0108171, Release Strategies for Making Transferable Semiconductor Structures, Devices and Device Components, and also United States Patent Applications having the following Ser. No. 11/145,574 entitled "Methods and Devices for Fabricating and Assembling Printable Semiconductor Elements, filed Jun. 2, 2005, Ser. No. 11/675,659 entitled "Devices and Methods for Pattern Generation by Ink Lithography, filed Feb. 16, 2007, and Ser. No. 12/398,811 entitled "Stretchable and Foldable Electronic Devices", filed on Mar. 5, 2009.

Such circuits may be applied to the surface of the balloon or to a stretchable or expandable material that may be wrapped around the balloon via transfer printing of partially or wholly processed single-crystal silicon devices, using methods described in the aforementioned references or also methods in M. A. Meitl, Z.-T. Zhu, V. Kumar, K. J. Lee, X. Feng, Y. Y. Huang, I. Adesida, R. G. Nuzzo and J. A. Rogers, "Transfer Printing by Kinetic Control of Adhesion to an Elastomeric Stamp," Nature Materials 5, 33-38 (2006) (attached to the '007 provisional as Appendix F).

A non-limiting example of the complete fabrication steps of an embodiment of the invention, i.e., a catheter balloon instrumented with temperature sensors, is described in the following paragraphs. It should be noted that while the embodiment described below refers to an inflatable system (specifically a catheter balloon), the skilled artisan will appreciate that such principals of operation will apply to situations where the body on which the circuitry is applied is otherwise stretchable or expandable but not inflatable.

Arrays of discrete operative devices 210, which may include temperature sensors and associated differential amplifiers, buffers, A/D converters, logic, memory, clock and active matrix switching transistors are laid out in a "device island" arrangement. The device islands can be 50 μm×50 μm squares, most of which accommodate a single conventional sensor circuit, e.g., a temperature sensor, connected to a buffer, that is itself connected to an amplifier. The temperature sensor, which may be resistive, diode-based, etc., as described in greater detail below, supplies a signal that reflects temperature (or a temperature change), and the remaining sensor circuitry conditions the signal for subsequent processing.

In embodiments, discrete operative devices 210 accommodate active matrix switches and A/D converters for transforming an analog temperature signal into digital form, and some operative devices accommodate logic circuitry capable of reading in digital signals and processing them (e.g., to assign a value to the sensed temperature or temperature change). These circuits may output the temperature reading to another module or, and are capable of outputting data or storing it in on-board memory cells.

The circuitry is arranged and designed such that preferably only about one, but not more than about 100 electrical interconnections are required between any two device islands. In embodiments, the circuits are then fabricated on an SOI wafer (although it should be understood that standard wafers could be used)(1.2 μm thick top Si, 1 μm thick buried oxide) using standard CMOS fabrication technology, and the silicon space in between each island is etched away to isolate each island. The circuits are protected by a polyimide passivation layer, then a short HF etch is done to partially undercut the islands. The passivation layer is removed, and then a thin film of SiO2 is deposited and patterned (100 nm thick) by PECVD or other deposition technique combined with a liftoff procedure, such that the oxide layer covers most of the space between discrete operative devices except for a region around each device island that is about 5 μm wide. This will be an additional sacrificial material for subsequent use in the fabrication process. Another polyimide layer is spun on and patterned into the shape of the interconnects. Typically one interconnect may extend from the center of one device to the center of another device. Alternately, two interconnects may extend from each corner of the device to two different device corners. Other interconnect configurations are understood. The interconnect bridges may be about 25 μm wide and may accommodate multiple electrical lines. The polyimide partially fills underneath the device island where it is undercut; this serves to stabilize the island later in the release process and prevent it from floating away. VIAs are etched into the PI layer to allow metal wires, patterned in the next step, to contact the circuits and connect one island to another. (This step can be repeated to form additional sets of wires located above the first set.) Another PI layer is spun on (covering the wires and everything else). The PI (both layers) is then isolated by etching with a deposited SiO2 hard mask, in O2 RIE. PI located outside the devices and bridges is etched, as well as PI covering areas that are meant to be externally electrically interfaced, and small areas leading to the underlying oxide. Etch holes may be formed if necessary and then transferred through the silicon or metal layers by wet and or dry etching. The underlying buried oxide is etched away using HF etchant to free the devices, which remain attached to the handle substrate due to the first polyimide passivation layer which contacts the handle wafer near the border around the devices.

If the HF etch is not controllable enough and finds a way to seep under the PI isolation layer and attack the CMOS devices, then prior to the first PI passivation a short Argon sputtering can be done to remove any native oxide followed by amorphous silicon sputtering followed by the PI passivation and the rest of the processing.

After rinsing, the devices are left to air dry. After drying, they are picked up with a PDMS stamp, and transfer printed onto either the surface of an expandable/inflatable body 310, or a surface of an expandable/inflatable body coated with a thin PDMS layer, or a separate thin PDMS layer (that may later be wrapped around the balloon). FIG. 3A shows a side view of a balloon with the PDMS layer 230 wrapped around the surface of the balloon 300. FIG. 3B is a cross-sectional view which shows the catheter 320, the surface of the balloon 300, and the thin PDMS layer 230 applied to the balloon 300.

It is also possible for a thin PDMS mold to be made of half the (inflated) balloon shape, such that it can be stretched flat, and have circuits transferred onto it in the flat state, and then released to pop back into the half-balloon shape; this half-balloon can then be easily attached to the real balloon, and may even be glued. It is noted that in all transfer cases, the circuits are on the outside of the balloon, and the bridges (also referred to as interconnects and physical electrical connections herein) pop or buckle outward when the devices are compressed or the expandable/inflatable body is otherwise in a relaxed or deflated state. In the inflated state, the bridges should be fairly non-buckled and/or coplanar with the surface of the inflatable body 300 so that in the deflated state they can buckle to accommodate the significant compressive stress. Alternately this process can be repeated with a mold made in the deflated state of the balloon, and stretched beyond flat so that it is significantly expanded, such that after the circuits are transferred and the mold is released, they compress significantly. In this case, they should be compressed enough so that after transfer to the real balloon, when it is fully expanded, the bridges are nearly flat or fully extended and almost non-buckled.

In the case where the circuitry 200 is directly transferred to the balloon, the PDMS stamp should be made thin (~100-500 µm in thickness) and thereby compliant enough to conform to the shape of the balloon.

In the case where the circuitry is first transferred to a separate thin PDMS layer, the PDMS layer may be on a rigid substrate so that the transferring can be done easily. Then the PDMS layer can be peeled off the substrate and wrapped around the balloon either in the inflated or deflated state, depending on whether the circuitry was transferred with any prestrain or not. It may be desirable to make the circuitry in a 1D array rather than a 2D array. In this way, the thin PDMS layer is a long, narrow ribbon that can be easily wrapped around the balloon so as to cover the entire balloon surface. Alternatively, if it is desired that the circuitry face inwards to the balloon, the balloon can be directly rolled along a planar array of circuitry 200 on PDMS carrier substrate 400 as shown in FIG. 3D. The balloon can be subsequently deflated and/or re-inflated. Deflation can cause the interconnects in the circuitry to buckle and take on compression forces imposed by deflation as shown in FIG. 3E. It should be understood that these stamping methodologies applied to the balloon catheter can be applied to stamp the electronic circuitry in all of the embodiments described below.

In embodiments where the circuitry is facing outwards on the balloon, the circuitry may be electrically externally interfaced at conductive pads that should be designed to be located at the base of the balloon. Anisotropic conductive film (ACF) connectors can be used to interface to these conductive pads, by pressing and heating the film onto the pads. The film can then run down the length of the catheter since it is so thin and flexible.

In embodiments where the circuitry is encapsulated or facing inwards, the circuitry may be electrically externally interfaced by first removing part of the encapsulating polymer over the conductive pads through wet or dry chemical etching, or physical mechanical removal of material, including but not limited to drilling. At this point, the ACF may be incorporated. Alternatively, the stretchable circuitry may be electrically interfaced to an ACF prior to the transfer or encapsulation process.

In embodiments, it may be possible for the circuitry to be powered externally optically, using the catheter tube as a waveguide and having PV cells made in a stretchable format in addition to the rest of the circuitry. In addition, LED islands may be made to perform optical data communication down the catheter waveguide. Alternately, thin film batteries may be used to power the circuitry. Alternately, RF communication circuits on the device may be used to wirelessly communicate outside of the body, and may also receive RF power to power the circuits. Using these approaches, the need for external electrical interfaces may be eliminated.

In one embodiment, the stretchable substrate is typically polymeric, e.g., polyimide or polydimethylsiloxane (PDMS). The single-crystal semiconductor devices themselves may be created on a silicon-on-insulator (SOI) carrier wafer in accordance with a circuit design implementing the desired functionality. Interconnect systems may also be created during this step to join smaller circuit islands. The processed single-crystal devices are removed from the SOI wafer (e.g., by etching) and are then placed in contact with an elastomeric stamp for transfer printing (via soft lithography) onto the desired flexible polymer substrate.

The circuitry is then transferred onto the stretchable substrate, which may be pre-stretched prior to transfer. The stretchable substrate serves as the catheter balloon, and can be conformed to the shape of an inflated balloon by a mold. The balloon polymer can be stretched over large strains (greater than 300 percent) without causing damage to the circuitry. The circuitry can be encapsulated with additional thin polymer layers to provide further protection from cracks or local contact stresses.

It is understood that stretchable circuitry may be realized using techniques other than those described above, combinations of the techniques listed above, and minor deviations from the techniques described above as will be apparent to those skilled in the art the art. For example, stretchable circuits may be formed on plastic, elastomeric, or other stretchable materials by sputtering, chemical vapor deposition, ink jet printing, or organic material deposition combined with patterning techniques. Semiconductor materials which may be used to make circuits may include amorphous silicon, polycrystalline silicon, single crystal silicon, conductive oxides, carbon annotates and organic materials. Islands of silicon connected by spiral interconnects made by surface micromachining or bulk etching may also be employed.

In use, an inflatable body 300 covered with stretchable circuitry 200 having an array of discrete operative devices 210 may be inserted in a lumen 1000. The discrete operative devices may include temperature sensors. The temperature sensors may be, for example, silicon band gap temperature sensor, consisting of silicon diodes. The forward voltage of these silicon diodes are sensitive to changes in temperature. Alternatively, platinum thin-film resistance temperature devices (RTD), which measure temperature based on temperature-induced changes in electrical resistance or thermocouple circuits that sense temperature changes between different thermoelectric materials can be utilized. For thermal resistors, the normalized changes in resistance (R), temperature coefficients of resistors (α), are related to the change in temperature (T) by $$\Delta R/R = \alpha T.$$

Platinum (500 Å) and an adhesion layer of chromium (150 Å) can be patterned and deposited on SOI wafers using thermal evaporation via e-beam to define individual RTD sensors. The RTD sensors can be integrated with CMOS based amplifiers, transducers, computation logic elements, and A/D circuitry on the same device islands as previously described.

Once the circuitry 200 is transferred onto the expandable body, in this embodiment, a balloon catheter 300, stretching and fatigue tests can be performed with a mechanical bending stage, capable of applying uneasily tensile or compressive strains in multiple directions or by repetitive inflation and deflation loading cycles. The mechanical bending stages can work in parallel with electrical probing stations (Agilent, 5155C) that are coupled to the circuit semi-conductors. In embodiments, to evaluate the performance of the circuitry, multiple cycling of heating and cooling tests can be performed. The circuits can be heated to 160° C. for 5 min. and subsequently cooled down before and after each electrical measurement.

To protect the circuitry from external damage, an encapsulating thin layer of polymer can be applied to the circuitry, including on the surface of the inflatable body after the circuitry is applied thereto. This encapsulating polymer layer may be extremely thin (<100 um) and photocurable, in order to allow selective curing in regions where direct contact with sensors is not required. In the embodiment described above, the RTD temperature sensors may be preferentially exposed for direct contact during photocuring. There are several polymers that may be used for preferential photocuring of the encapsulating layer, including but not limited to polyethylene glycol (PEG) with 2-hydroxy-2-methylpropiophenone photoinitiator. The photocurable PEG encapsulation cures once it is exposed to ultraviolet light. Photomasks designed using AUTOCAD can be printed to allow preferential curing of the surface of the inflatable body. These masks can be inserted as a filter into a UV light source stage coupled with a wide excitation UV filter. Exposure with an aligned mask enables polymerization in strategic regions of the inflatable body. Visual alignment during polymerization can be achieved with a CCD camera.

In embodiments, the inflatable body instrumented with an array of operative devices including temperature sensors can be deployed such that the temperature sensors are positioned in direct contact with the surface of plaque in the lumen upon inflation of the inflatable body. In such embodiments, the separation distance between sensors can be any that is manufacturable, a useful range may be, but is not limited to, 10 µm-10000 µm. Individual sensors may be coupled to a differential amplifier, and/or a buffer and/or an analog to digital converter. These circuits may be formed on the same, or different, discrete operative devices than the temperature sensors. The circuits may be laid out in an active matrix fashion such that the readings from multiple temperature sensors can be switched into and processed by one or a few amplifier/logic circuits. These sensor arrays record input signals that can then be channeled from the surface of the balloon to guidewires and a processor using metal electrodes deposited near the junction between the balloon surface and the catheter tubing. Alternatively, gold metal wires may be used to attach the balloon circuitry to the surface of the catheter guidewire using a wire bonder. Signals from the array of sensors can be processed using multiplexing techniques, including those described in published international patent application WO2009/114689 filed Mar. 12, 2009 the entirety of which is hereby incorporated herein by reference. Multiplexor component circuitry located in the base of the catheter guidewire can facilitate this type of data analysis/processing.

The device operator may use optical guidance during an x-ray angiography to deploy the balloon catheter once the guidewire reaches the region of the plaque location. The deformable and stretchable nature of the catheter balloon allows temperature measurements at multiple contact points on non-uniform surface contours such as that of arterial lumen and deposited plaque (shown as 1010 in FIGS. 1 and 2B). Once deployed, the interface electronics process the transmitted signals and produce a spatial temperature map of the plaque in the lumen. This data can be used by the device operator to detect temperature heterogeneity presence along the plaque and determine plaque type. Once plaque type is determined and surface contours are characterized, the balloon catheter can be deflated and removed.

Figure 4:
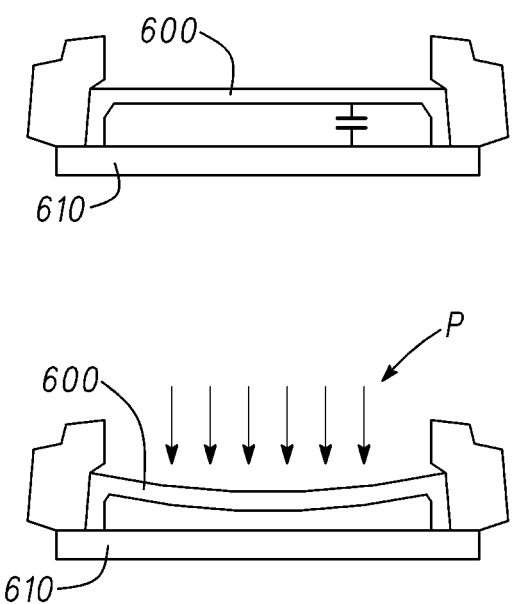
FIG. 4 is an embodiment of a sensor of the present invention.

In another embodiment of the invention, the stretchable circuitry comprises pressure sensor arrays. Such sensor arrays may be silicon-based and utilize piezo-resistive or capacitive sensing, or may be polymer based or optically based. In embodiments, a pressure sensor should have a working range and size suitable to the application, and should be amenable to application as described herein and tolerant to the stretching forces it will experience. FIG. 4 shows one exemplary pressure sensor which comprises a flexible and suspended diaphragm 600 of a flexible material such as thin single-crystal silicon, polysilicon, and/or silicon nitride thin film. The diaphragm 600 can be suspended directly above a base layer of doped silicon consisting of a metal electrode layer extracted from an SOI wafer. The polysilicon diaphragm layer may be formed as a suspended layer by first depositing an SiO2 layer on the silicon electrode 610. The polysilicon may then be deposited on the SiO2 layer, which in turn can be selectively etched. This etching step allows for the formation of a suspended and flexible polysilicon structure. In order to produce diaphragms with a controlled thickness, precise etch rates using HF must be used. This diaphragm with known thickness (2-10 µm thick), material modulus, and surface area and the underlying silicon electrode collectively form a parallel-plate capacitor. The sensor capacitance is a function of distance between the top polysilicon layer and the underlying silicon electrode. The capacitance recordings relate diaphragm deflection (caused by force P) to changes in capacitance.

In embodiments of the invention, the stretchable circuitry comprises an array of contact sensors. The contact sensors are designed to provide an on/off electrical resistance change in response to a pressure, such that when the applied pressure exceeds a predetermined threshold, the sensor provides an electrical signal indicating that it is in contact with, e.g., the arterial wall. One example of how to form a contact sensor is to make a simple mechanical-electrical switch, in which one conductor is mechanically pressed onto another conductor. The lower conductor, located on the surface balloon, consists of a metal wire that is non-continuous in one or more places to form an open circuit. Encapsulated around this open circuit is a diaphragm formed out of PDMS. The PDMS may be molded or etched into a diaphragm shape. The upper wall of the diaphragm is coated with a metal conductor, by standard means of photolithography patterning, electrochemical etching, etching, shadow evaporation, etc. The diaphragm is aligned and bonded to the surface of the balloon. The diaphragm is designed so that when a certain pressure is applied, it bends down to allow the upper conductor to contact and short-circuit the lower non-continuous conductor. This is done by control of the geometry (height and width) and materials of the diaphragm. In yet another non-limiting example, the diaphragm may be made with MEMS techniques, such as sacrificial silicon dioxide layers with a polysilicon bridge on top.

In embodiments of the invention, to measure relative pressure, each pressure sensor can be coupled with reference sensor unit, which has identical electrical characteristics except for a significantly lower pressure sensitivity. Difference in pressure measurements between the sensor and the reference unit enable compensation for many parasitic effects. The reference units may be created by leaving a passivation layer on the top surface of the polysilicon electrode. Having a reference unit along with a pressure sensor unit allows for differential pressure recordings. Once deployed, such sensor arrays can sense the presence and mechanical properties of the arterial lumen and plaque. They may also be used to estimate the diameter of the balloon and the lumen and provide feedback to the device operator to end balloon inflation at this point. This type of sensing can be combined with temperature sensor arrays to provide a thorough assessment of tissue mechanical and thermal properties during a single balloon deployment attempt. Pressure sensing also allows for creation of a tactile image map of the surface contours of the plaque. This type of mechanical imaging in a balloon catheter can indicate whether a stent has been successfully deployed when the balloon is inflated.

In embodiments of the invention, the plaque type is initially determined with temperature sensors and immediately afterwards, drug-delivery polymers and circuitry embedded in the balloon polymer are activated to cause local cooling and/or release of chemical agents, such as anti-inflammatory drugs, to local sites on the plaque where inflammation is present. In embodiments, light emitting electronics (such as LED) could be utilized to activate a drug delivery polymer.

In embodiments of the invention, the stretchable circuitry comprises packed array of active pixel sensors. Each pixel in the array may contain a photodetector, a pn junction blocking diode, an active amplifier, and an analog to digital converter, formed in a single piece of single crystalline silicon (50×50 µm2; 1.2 µm thick). These fabricated operative devices are fabricated in accordance with, for example, in Ko et al., "A hemispherical electronic eye camera based on compressible silicon optoelectronics," Nature (2008). In this embodiment, all of the circuitry may be encapsulated with a polymer layer such as PDMS to prevent contact stress induced damage of circuitry on the inflatable body, since there is no requirement for direct contact of the lumen with photosensor arrays. An array of photodetectors on the inflatable body positioned in close proximity to the plaque site within a the arterial lumen can provide high spatial resolution imaging without the need for a lens-based focusing due to the proximity of the photodetectors to the lumen. The catheter guidewire may comprise a light source, such as an optical fiber or an LED to provide illumination to the photodetectors for imaging the plaque and lumen surface.

In embodiments of the invention, the inflatable body is covered with ultrasound emitters and receivers to produce a lateral deep-tissue image of the plaque and arterial lumen.

In embodiments of the invention, the inflatable body is covered with stimulating and recording electrodes used for measuring plaque conductivity. Since vulnerable plaque is significantly less conductive than stable plaque and arterial tissue, this form of sensor array can help determine the plaque type based on measured conductivity of the plaque. Once the inflatable body is deployed, the electrodes are positioned in direct contact with the plaque deposits and electrical conductivity is measured. Again, this device can be combined with other sensor array types embedded in the stretchable inflatable body to provide multiple sensing and therapeutic functionalities in parallel.

Data collected by sensors at the site of the plaque can be interpreted against a baseline established by deploying the same inflatable body (or a second inflatable body on the same catheter) at a different location, which is free of plaque, in the lumen.

In embodiments of the invention, the array of operative devices includes temperature detectors, pressure sensors, and photodetectors collectively fabricated in a flexible and stretchable polymer-based balloon catheter substrate. These active device components can be designed using 0.6 µm design feature resolution or smaller. They may be integrated on the operative devices that are pieces of single crystalline silicon (50×50 µm2; 1.2 µm thick). Once the balloon is inserted in the arterial lumen, the device operator navigates the guidewire leading the balloon to the plaque location. The deployment of the balloon can stop blood flow intermittently. The guidewire is preferably fitted with an optical fiber or LED; the close contact of the imaging arrays to the lumen avoids the need for optical lens arrays, since light from the optical source may pass through the interconnect gap regions between the arrays, scatter through the lumen/plaque, and reach the photodetectors directly.

In this embodiment, the pressure sensor array detects when the inflatable body initially contacts the plaque and spatially maps the entire region of contact to ensure successful deployment. Temperature sensors continuously record data and spatially map temperature as a way to detect where in the arterial plaque there may be inflammation and macrophage deposits. The device operator may examine the data and decide whether to take immediate action through drug-delivery measures, stent deployment, or further tests on the plaque. The device operator may also utilize light imaging to visualize the plaque. Having integrated pressure sensors and imaging sensor arrays on the balloon, in addition to temperature sensors, allows for creation of a detailed tactile and visual map of the regions where the balloon contacts the plaque. This type of distributed mechanical sensing and imaging with an array of pressure sensors and photodetectors ensures that the stent and/or balloon contact the entire surface of the plaque. This embodiment of the balloon catheter can be deployed with a stent that may be fitted around the active sensing and imaging regions of the balloon.

The methods and systems described in connection with the invention described herein (the "Subject Methods and Systems") may be deployed in part or in whole through a machine that executes computer software, program codes, and/or instructions on a processor. The active stretchable circuitry described herein may be considered the machine necessary to deploy the Subject Methods and System in full or in part, or a separately located machine may deploy the Subject Methods and Systems in whole or in part. Thus, "machine" as referred to herein may be applied to the active circuitry described above, a separate processor, separate interface electronics or combinations thereof.

The Subject Methods and Systems invention may be implemented as a method on the machine, as a system or apparatus as part of or in relation to the machine, or as a computer program product embodied in a computer readable medium executing on one or more of the machines. The processor may be part of a server, client, network infrastructure, mobile computing platform, stationary computing platform, or other computing platform. A processor may be any kind of computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor, or any machine utilizing one, may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The Subject Methods and Systems described herein may be deployed in part or in whole through a machine that executes computer software on a server, client, firewall, gateway, hub, router, or other such computer and/or networking hardware. The software program may be associated with a server that may include a file server, print server, domain server, internet server, intranet server and other variants such as secondary server, host server, distributed server and the like. The server may include one or more of memories, processors, computer readable media, storage media, ports (physical and virtual), communication devices, and interfaces capable of accessing other servers, clients, machines, and devices through a wired or a wireless medium, and the like. The methods, programs or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the invention. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

If the Subject Methods and Systems are embodied in a software program, the software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the invention. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The Subject Methods and Systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements.

The methods, program codes, and instructions pertaining to the Subject Methods and Systems described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, EVDO, mesh, or other networks types.

The methods, program codes, and instructions pertaining to the Subject Methods and Systems described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer to peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions pertaining to the Subject Methods and Systems may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The Subject Methods and Systems described herein may transform physical and/or or intangible items from one state to another. The methods and systems described herein may also transform data representing physical and/or intangible items from one state to another.

The elements described and depicted herein and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipments, servers, routers and the like. Furthermore, the elements depicted in the flow chart and block diagrams or any other logical component may be implemented on a machine capable of executing program instructions. Thus, while the foregoing descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The Subject Methods and Systems, and steps associated therewith, may be realized in hardware, software or any combination of hardware and software suitable for a particular application. The hardware may include a general purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, each method described above in connection with the Subject Systems and Methods and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

All documents referenced herein are hereby incorporated by reference.

What is claimed is:

1. A device, comprising:
   an inflatable and expandable body having a stretchable surface, the stretchable surface having soft or elastic properties enabling the stretchable surface to be made longer or wider without tearing or breaking; and
   a stretchable electronic circuit embedded in or affixed to the stretchable surface of the inflatable and expandable body, the stretchable electronic circuit including a plurality of components that accommodate stretching or expanding of the stretchable surface of the inflatable and expandable body and remain functional when the stretchable surface is stretched or expanded, the plurality of components comprising:
a plurality of discrete operative devices arranged as device islands on the stretchable surface of the inflatable and expandable body; and
a plurality of stretchable interconnects embedded in or affixed to the stretchable surface of the inflatable and expandable body to electrically interconnect at least some of the plurality of discrete operative devices,
wherein at least one stretchable interconnect of the plurality of stretchable interconnects is directly attached to a first discrete operative device and to a second discrete operative device of the plurality of discrete operative devices to directly electrically interconnect the first discrete operative device to the second discrete operative device.

2. The device of claim 1, wherein at least some of the discrete operative devices comprise a CMOS integrated circuit, and at least one stretchable interconnect of the plurality of stretchable interconnects is directly attached to a CMOS integrated circuit of one discrete operative device and to a CMOS integrated circuit of a discrete operative device adjacent to the one discrete operative device to directly electrically interconnect the adjacent CMOS integrated circuits.

3. The device of claim 1, wherein said stretchable electronic circuit is printable.

4. The device of claim 1, wherein said stretchable electronic circuit is operable when said inflatable and expandable body is inflated and the stretchable surface is stretched.

5. The device of claim 4, wherein said inflatable and expandable body is expanded to stretch up to 500 percent.

6. The device of claim 1, wherein said device further comprises a transceiver receiving data from at least one of the plurality of discrete operative devices.

7. The device of claim 1, wherein at least some of the plurality of stretchable interconnects are configured to be buckled when said inflatable and expandable body is relaxed.

8. The device of claim 1, wherein at least some of the plurality of stretchable interconnects are non-coplanar with said inflatable and expandable body when said inflatable and expandable body is relaxed.

9. The device of claim 1, wherein at least some of the plurality of stretchable interconnects are coplanar with said inflatable and expandable body when said inflatable and expandable body is inflated.

10. The device of claim 1, wherein at least one of the plurality of discrete operative devices comprises an amplifier.

11. The device of claim 1, wherein at least one of the plurality of discrete operative devices comprises a semiconductor structure.

12. The device of claim 11, wherein said semi-conductor structure is a single crystalline semi-conductor structure.

13. The device of claim 1, wherein at least one of the plurality of discrete operative devices comprises a transducer.

14. The device of claim 1, wherein at least one of the plurality of discrete operative devices comprises at least one photodetector.

15. The device of claim 1, wherein at least one of the plurality of discrete operative devices comprises at least one ultrasound emitter.

16. The device of claim 1, wherein at least one of the plurality of discrete operative devices comprises light emitting electronics.

17. The device of claim 16, wherein said light emitting electronics comprise an LED.

18. The device of claim 1, wherein said stretchable electronic circuit comprises light emitting electronics.

19. The device of claim 18, wherein said light emitting electronics comprises an LED.

20. The device of claim 1, further comprising a processor, wherein at least one of the plurality of discrete operative devices is in electronic communication with the processor, said processor receiving data generated by said at least one discrete operative device, said processor being programmed to generate data for an image related to a body lumen.

21. The device of claim 1, wherein at least one of the plurality of discrete operative devices comprises a sensor.

22. The device of claim 21, wherein said sensor detects temperature data.

23. The device of claim 22, further comprising a processor, wherein at least one of the plurality of discrete operative devices is in electronic communication with the processor, said processor receiving data generated by said at least one discrete operative device, said processor being programmed to generate a spatial temperature map of a lumen.

24. The device of claim 21, wherein said sensor is a capacitance sensor.

25. The device of claim 21, wherein said sensor detects data related to pressure.

26. The device of claim 25, wherein said sensor is a piezoelectric sensor.

27. The device of claim 25, wherein said sensor detects mechanical properties of a lumen.

28. The device of claim 25, wherein said sensor detects an initial contact diameter of a lumen.

29. The device of claim 25, further comprising a processor, wherein at least one of the plurality of discrete operative devices is in electronic communication with the processor, said processor receiving data generated by said at least one discrete operative device, said processor being programmed to generate a tactile image map of a lumen.

30. The device of claim 21, wherein said sensor detects data related to electrical conductivity.

31. The device of claim 30, wherein said data related to electrical conductivity is the conductivity of plaque inside of a lumen.

32. The device of claim 21, wherein said sensor detects data related to pH.

33. The device of claim 21, wherein said sensor detects data related to enzymatic activity.

34. The device of claim 21, wherein said sensor detects data related to chemical activity.

35. The device of claim 1, wherein at least one of the plurality of discrete operative devices comprises a sensor that continuously generates data.

36. The device of claim 35, wherein said continuously generated data is recorded.

37. The device of claim 1, wherein said inflatable and expandable body is made of a polymer.

38. The device of claim 1, wherein said inflatable and expandable body is a balloon.

39. The device of claim 1, wherein the inflatable and expandable body is fitted with a stent.

40. The device of claim 1, further comprising a drug delivery polymer comprising a drug.

41. The device of claim 40, wherein said stretchable electronic circuit activates said drug delivery polymer.

42. The device of claim 1, wherein at least one of the plurality of discrete operative devices is ultra thin.

43. The device of claim 1, wherein each stretchable interconnect of the plurality of stretchable interconnects is directly attached to each discrete operative device of a pair of discrete operative devices to directly electrically interconnect the pair of discrete operative devices.

44. A balloon catheter apparatus, comprising:
an inflatable and expandable body having a stretchable surface, the stretchable surface having soft or elastic properties enabling the stretchable surface to be made longer or wider without tearing or breaking; and
stretchable electronic circuitry embedded in or disposed on the stretchable surface of the inflatable and expandable body, the stretchable electronic circuitry comprising:
a plurality of discrete operative devices arranged as device islands on the stretchable surface of the inflatable and expandable body, wherein the plurality of discrete operative devices include at least one of:
an integrated circuit;
a physical sensor;
a biological and/or chemical sensor;
an active pixel sensor;
an amplifier;
an analog-to-digital (A/D) converter;
a digital-to-analog (D/A) converter;
an optical collector;
an electro-mechanical transducer;
a piezo-electric actuator;
at least one light emitting diode (LED);
light emitting electronics;
at least one memory device;
a clock; and
active matrix switches; and
a plurality of stretchable interconnects embedded in or affixed to the stretchable surface of the inflatable and expandable body to electrically interconnect at least some of the plurality of discrete operative devices, wherein at least some of the plurality of stretchable interconnects are configured to be buckled or non-coplanar with the stretchable surface of the inflatable and expandable body when the stretchable surface of the inflatable and expandable body is relaxed,
wherein at least one stretchable interconnect of the plurality of stretchable interconnects is directly attached to a first discrete operative device and to a second discrete operative device of the plurality of discrete operative devices to directly electrically interconnect the first discrete operative device to the second discrete operative device.

45. The apparatus of claim 44, wherein at least some of the plurality of stretchable interconnects are configured to be substantially coplanar with the stretchable surface of the inflatable and expandable body when the stretchable surface of the inflatable and expandable body is significantly expanded.

46. The apparatus of claim 44, wherein the plurality of discrete operative devices include:

at least one pressure sensor;
at least one imaging sensor array; and
at least one temperature sensor.

47. The apparatus of claim 46, wherein the plurality of discrete devices are arranged on or in the stretchable surface of the inflatable and expandable body so as to provide distributed mechanical sensing and imaging information regarding a biological tissue, and wherein the apparatus further comprises:
a processor communicatively coupled to at least some of the plurality of discrete devices to facilitate generation of a tactile and visual map of the biological tissue based at least in part on the distributed mechanical sensing and imaging information.

48. The apparatus of claim 47, further comprising a stent fitted around the inflatable and expandable body.

49. A balloon catheter apparatus, comprising:
an inflatable and expandable body having a stretchable surface, the stretchable surface having soft or elastic properties enabling the stretchable surface to be made longer or wider without tearing or breaking; and
stretchable electronic circuitry embedded in or disposed on the stretchable surface of the inflatable and expandable body, the stretchable electronic circuitry comprising:
a plurality of discrete operative devices arranged as device islands on the stretchable surface of the inflatable and expandable body, wherein the plurality of discrete operative devices include a plurality of CMOS integrated circuits; and
a plurality of stretchable interconnects embedded in or affixed to the stretchable surface of the inflatable and expandable body to electrically interconnect at least some of the plurality of CMOS integrated circuits,
wherein at least one stretchable interconnect of the plurality of stretchable interconnects is directly attached to a first discrete operative device and to a second discrete operative device of the plurality of discrete operative devices to directly electrically interconnect the first discrete operative device to the second discrete operative device.

50. The apparatus of claim 49, wherein at least some of the plurality of CMOS integrated circuits are disposed on or in the stretchable surface of the inflatable and expandable body as a one-dimensional array.

51. The apparatus of claim 49, wherein at least some of the plurality of CMOS integrated circuits are disposed on or in the stretchable surface of the inflatable and expandable body as a two-dimensional array.

* * * * *